US007220554B2

(12) United States Patent
Kabat et al.

(10) Patent No.: US 7,220,554 B2
(45) Date of Patent: May 22, 2007

(54) METHODS FOR IDENTIFYING INHIBITORS

(75) Inventors: David Kabat, Portland, OR (US);
Mariana Marin, Portland, OR (US);
Susan L. Kozak, Portland, OR (US);
Kristine M. Rose, Portland, OR (US)

(73) Assignee: Oregon Health and Science University, Portland, OR (US)

( * ) Notice: Subject to any disclaimer, the term of this patent is extended or adjusted under 35 U.S.C. 154(b) by 192 days.

(21) Appl. No.: 10/838,770

(22) Filed: May 3, 2004

(65) Prior Publication Data

US 2004/0234956 A1 Nov. 25, 2004

Related U.S. Application Data

(60) Provisional application No. 60/473,357, filed on May 23, 2003.

(51) Int. Cl.
*G01N 33/53* (2006.01)
(52) U.S. Cl. .......................................... 435/7.1; 435/41
(58) Field of Classification Search ................. 435/7.1, 435/41
See application file for complete search history.

(56) References Cited

U.S. PATENT DOCUMENTS

| 6,653,443 | B2 | 11/2003 | Zhang et al. |
| 2002/0164743 | A1 | 11/2002 | Honjo et al. |
| 2003/0013844 | A1 | 1/2003 | Zang et al. |
| 2004/0009951 | A1 | 1/2004 | Malim et al. |

FOREIGN PATENT DOCUMENTS

| WO | WO 95/05851 | 3/1995 |
| WO | WO 03/095636 | 11/2003 |
| WO | WO 2004/013160 | 2/2004 |

OTHER PUBLICATIONS

Harris R. RNA Editing Enzyme APOBEC-1 and Some of its Homologs Can Act as DNA Mutators. Nov. 2002. Molecular Cell, vol. 10, p. 1247-1253.*
Kiser R. Assessment of a cytoprotection assay for the discovery and evaluation of anti-HIV compounds utilizing a genetically-imparied virus. 1996. Journal of Virological Methods, vol. 58, p. 99-109.*
Barak L. Fluorescent Low Density Lipoprotein for Observation of Dynamics of Inidividual Receptor Complexes on Cultured Human Fribroblasts. Sep. 1981. Journal of Cell Biology, vol. 90, p. 595-604.*
Baba, et al., "A small-molecule, nonpeptide CCR5 antagonist with highly potent and selective anti-HIV-1 activity," *PNAS*, 96:5698-5703 (May 1999).
Bogerd, et al., "A single amino acid difference in the host APOBEC3G protein controls the primate species specificity of HIV type 1 virion infectivity factor," *PNAS*, 101(11):3770-3774 (Mar. 16, 2004).
Conticello, et al., "The Vif Protein of HIV Triggers Degradation of the Human Antiretroviral DNA Deaminase APOBEC3G," *Current Biology*, 13:2009-2013 (Nov. 11, 2003).
Gaddis, et al., "Comprehensive Investigation of the Molecular Defect in *vif*-Deficient Human Immunodeficiency Virus Type 1 Virions," *J. Virology*, 77(10):5810-5820 (May 2003).
Harris, et al., "DNA Deamination Mediates Innate Immunity to Retroviral Infection," *Cell*, 113:803-809 (Jun. 13, 2003).
Iwai, et al., "Identification of the von Hippel-Lindau tumor-suppressor protein as part of an active E3 ubiquitin ligase complex," *PNAS*, 96(22):12436-12441 (Oct. 26, 1999).
Kao, et al., "The Human Immunodeficiency Virus Type 1 Vif Protein Reduces Intracellular Expression and Inhibits Packaging of APOBEC3G (CEM15), a Cellular Inhibitor of Virus Infectivity," *J. Virology*, 77(12):11398-11407 (Nov. 2003).
Lecossier, et al., "Hypermutation of HIV-1 DNA in the Absence of the Vif Protein," *Science*, 300:1112 (May 16, 2003).
Liu, et al., "Influence of Primate Lentiviral Vif and Proteasome Inhibitors on Human Immunodeficiency Virus Type 1 Virion Packaging of APOBEC3G," *J. Virology*, 78(4):2072-2081 (Feb. 2004).
Madani and Kabat, "An Endogenous Inhibitor of Human Immunodeficiency Virus in Human Lymphocytes is Overcome by the Viral Vif Protein," *J. Virology*, 72(12):10251-10255 (Dec. 1998).
Madani and Kabat, "Cellular and Viral Specificities of Human Immunodeficiency Virus Type 1 Vif Protein," *J. Virology*, 74(13):5982-5987 (Jul. 2000).
Mangeat, et al., "Broad antiretroviral defence by human APOBEC3G through lethal editing of nascent reverse transcripts," *Nature*, 424:99-103 (Jul. 3, 2003).
Mangeat, et al., "A Single Amino Acid Determinant Governs the Species-specific Sensitivity of APOBEC3G to Vif Action," *J. Biological Chemistry*, 279(15):144481-14483 (2004).
Mariani, et al., "Species-Specific Exclusion of APOBEC3G from HIV-1 Virions by Vif," *Cell*, 114:21-31 (Jul. 11, 2003).
Marin, et al., "HIV-1 Vif Protein binds the editing enzyme APOBEC3G and induces its degradation," *Nature Medicine*, 9(11):1398-1403 (Nov. 2003).
Mehle, et al., "Vif Overcomes the Innate Antiviral Activity of APOBEC3G by Promoting Its Degradation in the Ubiquitin-Proteasome Pathway," *J. Biological Chemistry*, 279(9):7792-7798 (Feb. 27, 2004).
Mehta, et al., "Molecular Cloning of Apobec-1 Complementation Factor, a Novel RNA-Binding Protein Involved in the Editing of Apolipoprotein B mRNA," *Molecular and Cellular Biology*, 20(9):1846-1854 (Mar. 2000).
Oberste and Gonda, "Conservation of amino-acid sequence motifs in lentivirus Vif proteins," *Virus Genes*, 6(1):95-102 (Jan. 1992) Abstract Only.

(Continued)

*Primary Examiner*—Bruce R. Campbell
*Assistant Examiner*—Louise Humphrey
(74) *Attorney, Agent, or Firm*—Klarquist Sparkman, LLP

(57) ABSTRACT

Vif binds to APOBEC3G and induces its rapid degradation, thus eliminating it from cells and preventing its incorporation into HIV-1 virions. Vif contains two domains, one that binds APOBEC3G and another with a conserved SLQ(Y/F)LA motif that mediates APOBEC3G degradation by a proteasome-dependent pathway. Provided herein are methods of exploiting these discoveries to develop compounds useful to inhibit Vif degradation of APOBEC3G, and thereby inhibit viral infection and/or replication.

25 Claims, 11 Drawing Sheets

OTHER PUBLICATIONS

Rose, et al., "The viral infectivity factor (Vif) of HIV-1 unveiled," *Trends in Molecular Medicine*, 10(6):291-297 (Jun. 2004).

Schröfelbauer, et al., "A single amino acid of APOBEC3G controls its species-specific interaction with virion infectivity factor (Vif)," *PNAS*, 101(11):3927-3932 (Mar. 16, 2004).

Sheehy, et al., "The antiretroviral enzyme APOBEC3G is degraded by the proteasome in response to HIV-1 Vif," *Nature Medicine*, 9(11):1404-1407 (Nov. 2003).

Sheehy, et al., "Isolation of a human gene that inhibits HIV-1 infection and is suppressed by the viral Vif protein," *Nature*, 418:646-650 (2002).

Shindo, et al., "The Enzymatic Activity of CEM15/Apobec-3G is Essential for the Regulation of the Infectivity of HIV-1 Virion by Not a Sole Determinant of its Antivirial Activity," *J. Biological Chemistry*, 278(45):44412-44416 (2003).

Simon, et al., "Evidence for a newly discovered cellular anti-HIV-1 phenotype," *Nature Medicine*, 4(12):1397-1400 (Dec. 1998).

Stopak, et al., "HIV-1 Vif Blocks the Antiviral Activity of APOBEC3G by Impairing Both Its Translation and Intracellular Stability," *Molecular Cell*, 12:591-601 (Sep. 2003).

Strizki, et al., "SCH-C (SCH 351125), an orally bioavailable, small molecule antagonist of the chemokine receptor CCR5, is a potent inhibitor of HIV-1 infection in vitro and in vivo," PNAS, 98(22):12718-12723 (Oct. 23, 2001).

Sonigo, et al., "Nucleotide sequence of the visna lentivirus: relationship to the AIDS virus," *Cell*, 42(1):369-82 (Aug. 1985) Abstract Only.

Vartanian, et al., "Death and the retrovirus," *Trends in Molecular Medicine*, 9(10):409-413 (Oct. 2003).

Vassilev, et al., "In Vivo Activation of the p53 Pathway by Small-Molecule Antagonists of MDM2," *Science*, 303:844-848 (Feb. 6, 2004).

Xu, et al., "A single amino acid substitution in human APOBEC3G antiretroviral enzyme confers resistance to HIV-1 virion infectivity factor-induced depletion," *PNAS*, 101(15):5652-5657 (Apr. 13, 2004).

Yu, et al., "Induction of APOBEC3G Ubiquitination and Degradation by an HIV-1 Vif-Cul5-SCF Complex," *Science*, 302:1056-1060 (Nov. 7, 2003).

Zhang, et al., "The cytidine deaminase CEM15 induces hypermutation in newly synthesized HIV-1 DNA," *Nature*, 424:94-98 (Jul. 3, 2003).

* cited by examiner

FIG. 1A
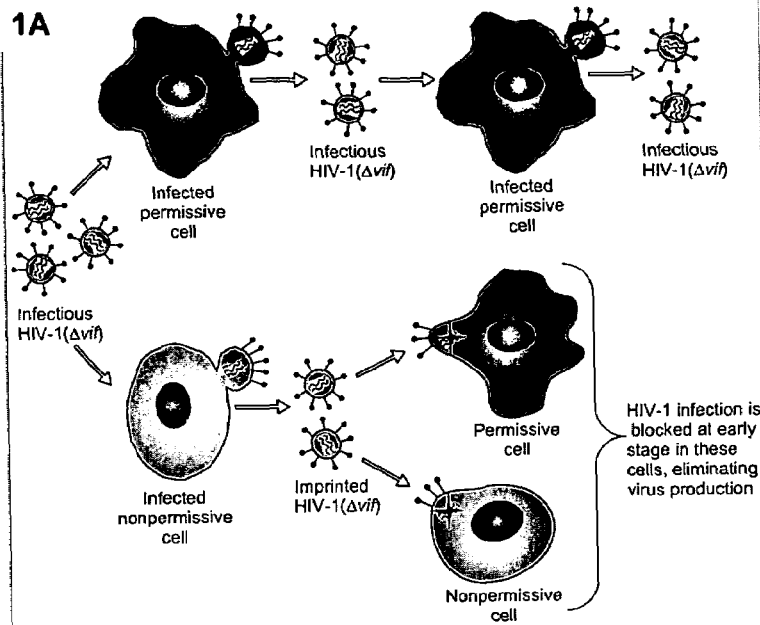
FIG. 1B
FIG. 2A
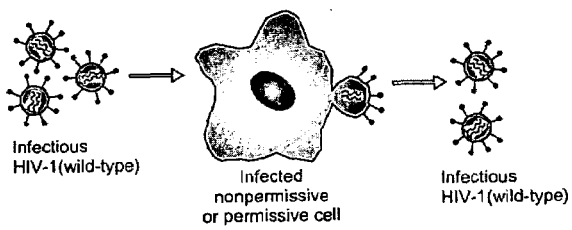
SOCS BC-box:  SLQ(H/Y)LCRXXΦ
Vif  BC-box:  SLQ(Y/F)LAΦΦΦΦ
FIG. 2B
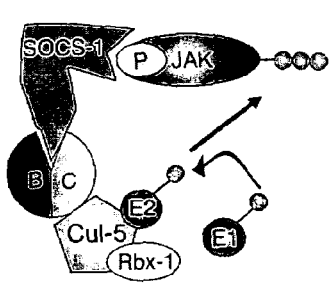
FIG. 2C
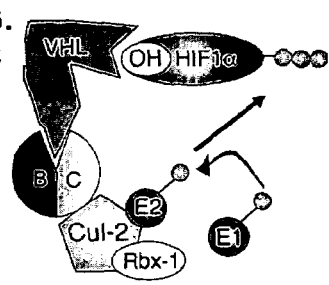
FIG. 2D
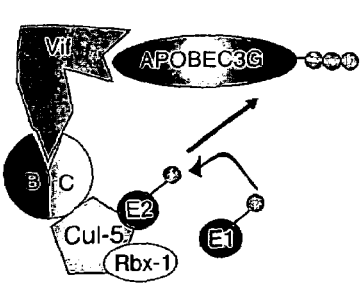
FIG. 2E
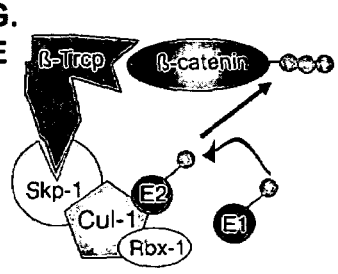

Apobec3G-Myc → p24 →

Vif →

LacZ-Myc →
Apobec3G-Myc →

Vif →

FIG. 10A 293T cells
FIG. 10B COS7 cells
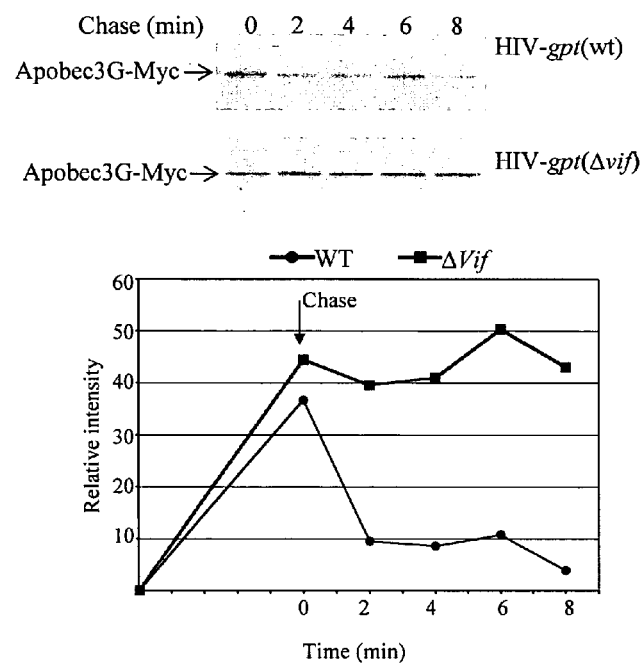
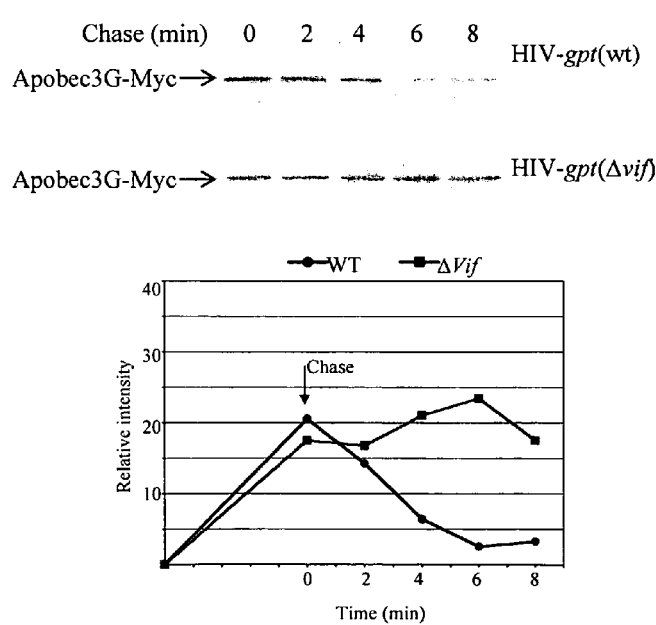

SEQUENCE LISTING

```
<160> NUMBER OF SEQ ID NOS: 16

<210> SEQ ID NO 1
<211> LENGTH: 1221
<212> TYPE: DNA
<213> ORGANISM: Artificial Sequence
<220> FEATURE:
<223> OTHER INFORMATION: Synthetic construct:  human APOBEC3G fused to
      Myc
```

```
<220> FEATURE:
<221> NAME/KEY: CDS
<222> LOCATION: (1)..(1221)
<220> FEATURE:
<221> NAME/KEY: misc_feature
<222> LOCATION: (1)..(1152)
<223> OTHER INFORMATION: encodes APOPBEC3G
<220> FEATURE:
<221> NAME/KEY: misc_feature
<222> LOCATION: (1156)..(1185)
<223> OTHER INFORMATION: encodes Myc epitope
<220> FEATURE:
<221> NAME/KEY: misc_feature
<222> LOCATION: (1201)..(1218)
<223> OTHER INFORMATION: encodes polyhistidine tag

<400> SEQUENCE: 1 atg aag cct cac ttc aga aac aca gtg gag cga atg tat cga gac aca      48
Met Lys Pro His Phe Arg Asn Thr Val Glu Arg Met Tyr Arg Asp Thr
 1               5                  10                  15 ttc tcc tac aac ttt tat aat aga ccc atc ctt tct cgt cgg aat acc      96
Phe Ser Tyr Asn Phe Tyr Asn Arg Pro Ile Leu Ser Arg Arg Asn Thr
             20                  25                  30 gtc tgg ctg tgc tac gaa gtg aaa aca aag ggt ccc tca agg ccc cct     144
Val Trp Leu Cys Tyr Glu Val Lys Thr Lys Gly Pro Ser Arg Pro Pro
         35                  40                  45 ttg gac gca aag atc ttt cga ggc cag gtg tat tcc gaa ctt aag tac     192
Leu Asp Ala Lys Ile Phe Arg Gly Gln Val Tyr Ser Glu Leu Lys Tyr
     50                  55                  60 cac cca gag atg aga ttc ttc cac tgg ttc agc aag tgg agg aag ctg     240
His Pro Glu Met Arg Phe Phe His Trp Phe Ser Lys Trp Arg Lys Leu
 65                  70                  75                  80 cat cgt gac cag gag tat gag gtc acc tgg tac ata tcc tgg agc ccc     288
His Arg Asp Gln Glu Tyr Glu Val Thr Trp Tyr Ile Ser Trp Ser Pro
                 85                  90                  95 tgc aca aag tgt aca agg gat atg gcc acg ttc ctg gcc gag gac ccg     336
Cys Thr Lys Cys Thr Arg Asp Met Ala Thr Phe Leu Ala Glu Asp Pro
            100                 105                 110 aag gtt acc ctg acc atc ttc gtt gcc cgc ctc tac tac ttc tgg gac     384
Lys Val Thr Leu Thr Ile Phe Val Ala Arg Leu Tyr Tyr Phe Trp Asp
        115                 120                 125 cca gat tac cag gag gcg ctt cgc agc ctg tgt cag aaa aga gac ggt     432
Pro Asp Tyr Gln Glu Ala Leu Arg Ser Leu Cys Gln Lys Arg Asp Gly
    130                 135                 140 ccg cgt gcc acc atg aag atc atg aat tat gac gaa ttt cag cac tgt     480
Pro Arg Ala Thr Met Lys Ile Met Asn Tyr Asp Glu Phe Gln His Cys
145                 150                 155                 160 tgg agc aag ttc gtg tac agc caa aga gag cta ttt gag cct tgg aat     528
Trp Ser Lys Phe Val Tyr Ser Gln Arg Glu Leu Phe Glu Pro Trp Asn
                165                 170                 175 aat ctg cct aaa tat tat ata tta ctg cac atc atg ctg ggg gag att     576
Asn Leu Pro Lys Tyr Tyr Ile Leu Leu His Ile Met Leu Gly Glu Ile
            180                 185                 190 ctc aga cac tcg atg gat cca ccc aca ttc act ttc aac ttt aac aat     624
Leu Arg His Ser Met Asp Pro Pro Thr Phe Thr Phe Asn Phe Asn Asn
        195                 200                 205 gaa cct tgg gtc aga gga cgg cat gag act tac ctg tgt tat gag gtg     672
Glu Pro Trp Val Arg Gly Arg His Glu Thr Tyr Leu Cys Tyr Glu Val
    210                 215                 220 gag cgc atg cac aat gac acc tgg gtc ctg ctg aac cag cgc agg ggc     720
Glu Arg Met His Asn Asp Thr Trp Val Leu Leu Asn Gln Arg Arg Gly
225                 230                 235                 240 ttt cta tgc aac cag gct cca cat aaa cac ggt ttc ctt gaa ggc cgc     768
```

| | | | | | | | | | | | | |
|---|---|---|---|---|---|---|---|---|---|---|---|---|
|Phe|Leu|Cys|Asn|Gln|Ala|Pro|His|Lys|His|Gly|Phe|Leu|Glu|Gly|Arg|
| | | |245| | |250| | | |255| | |

```
cat gca gag ctg tgc ttc ctg gac gtg att ccc ttt tgg aag ctg gac        816
His Ala Glu Leu Cys Phe Leu Asp Val Ile Pro Phe Trp Lys Leu Asp
        260                 265                 270 ctg gac cag gac tac agg gtt acc tgc ttc acc tcc tgg agc ccc tgc        864
Leu Asp Gln Asp Tyr Arg Val Thr Cys Phe Thr Ser Trp Ser Pro Cys
        275                 280                 285 ttc agc tgt gcc cag gaa atg gct aaa ttc att tca aaa aac aaa cac        912
Phe Ser Cys Ala Gln Glu Met Ala Lys Phe Ile Ser Lys Asn Lys His
        290                 295                 300 gtg agc ctg tgc atc ttc act gcc cgc atc tat gat gat caa gga aga        960
Val Ser Leu Cys Ile Phe Thr Ala Arg Ile Tyr Asp Asp Gln Gly Arg
305                 310                 315                 320 tgt cag gag ggg ctg cgc acc ctg gcc gag gct ggg gcc aaa att tca       1008
Cys Gln Glu Gly Leu Arg Thr Leu Ala Glu Ala Gly Ala Lys Ile Ser
            325                 330                 335 ata atg aca tac agt gaa ttt aag cac tgc tgg gac acc ttt gtg gac       1056
Ile Met Thr Tyr Ser Glu Phe Lys His Cys Trp Asp Thr Phe Val Asp
            340                 345                 350 cac cag gga tgt ccc ttc cag ccc tgg gat gga cta gat gag cac agc       1104
His Gln Gly Cys Pro Phe Gln Pro Trp Asp Gly Leu Asp Glu His Ser
            355                 360                 365 caa gac ctg agt ggg agg ctg cgg gcc att ctc cag aat cag gaa aac       1152
Gln Asp Leu Ser Gly Arg Leu Arg Ala Ile Leu Gln Asn Gln Glu Asn
        370                 375                 380 ttc gaa caa aaa ctc atc tca gaa gag gat ctg aat atg cat acc ggt       1200
Phe Glu Gln Lys Leu Ile Ser Glu Glu Asp Leu Asn Met His Thr Gly
385                 390                 395                 400 cat cat cac cat cac cat tga                                           1221
His His His His His His
            405

<210> SEQ ID NO 2
<211> LENGTH: 406
<212> TYPE: PRT
<213> ORGANISM: Artificial Sequence
<220> FEATURE:
<223> OTHER INFORMATION: Synthetic construct: human APOBEC3G fused to
      Myc

<400> SEQUENCE: 2

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
                20                  25                  30

Val Trp Leu Cys Tyr Glu Val Lys Thr Lys Gly Pro Ser Arg Pro Pro
            35                  40                  45

Leu Asp Ala Lys Ile Phe Arg Gly Gln Val Tyr Ser Glu Leu Lys Tyr
        50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
```

```
            130                 135                 140
Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
    370                 375                 380

Phe Glu Gln Lys Leu Ile Ser Glu Glu Asp Leu Asn Met His Thr Gly
385                 390                 395                 400

His His His His His His
                405

<210> SEQ ID NO 3
<211> LENGTH: 1932
<212> TYPE: DNA
<213> ORGANISM: Artificial sequence
<220> FEATURE:
<223> OTHER INFORMATION: Synthetic construct: Yellow fluorescent protein
      fused to human APOBEC3G fused to Myc
<220> FEATURE:
<221> NAME/KEY: CDS
<222> LOCATION: (1)..(1932)
<220> FEATURE:
<221> NAME/KEY: misc_feature
<222> LOCATION: (1)..(738)
<223> OTHER INFORMATION: encodes enhanced yellow fluorescent protein
      (EYFP)
<220> FEATURE:
<221> NAME/KEY: misc_feature
<222> LOCATION: (739)..(1890)
<223> OTHER INFORMATION: encodes APOBEC3G
<220> FEATURE:
<221> NAME/KEY: misc_feature
<222> LOCATION: (1891)..(1923)
<223> OTHER INFORMATION: encodes Myc epitope

<400> SEQUENCE: 3
```

-continued

| | |
|---|---|
| atg gtg agc aag ggc gag gag ctg ttc acc ggg gtg gtg ccc atc ctg<br>Met Val Ser Lys Gly Glu Glu Leu Phe Thr Gly Val Val Pro Ile Leu<br>1               5                   10                  15 | 48 |
| gtc gag ctg gac ggc gac gta aac ggc cac aag ttc agc gtg tcc ggc<br>Val Glu Leu Asp Gly Asp Val Asn Gly His Lys Phe Ser Val Ser Gly<br>            20                  25                  30 | 96 |
| gag ggc gag ggc gat gcc acc tac ggc aag ctg acc ctg aag ttc atc<br>Glu Gly Glu Gly Asp Ala Thr Tyr Gly Lys Leu Thr Leu Lys Phe Ile<br>        35                  40                  45 | 144 |
| tgc acc acc ggc aag ctg ccc gtg ccc tgg ccc acc ctc gtg acc acc<br>Cys Thr Thr Gly Lys Leu Pro Val Pro Trp Pro Thr Leu Val Thr Thr<br>50                  55                  60 | 192 |
| ttc ggc tac ggc ctg cag tgc ttc gcc cgc tac ccc gac cac atg aag<br>Phe Gly Tyr Gly Leu Gln Cys Phe Ala Arg Tyr Pro Asp His Met Lys<br>65                  70                  75                  80 | 240 |
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>                85                  90                  95 | 288 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>            100                 105                 110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>        115                 120                 125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>130                 135                 140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145                 150                 155                 160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>                165                 170                 175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>            180                 185                 190 | 576 |
| ccc gtg ctg ctg ccc gac aac cac tac ctg agc tac cag tcc gcc ctg<br>Pro Val Leu Leu Pro Asp Asn His Tyr Leu Ser Tyr Gln Ser Ala Leu<br>        195                 200                 205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>    210                 215                 220 | 672 |
| gtg acc gcc gcc ggg atc act ctc ggc atg gac gag ctg tac aag tcc<br>Val Thr Ala Ala Gly Ile Thr Leu Gly Met Asp Glu Leu Tyr Lys Ser<br>225                 230                 235                 240 | 720 |
| gga ctc aga tct cga gct atg aag cct cac ttc aga aac aca gtg gag<br>Gly Leu Arg Ser Arg Ala Met Lys Pro His Phe Arg Asn Thr Val Glu<br>                245                 250                 255 | 768 |
| cga atg tat cga gac aca ttc tcc tac aac ttt tat aat aga ccc atc<br>Arg Met Tyr Arg Asp Thr Phe Ser Tyr Asn Phe Tyr Asn Arg Pro Ile<br>            260                 265                 270 | 816 |
| ctt tct cgt cgg aat acc gtc tgg ctg tgc tac gaa gtg aaa aca aag<br>Leu Ser Arg Arg Asn Thr Val Trp Leu Cys Tyr Glu Val Lys Thr Lys<br>        275                 280                 285 | 864 |
| ggt ccc tca agg ccc cct ttg gac gca aag atc ttt cga ggc cag gtg<br>Gly Pro Ser Arg Pro Pro Leu Asp Ala Lys Ile Phe Arg Gly Gln Val<br>    290                 295                 300 | 912 |
| tat tcc gaa ctt aag tac cac cca gag atg aga ttc ttc cac tgg ttc<br>Tyr Ser Glu Leu Lys Tyr His Pro Glu Met Arg Phe Phe His Trp Phe | 960 |

```
                305                 310                 315                 320
agc aag tgg agg aag ctg cat cgt gac cag gag tat gag gtc acc tgg    1008
Ser Lys Trp Arg Lys Leu His Arg Asp Gln Glu Tyr Glu Val Thr Trp
                325                 330                 335 tac ata tcc tgg agc ccc tgc aca aag tgt aca agg gat atg gcc acg    1056
Tyr Ile Ser Trp Ser Pro Cys Thr Lys Cys Thr Arg Asp Met Ala Thr
                340                 345                 350 ttc ctg gcc gag gac ccg aag gtt acc ctg acc atc ttc gtt gcc cgc    1104
Phe Leu Ala Glu Asp Pro Lys Val Thr Leu Thr Ile Phe Val Ala Arg
                355                 360                 365 ctc tac tac ttc tgg gac cca gat tac cag gag gcg ctt cgc agc ctg    1152
Leu Tyr Tyr Phe Trp Asp Pro Asp Tyr Gln Glu Ala Leu Arg Ser Leu
                370                 375                 380 tgt cag aaa aga gac ggt ccg cgt gcc acc atg aag atc atg aat tat    1200
Cys Gln Lys Arg Asp Gly Pro Arg Ala Thr Met Lys Ile Met Asn Tyr
385                 390                 395                 400 gac gaa ttt cag cac tgt tgg agc aag ttc gtg tac agc caa aga gag    1248
Asp Glu Phe Gln His Cys Trp Ser Lys Phe Val Tyr Ser Gln Arg Glu
                405                 410                 415 cta ttt gag cct tgg aat aat ctg cct aaa tat tat ata tta ctg cac    1296
Leu Phe Glu Pro Trp Asn Asn Leu Pro Lys Tyr Tyr Ile Leu Leu His
                420                 425                 430 atc atg ctg ggg gag att ctg aga cac tcg atg gat cca ccc aca ttc    1344
Ile Met Leu Gly Glu Ile Leu Arg His Ser Met Asp Pro Pro Thr Phe
                435                 440                 445 act ttc aac ttt aac aat gaa cct tgg gtc aga gga cgg cat gag act    1392
Thr Phe Asn Phe Asn Asn Glu Pro Trp Val Arg Gly Arg His Glu Thr
                450                 455                 460 tac ctg tgt tat gag gtg gag cgc atg cac aat gac acc tgg gtc ctg    1440
Tyr Leu Cys Tyr Glu Val Glu Arg Met His Asn Asp Thr Trp Val Leu
465                 470                 475                 480 ctg aac cag cgc agg ggc ttt cta tgc aac cag gct cca cat aaa cac    1488
Leu Asn Gln Arg Arg Gly Phe Leu Cys Asn Gln Ala Pro His Lys His
                485                 490                 495 ggt ttc ctt gaa ggc cgc cat gca gag ctg tgc ttc ctg gac gtg att    1536
Gly Phe Leu Glu Gly Arg His Ala Glu Leu Cys Phe Leu Asp Val Ile
                500                 505                 510 ccc ttt tgg aag ctg gac ctg gac cag gac tac agg gtt acc tgc ttc    1584
Pro Phe Trp Lys Leu Asp Leu Asp Gln Asp Tyr Arg Val Thr Cys Phe
                515                 520                 525 acc tcc tgg agc ccc tgc ttc agc tgt gcc cag gaa atg gct aaa ttc    1632
Thr Ser Trp Ser Pro Cys Phe Ser Cys Ala Gln Glu Met Ala Lys Phe
                530                 535                 540 att tca aaa aac aaa cac gtg agc ctg tgc atc ttc act gcc cgc atc    1680
Ile Ser Lys Asn Lys His Val Ser Leu Cys Ile Phe Thr Ala Arg Ile
545                 550                 555                 560 tat gat gat caa gga aga tgt cag gag ggg ctg cgc acc ctg gcc gag    1728
Tyr Asp Asp Gln Gly Arg Cys Gln Glu Gly Leu Arg Thr Leu Ala Glu
                565                 570                 575 gct ggg gcc aaa att tca ata atg aca tac agt gaa ttt aag cac tgc    1776
Ala Gly Ala Lys Ile Ser Ile Met Thr Tyr Ser Glu Phe Lys His Cys
                580                 585                 590 tgg gac acc ttt gtg gac cac cag gga tgt ccc ttc cag ccc tgg gat    1824
Trp Asp Thr Phe Val Asp His Gln Gly Cys Pro Phe Gln Pro Trp Asp
                595                 600                 605 gga cta gat gag cac agc caa gac ctg agt ggg agg ctg cgg gcc att    1872
Gly Leu Asp Glu His Ser Gln Asp Leu Ser Gly Arg Leu Arg Ala Ile
                610                 615                 620 ctc cag aat cag gaa aac ttc gaa caa aaa ctc atc tca gaa gag gat    1920
```

-continued

```
Leu Gln Asn Gln Glu Asn Phe Glu Gln Lys Leu Ile Ser Glu Glu Asp
625                 630                 635                 640 ctg tct aga taa                                                          1932
Leu Ser Arg <210> SEQ ID NO 4
<211> LENGTH: 643
<212> TYPE: PRT
<213> ORGANISM: Artificial sequence
<220> FEATURE:
<223> OTHER INFORMATION: Synthetic construct: Yellow fluorescent protein
      fused to human APOBEC3G fused to Myc

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Met Lys Pro His Phe Arg Asn Thr Val Glu
                245                 250                 255

Arg Met Tyr Arg Asp Thr Phe Ser Tyr Asn Phe Tyr Asn Arg Pro Ile
            260                 265                 270

Leu Ser Arg Arg Asn Thr Val Trp Leu Cys Tyr Glu Val Lys Thr Lys
        275                 280                 285

Gly Pro Ser Arg Pro Pro Leu Asp Ala Lys Ile Phe Arg Gly Gln Val
290                 295                 300

Tyr Ser Glu Leu Lys Tyr His Pro Glu Met Arg Phe Phe His Trp Phe
305                 310                 315                 320

Ser Lys Trp Arg Lys Leu His Arg Asp Gln Glu Tyr Glu Val Thr Trp
                325                 330                 335
```

-continued

```
Tyr Ile Ser Trp Ser Pro Cys Thr Lys Cys Thr Arg Asp Met Ala Thr
            340                 345                 350
Phe Leu Ala Glu Asp Pro Lys Val Thr Leu Thr Ile Phe Val Ala Arg
        355                 360                 365
Leu Tyr Tyr Phe Trp Asp Pro Asp Tyr Gln Glu Ala Leu Arg Ser Leu
    370                 375                 380
Cys Gln Lys Arg Asp Gly Pro Arg Ala Thr Met Lys Ile Met Asn Tyr
385                 390                 395                 400
Asp Glu Phe Gln His Cys Trp Ser Lys Phe Val Tyr Ser Gln Arg Glu
                405                 410                 415
Leu Phe Glu Pro Trp Asn Asn Leu Pro Lys Tyr Tyr Ile Leu Leu His
            420                 425                 430
Ile Met Leu Gly Glu Ile Leu Arg His Ser Met Asp Pro Thr Phe
        435                 440                 445
Thr Phe Asn Phe Asn Asn Glu Pro Trp Val Arg Gly Arg His Glu Thr
    450                 455                 460
Tyr Leu Cys Tyr Glu Val Glu Arg Met His Asn Asp Thr Trp Val Leu
465                 470                 475                 480
Leu Asn Gln Arg Arg Gly Phe Leu Cys Asn Gln Ala Pro His Lys His
                485                 490                 495
Gly Phe Leu Glu Gly Arg His Ala Glu Leu Cys Phe Leu Asp Val Ile
            500                 505                 510
Pro Phe Trp Lys Leu Asp Leu Asp Gln Asp Tyr Arg Val Thr Cys Phe
        515                 520                 525
Thr Ser Trp Ser Pro Cys Phe Ser Cys Ala Gln Glu Met Ala Lys Phe
    530                 535                 540
Ile Ser Lys Asn Lys His Val Ser Leu Cys Ile Phe Thr Ala Arg Ile
545                 550                 555                 560
Tyr Asp Asp Gln Gly Arg Cys Gln Glu Gly Leu Arg Thr Leu Ala Glu
                565                 570                 575
Ala Gly Ala Lys Ile Ser Ile Met Thr Tyr Ser Glu Phe Lys His Cys
            580                 585                 590
Trp Asp Thr Phe Val Asp His Gln Gly Cys Pro Phe Gln Pro Trp Asp
        595                 600                 605
Gly Leu Asp Glu His Ser Gln Asp Leu Ser Gly Arg Leu Arg Ala Ile
    610                 615                 620
Leu Gln Asn Gln Glu Asn Phe Glu Gln Lys Leu Ile Ser Glu Glu Asp
625                 630                 635                 640
Leu Ser Arg
```

```
<210> SEQ ID NO 5
<211> LENGTH: 2817
<212> TYPE: DNA
<213> ORGANISM: Artificial sequence
<220> FEATURE:
<223> OTHER INFORMATION: Synthetic construct: human APOBEC3G fused to
      luciferase
<220> FEATURE:
<221> NAME/KEY: CDS
<222> LOCATION: (1)..(2817)
<220> FEATURE:
<221> NAME/KEY: misc_feature
<222> LOCATION: (1)..(1152)
<223> OTHER INFORMATION: encodes APOBEC3G
<220> FEATURE:
<221> NAME/KEY: misc_feature
<222> LOCATION: (1162)..(2817)
<223> OTHER INFORMATION: encodes Luciferase
```

```
<400> SEQUENCE: 5 atg aag cct cac ttc aga aac aca gtg gag cga atg tat cga gac aca      48
Met Lys Pro His Phe Arg Asn Thr Val Glu Arg Met Tyr Arg Asp Thr
1               5                   10                  15 ttc tcc tac aac ttt tat aat aga ccc atc ctt tct cgt cgg aat acc      96
Phe Ser Tyr Asn Phe Tyr Asn Arg Pro Ile Leu Ser Arg Arg Asn Thr
            20                  25                  30 gtc tgg ctg tgc tac gaa gtg aaa aca aag ggt ccc tca agg ccc cct     144
Val Trp Leu Cys Tyr Glu Val Lys Thr Lys Gly Pro Ser Arg Pro Pro
        35                  40                  45 ttg gac gca aag atc ttt cga ggc cag gtg tat tcc gaa ctt aag tac     192
Leu Asp Ala Lys Ile Phe Arg Gly Gln Val Tyr Ser Glu Leu Lys Tyr
    50                  55                  60 cac cca gag atg aga ttc ttc cac tgg ttc agc aag tgg agg aag ctg     240
His Pro Glu Met Arg Phe Phe His Trp Phe Ser Lys Trp Arg Lys Leu
65                  70                  75                  80 cat cgt gac cag gag tat gag gtc acc tgg tac ata tcc tgg agc ccc     288
His Arg Asp Gln Glu Tyr Glu Val Thr Trp Tyr Ile Ser Trp Ser Pro
                85                  90                  95 tgc aca aag tgt aca agg gat atg gcc acg ttc ctg gcc gag gac ccg     336
Cys Thr Lys Cys Thr Arg Asp Met Ala Thr Phe Leu Ala Glu Asp Pro
            100                 105                 110 aag gtt acc ctg acc atc ttc gtt gcc cgc ctc tac tac ttc tgg gac     384
Lys Val Thr Leu Thr Ile Phe Val Ala Arg Leu Tyr Tyr Phe Trp Asp
        115                 120                 125 cca gat tac cag gag gcg ctt cgc agc ctg tgt cag aaa aga gac ggt     432
Pro Asp Tyr Gln Glu Ala Leu Arg Ser Leu Cys Gln Lys Arg Asp Gly
    130                 135                 140 ccg cgt gcc acc atg aag atc atg aat tat gac gaa ttt cag cac tgt     480
Pro Arg Ala Thr Met Lys Ile Met Asn Tyr Asp Glu Phe Gln His Cys
145                 150                 155                 160 tgg agc aag ttc gtg tac agc caa aga gag cta ttt gag cct tgg aat     528
Trp Ser Lys Phe Val Tyr Ser Gln Arg Glu Leu Phe Glu Pro Trp Asn
                165                 170                 175 aat ctg cct aaa tat tat ata tta ctg cac atc atg ctg ggg gag att     576
Asn Leu Pro Lys Tyr Tyr Ile Leu Leu His Ile Met Leu Gly Glu Ile
            180                 185                 190 ctc aga cac tcg atg gat cca ccc aca ttc act ttc aac ttt aac aat     624
Leu Arg His Ser Met Asp Pro Pro Thr Phe Thr Phe Asn Phe Asn Asn
        195                 200                 205 gaa cct tgg gtc aga gga cgg cat gag act tac ctg tgt tat gag gtg     672
Glu Pro Trp Val Arg Gly Arg His Glu Thr Tyr Leu Cys Tyr Glu Val
    210                 215                 220 gag cgc atg cac aat gac acc tgg gtc ctg ctg aac cag cgc agg ggc     720
Glu Arg Met His Asn Asp Thr Trp Val Leu Leu Asn Gln Arg Arg Gly
225                 230                 235                 240 ttt cta tgc aac cag gct cca cat aaa cac ggt ttc ctt gaa ggc cgc     768
Phe Leu Cys Asn Gln Ala Pro His Lys His Gly Phe Leu Glu Gly Arg
                245                 250                 255 cat gca gag ctg tgc ttc ctg gac gtg att ccc ttt tgg aag ctg gac     816
His Ala Glu Leu Cys Phe Leu Asp Val Ile Pro Phe Trp Lys Leu Asp
            260                 265                 270 ctg gac cag gac tac agg gtt acc tgc ttc acc tcc tgg agc ccc tgc     864
Leu Asp Gln Asp Tyr Arg Val Thr Cys Phe Thr Ser Trp Ser Pro Cys
        275                 280                 285 ttc agc tgt gcc cag gaa atg gct aaa ttc att tca aaa aac aaa cac     912
Phe Ser Cys Ala Gln Glu Met Ala Lys Phe Ile Ser Lys Asn Lys His
    290                 295                 300
```

```
gtg agc ctg tgc atc ttc act gcc cgc atc tat gat gat caa gga aga    960
Val Ser Leu Cys Ile Phe Thr Ala Arg Ile Tyr Asp Asp Gln Gly Arg
305                 310                 315                 320 tgt cag gag ggg ctg cgc acc ctg gcc gag gct ggg gcc aaa att tca   1008
Cys Gln Glu Gly Leu Arg Thr Leu Ala Glu Ala Gly Ala Lys Ile Ser
                325                 330                 335 ata atg aca tac agt gaa ttt aag cac tgc tgg gac acc ttt gtg gac   1056
Ile Met Thr Tyr Ser Glu Phe Lys His Cys Trp Asp Thr Phe Val Asp
        340                 345                 350 cac cag gga tgt ccc ttc cag ccc tgg gat gga cta gat gag cac agc   1104
His Gln Gly Cys Pro Phe Gln Pro Trp Asp Gly Leu Asp Glu His Ser
355                 360                 365 caa gac ctg agt ggg agg ctg cgg gcc att ctc cag aat cag gaa aac   1152
Gln Asp Leu Ser Gly Arg Leu Arg Ala Ile Leu Gln Asn Gln Glu Asn
        370                 375                 380 aag ctt tcc atg gtc acc gac gcc aaa aac ata aag aaa ggc ccg gcg   1200
Lys Leu Ser Met Val Thr Asp Ala Lys Asn Ile Lys Lys Gly Pro Ala
385                 390                 395                 400 cca ttc tat ccg ctg gaa gat gga acc gct gga gag caa ctg cat aag   1248
Pro Phe Tyr Pro Leu Glu Asp Gly Thr Ala Gly Glu Gln Leu His Lys
                405                 410                 415 gct atg aag aga tac gcc ctg gtt cct gga aca att gct ttt aca gat   1296
Ala Met Lys Arg Tyr Ala Leu Val Pro Gly Thr Ile Ala Phe Thr Asp
        420                 425                 430 gca cat atc gag gtg gac atc act tac gct gag tac ttc gaa atg tcc   1344
Ala His Ile Glu Val Asp Ile Thr Tyr Ala Glu Tyr Phe Glu Met Ser
435                 440                 445 gtt cgg ttg gca gaa gct atg aaa cga tat ggg ctg aat aca aat cac   1392
Val Arg Leu Ala Glu Ala Met Lys Arg Tyr Gly Leu Asn Thr Asn His
450                 455                 460 aga atc gtc gta tgc agt gaa aac tct ctt caa ttc ttt atg ccg gtg   1440
Arg Ile Val Val Cys Ser Glu Asn Ser Leu Gln Phe Phe Met Pro Val
465                 470                 475                 480 ttg ggc gcg tta ttt atc gga gtt gca gtt gcg ccc gcg aac gac att   1488
Leu Gly Ala Leu Phe Ile Gly Val Ala Val Ala Pro Ala Asn Asp Ile
                485                 490                 495 tat aat gaa cgt gaa ttg ctc aac agt atg ggc att tcg cag cct acc   1536
Tyr Asn Glu Arg Glu Leu Leu Asn Ser Met Gly Ile Ser Gln Pro Thr
        500                 505                 510 gtg gtg ttc gtt tcc aaa aag ggg ttg caa aaa att ttg aac gtg caa   1584
Val Val Phe Val Ser Lys Lys Gly Leu Gln Lys Ile Leu Asn Val Gln
515                 520                 525 aaa aag ctc cca atc atc caa aaa att att atc atg gat tct aaa acg   1632
Lys Lys Leu Pro Ile Ile Gln Lys Ile Ile Ile Met Asp Ser Lys Thr
530                 535                 540 gat tac cag gga ttt cag tcg atg tac acg ttc gtc aca tct cat cta   1680
Asp Tyr Gln Gly Phe Gln Ser Met Tyr Thr Phe Val Thr Ser His Leu
545                 550                 555                 560 cct ccc ggt ttt aat gaa tac gat ttt gtg cca gag tcc ttc gat agg   1728
Pro Pro Gly Phe Asn Glu Tyr Asp Phe Val Pro Glu Ser Phe Asp Arg
                565                 570                 575 gac aag aca att gca ctg atc atg aac tcc tct gga tct act ggt ctg   1776
Asp Lys Thr Ile Ala Leu Ile Met Asn Ser Ser Gly Ser Thr Gly Leu
        580                 585                 590 cct aaa ggt gtc gct ctg cct cat aga act gcc tgc gtg aga ttc tcg   1824
Pro Lys Gly Val Ala Leu Pro His Arg Thr Ala Cys Val Arg Phe Ser
595                 600                 605 cat gcc aga gat cct att ttt ggc aat caa atc att ccg gat act gcg   1872
His Ala Arg Asp Pro Ile Phe Gly Asn Gln Ile Ile Pro Asp Thr Ala
                    610                 615                 620
```

```
att tta agt gtt gtt cca ttc cat cac ggt ttt gga atg ttt act aca   1920
Ile Leu Ser Val Val Pro Phe His His Gly Phe Gly Met Phe Thr Thr
625                 630                 635                 640 ctc gga tat ttg ata tgt gga ttt cga gtc gtc tta atg tat aga ttt   1968
Leu Gly Tyr Leu Ile Cys Gly Phe Arg Val Val Leu Met Tyr Arg Phe
                645                 650                 655 gaa gaa gag ctg ttt ctg agg agc ctt cag gat tac aag att caa agt   2016
Glu Glu Glu Leu Phe Leu Arg Ser Leu Gln Asp Tyr Lys Ile Gln Ser
            660                 665                 670 gcg ctg ctg gtg cca acc cta ttc tcc ttc ttc gcc aaa agc act ctg   2064
Ala Leu Leu Val Pro Thr Leu Phe Ser Phe Phe Ala Lys Ser Thr Leu
        675                 680                 685 att gac aaa tac gat tta tct aat tta cac gaa att gct tct ggt ggc   2112
Ile Asp Lys Tyr Asp Leu Ser Asn Leu His Glu Ile Ala Ser Gly Gly
690                 695                 700 gct ccc ctc tct aag gaa gtc ggg gaa gcg gtt gcc aag agg ttc cat   2160
Ala Pro Leu Ser Lys Glu Val Gly Glu Ala Val Ala Lys Arg Phe His
705                 710                 715                 720 ctg cca ggt atc agg caa gga tat ggg ctc act gag act aca tca gct   2208
Leu Pro Gly Ile Arg Gln Gly Tyr Gly Leu Thr Glu Thr Thr Ser Ala
                725                 730                 735 att ctg att aca ccc gag ggg gat gat aaa ccg ggc gcg gtc ggt aaa   2256
Ile Leu Ile Thr Pro Glu Gly Asp Asp Lys Pro Gly Ala Val Gly Lys
            740                 745                 750 gtt gtt cca ttt ttt gaa gcg aag gtt gtg gat ctg gat acc ggg aaa   2304
Val Val Pro Phe Phe Glu Ala Lys Val Val Asp Leu Asp Thr Gly Lys
        755                 760                 765 acg ctg ggc gtt aat caa aga ggc gaa ctg tgt gtg aga ggt cct atg   2352
Thr Leu Gly Val Asn Gln Arg Gly Glu Leu Cys Val Arg Gly Pro Met
770                 775                 780 att atg tcc ggt tat gta aac aat ccg gaa gcg acc aac gcc ttg att   2400
Ile Met Ser Gly Tyr Val Asn Asn Pro Glu Ala Thr Asn Ala Leu Ile
785                 790                 795                 800 gac aag gat gga tgg cta cat tct gga gac ata gct tac tgg gac gaa   2448
Asp Lys Asp Gly Trp Leu His Ser Gly Asp Ile Ala Tyr Trp Asp Glu
                805                 810                 815 gac gaa cac ttc ttc atc gtt gac cgc ctg aag tct ctg att aag tac   2496
Asp Glu His Phe Phe Ile Val Asp Arg Leu Lys Ser Leu Ile Lys Tyr
            820                 825                 830 aaa ggc tat cag gtg gct ccc gct gaa ttg gaa tcc atc ttg ctc caa   2544
Lys Gly Tyr Gln Val Ala Pro Ala Glu Leu Glu Ser Ile Leu Leu Gln
        835                 840                 845 cac ccc aac atc ttc gac gca ggt gtc gca ggt ctt ccc gac gat gac   2592
His Pro Asn Ile Phe Asp Ala Gly Val Ala Gly Leu Pro Asp Asp Asp
850                 855                 860 gcc ggt gaa ctt ccc gcc gcc gtt gtt gtt ttg gag cac gga aag acg   2640
Ala Gly Glu Leu Pro Ala Ala Val Val Val Leu Glu His Gly Lys Thr
865                 870                 875                 880 atg acg gaa aaa gag atc gtg gat tac gtc gcc agt caa gta aca acc   2688
Met Thr Glu Lys Glu Ile Val Asp Tyr Val Ala Ser Gln Val Thr Thr
                885                 890                 895 gcg aaa aag ttg cgc gga gga gtt gtg ttt gtg gac gaa gta ccg aaa   2736
Ala Lys Lys Leu Arg Gly Gly Val Val Phe Val Asp Glu Val Pro Lys
            900                 905                 910 ggt ctt acc gga aaa ctc gac gca aga aaa atc aga gag atc ctc ata   2784
Gly Leu Thr Gly Lys Leu Asp Ala Arg Lys Ile Arg Glu Ile Leu Ile
        915                 920                 925 aag gcc aag aag ggc gga aag atc gcc gtg taa                       2817
Lys Ala Lys Lys Gly Gly Lys Ile Ala Val
```

-continued

```
            930             935
```

<210> SEQ ID NO 6
<211> LENGTH: 938
<212> TYPE: PRT
<213> ORGANISM: Artificial sequence
<220> FEATURE:
<223> OTHER INFORMATION: Synthetic construct: human APOBEC3G fused to
      luciferase

<400> SEQUENCE: 6

```
Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350
```

```
His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
        370                 375                 380

Lys Leu Ser Met Val Thr Asp Ala Lys Asn Ile Lys Lys Gly Pro Ala
385                 390                 395                 400

Pro Phe Tyr Pro Leu Glu Asp Gly Thr Ala Gly Glu Gln Leu His Lys
                405                 410                 415

Ala Met Lys Arg Tyr Ala Leu Val Pro Gly Thr Ile Ala Phe Thr Asp
                420                 425                 430

Ala His Ile Glu Val Asp Ile Thr Tyr Ala Glu Tyr Phe Glu Met Ser
        435                 440                 445

Val Arg Leu Ala Glu Ala Met Lys Arg Tyr Gly Leu Asn Thr Asn His
        450                 455                 460

Arg Ile Val Val Cys Ser Glu Asn Ser Leu Gln Phe Phe Met Pro Val
465                 470                 475                 480

Leu Gly Ala Leu Phe Ile Gly Val Ala Val Ala Pro Ala Asn Asp Ile
                485                 490                 495

Tyr Asn Glu Arg Glu Leu Leu Asn Ser Met Gly Ile Ser Gln Pro Thr
                500                 505                 510

Val Val Phe Val Ser Lys Lys Gly Leu Gln Lys Ile Leu Asn Val Gln
        515                 520                 525

Lys Lys Leu Pro Ile Ile Gln Lys Ile Ile Met Asp Ser Lys Thr
        530                 535                 540

Asp Tyr Gln Gly Phe Gln Ser Met Tyr Thr Phe Val Thr Ser His Leu
545                 550                 555                 560

Pro Pro Gly Phe Asn Glu Tyr Asp Phe Val Pro Glu Ser Phe Asp Arg
                565                 570                 575

Asp Lys Thr Ile Ala Leu Ile Met Asn Ser Ser Gly Ser Thr Gly Leu
                580                 585                 590

Pro Lys Gly Val Ala Leu Pro His Arg Thr Ala Cys Val Arg Phe Ser
        595                 600                 605

His Ala Arg Asp Pro Ile Phe Gly Asn Gln Ile Ile Pro Asp Thr Ala
        610                 615                 620

Ile Leu Ser Val Val Pro Phe His His Gly Phe Gly Met Phe Thr Thr
625                 630                 635                 640

Leu Gly Tyr Leu Ile Cys Gly Phe Arg Val Val Leu Met Tyr Arg Phe
                645                 650                 655

Glu Glu Glu Leu Phe Leu Arg Ser Leu Gln Asp Tyr Lys Ile Gln Ser
                660                 665                 670

Ala Leu Leu Val Pro Thr Leu Phe Ser Phe Phe Ala Lys Ser Thr Leu
                675                 680                 685

Ile Asp Lys Tyr Asp Leu Ser Asn Leu His Glu Ile Ala Ser Gly Gly
        690                 695                 700

Ala Pro Leu Ser Lys Glu Val Gly Glu Ala Val Ala Lys Arg Phe His
705                 710                 715                 720

Leu Pro Gly Ile Arg Gln Gly Tyr Gly Leu Thr Glu Thr Thr Ser Ala
                725                 730                 735

Ile Leu Ile Thr Pro Glu Gly Asp Asp Lys Pro Gly Ala Val Gly Lys
                740                 745                 750

Val Val Pro Phe Phe Glu Ala Lys Val Val Asp Leu Asp Thr Gly Lys
        755                 760                 765

Thr Leu Gly Val Asn Gln Arg Gly Glu Leu Cys Val Arg Gly Pro Met
```

```
                        770             775             780
Ile Met Ser Gly Tyr Val Asn Asn Pro Glu Ala Thr Asn Ala Leu Ile
785             790             795             800

Asp Lys Asp Gly Trp Leu His Ser Gly Asp Ile Ala Tyr Trp Asp Glu
            805             810             815

Asp Glu His Phe Phe Ile Val Asp Arg Leu Lys Ser Leu Ile Lys Tyr
            820             825             830

Lys Gly Tyr Gln Val Ala Pro Ala Glu Leu Glu Ser Ile Leu Leu Gln
            835             840             845

His Pro Asn Ile Phe Asp Ala Gly Val Ala Gly Leu Pro Asp Asp
850             855             860

Ala Gly Glu Leu Pro Ala Ala Val Val Leu Glu His Gly Lys Thr
865             870             875             880

Met Thr Glu Lys Glu Ile Val Asp Tyr Val Ala Ser Gln Val Thr Thr
            885             890             895

Ala Lys Lys Leu Arg Gly Gly Val Val Phe Val Asp Glu Val Pro Lys
            900             905             910

Gly Leu Thr Gly Lys Leu Asp Ala Arg Lys Ile Arg Glu Ile Leu Ile
            915             920             925

Lys Ala Lys Lys Gly Gly Lys Ile Ala Val
            930             935

<210> SEQ ID NO 7
<211> LENGTH: 579
<212> TYPE: DNA
<213> ORGANISM: Human immunodeficiency virus
<220> FEATURE:
<221> NAME/KEY: CDS
<222> LOCATION: (1)..(579)

<400> SEQUENCE: 7 atg gaa aac aga tgg cag gtg atg att gtg tgg caa gta gac agg atg       48
Met Glu Asn Arg Trp Gln Val Met Ile Val Trp Gln Val Asp Arg Met
1               5                   10                  15 agg att aac aca tgg aaa aga tta gta aaa cac cat atg tat att tca       96
Arg Ile Asn Thr Trp Lys Arg Leu Val Lys His His Met Tyr Ile Ser
                20                  25                  30 agg aaa gct aag gac tgg ttt tat aga cat cac tat gaa agt act aat      144
Arg Lys Ala Lys Asp Trp Phe Tyr Arg His His Tyr Glu Ser Thr Asn
            35                  40                  45 cca aaa ata agt tca gaa gta cac atc cca cta ggg gat gct aaa tta      192
Pro Lys Ile Ser Ser Glu Val His Ile Pro Leu Gly Asp Ala Lys Leu
        50                  55                  60 gta ata aca aca tat tgg ggt ctg cat aca gga gaa aga gac tgg cat      240
Val Ile Thr Thr Tyr Trp Gly Leu His Thr Gly Glu Arg Asp Trp His
65                  70                  75                  80 ttg ggt cag gga gtc tcc ata gaa tgg agg aaa aag aga tat agc aca      288
Leu Gly Gln Gly Val Ser Ile Glu Trp Arg Lys Lys Arg Tyr Ser Thr
                85                  90                  95 caa gta gac cct gac cta gca gac caa cta att cat ctg cac tat ttt      336
Gln Val Asp Pro Asp Leu Ala Asp Gln Leu Ile His Leu His Tyr Phe
                100                 105                 110 gat tgt ttt tca gaa tct gct ata aga aat acc ata tta gga cgt ata      384
Asp Cys Phe Ser Glu Ser Ala Ile Arg Asn Thr Ile Leu Gly Arg Ile
            115                 120                 125 gtt agt cct agg tgt gaa tat caa gca gga cat aac aag gta gga tct      432
Val Ser Pro Arg Cys Glu Tyr Gln Ala Gly His Asn Lys Val Gly Ser
        130                 135                 140
```

-continued

```
cta cag tac ttg gca cta gca gca tta ata aaa cca aaa cag ata aag      480
Leu Gln Tyr Leu Ala Leu Ala Ala Leu Ile Lys Pro Lys Gln Ile Lys
145                 150                 155                 160 cca cct ttg cct agt gtt agg aaa ctg aca gag gac aga tgg aac aag      528
Pro Pro Leu Pro Ser Val Arg Lys Leu Thr Glu Asp Arg Trp Asn Lys
                165                 170                 175 ccc cag aag acc aag ggc cac aga ggg agc cat aca atg aat gga cac      576
Pro Gln Lys Thr Lys Gly His Arg Gly Ser His Thr Met Asn Gly His
            180                 185                 190 tag                                                                  579
```

<210> SEQ ID NO 8
<211> LENGTH: 192
<212> TYPE: PRT
<213> ORGANISM: Human immunodeficiency virus

<400> SEQUENCE: 8

```
Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
                20                  25                  30

Arg Lys Ala Lys Asp Trp Phe Tyr Arg His His Tyr Glu Ser Thr Asn
            35                  40                  45

Pro Lys Ile Ser Ser Glu Val His Ile Pro Leu Gly Asp Ala Lys Leu
        50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190
```

<210> SEQ ID NO 9
<211> LENGTH: 531
<212> TYPE: DNA
<213> ORGANISM: Artificial sequence
<220> FEATURE:
<223> OTHER INFORMATION: deletion construct derived from HIV Vif
<220> FEATURE:
<221> NAME/KEY: CDS
<222> LOCATION: (1)..(531)

<400> SEQUENCE: 9

```
atg gaa aac aga tgg cag gtg atg att gtg tgg caa gta gac agg atg       48
Met Glu Asn Arg Trp Gln Val Met Ile Val Trp Gln Val Asp Arg Met
1               5                   10                  15 agg att aac aca tgg aaa aga tta gta aaa cac cat atg tat att tca       96
Arg Ile Asn Thr Trp Lys Arg Leu Val Lys His His Met Tyr Ile Ser
                20                  25                  30
```

|  |  |
|---|---|
| agg aaa gct aag gac tgg ttt tat aga cat cac tat gaa agt act aat<br>Arg Lys Ala Lys Asp Trp Phe Tyr Arg His His Tyr Glu Ser Thr Asn<br>35    40    45 | 144 |
| cca aaa ata agt tca gaa gta cac atc cca cta ggg gat gct aaa tta<br>Pro Lys Ile Ser Ser Glu Val His Ile Pro Leu Gly Asp Ala Lys Leu<br>50    55    60 | 192 |
| gta ata aca aca tat tgg ggt ctg cat aca gga gaa aga gac tgg cat<br>Val Ile Thr Thr Tyr Trp Gly Leu His Thr Gly Glu Arg Asp Trp His<br>65    70    75    80 | 240 |
| ttg ggt cag gga gtc tcc ata gaa tgg agg aaa aag aga tat agc aca<br>Leu Gly Gln Gly Val Ser Ile Glu Trp Arg Lys Lys Arg Tyr Ser Thr<br>85    90    95 | 288 |
| caa gta gac cct gac cta gca gac caa cta att cat ctg cac gct gct<br>Gln Val Asp Pro Asp Leu Ala Asp Gln Leu Ile His Leu His Ala Ala<br>100    105    110 | 336 |
| gtt agt cct agg tgt gaa tat caa gca gga cat aac aag gta gga tct<br>Val Ser Pro Arg Cys Glu Tyr Gln Ala Gly His Asn Lys Val Gly Ser<br>115    120    125 | 384 |
| cta cag tac ttg gca cta gca gca tta ata aaa cca aaa cag ata aag<br>Leu Gln Tyr Leu Ala Leu Ala Ala Leu Ile Lys Pro Lys Gln Ile Lys<br>130    135    140 | 432 |
| cca cct ttg cct agt gtt agg aaa ctg aca gag gac aga tgg aac aag<br>Pro Pro Leu Pro Ser Val Arg Lys Leu Thr Glu Asp Arg Trp Asn Lys<br>145    150    155    160 | 480 |
| ccc cag aag acc aag ggc cac aga ggg agc cat aca atg aat gga cac<br>Pro Gln Lys Thr Lys Gly His Arg Gly Ser His Thr Met Asn Gly His<br>165    170    175 | 528 |
| tag | 531 |

<210> SEQ ID NO 10
<211> LENGTH: 176
<212> TYPE: PRT
<213> ORGANISM: Artificial sequence
<220> FEATURE:
<223> OTHER INFORMATION: deletion construct derived from HIV 165                 170                 175

<210> SEQ ID NO 11
<211> LENGTH: 558
<212> TYPE: DNA
<213> ORGANISM: Artificial sequence
<220> FEATURE:
<223> OTHER INFORMATION: deletion construct derived from HIV Vif
<220> FEATURE:
<221> NAME/KEY: CDS
<222> LOCATION: (1)..(558)

<400> SEQUENCE: 11

```
atg gaa aac aga tgg cag gtg atg att gtg tgg caa gta gac agg atg      48
Met Glu Asn Arg Trp Gln Val Met Ile Val Trp Gln Val Asp Arg Met
1               5                   10                  15 agg att aac aca tgg aaa aga tta gta aaa cac cat atg tat att tca      96
Arg Ile Asn Thr Trp Lys Arg Leu Val Lys His His Met Tyr Ile Ser
            20                  25                  30 agg aaa gct aag gac tgg ttt tat aga cat cac tat gaa agt act aat     144
Arg Lys Ala Lys Asp Trp Phe Tyr Arg His His Tyr Glu Ser Thr Asn
        35                  40                  45 cca aaa ata agt tca gaa gta cac atc cca cta ggg gat gct aaa tta     192
Pro Lys Ile Ser Ser Glu Val His Ile Pro Leu Gly Asp Ala Lys Leu
    50                  55                  60 gta ata aca aca tat tgg ggt ctg cat aca gga gaa aga gac tgg cat     240
Val Ile Thr Thr Tyr Trp Gly Leu His Thr Gly Glu Arg Asp Trp His
65                  70                  75                  80 ttg ggt cag gga gtc tcc ata gaa tgg agg aaa aag aga tat agc aca     288
Leu Gly Gln Gly Val Ser Ile Glu Trp Arg Lys Lys Arg Tyr Ser Thr
                85                  90                  95 caa gta gac cct gac cta gca gac caa cta att cat ctg cac tat ttt     336
Gln Val Asp Pro Asp Leu Ala Asp Gln Leu Ile His Leu His Tyr Phe
            100                 105                 110 gat tgt ttt tca gaa tct gct ata aga aat acc ata tta gga cgt ata     384
Asp Cys Phe Ser Glu Ser Ala Ile Arg Asn Thr Ile Leu Gly Arg Ile
        115                 120                 125 gtt agt cct agg tgt gaa tat caa gca gga cat gct gct gca cta gca     432
Val Ser Pro Arg Cys Glu Tyr Gln Ala Gly His Ala Ala Ala Leu Ala
    130                 135                 140 gca tta ata aaa cca aaa cag ata aag cca cct ttg cct agt gtt agg     480
Ala Leu Ile Lys Pro Lys Gln Ile Lys Pro Pro Leu Pro Ser Val Arg
145                 150                 155                 160 aaa ctg aca gag gac aga tgg aac aag ccc cag aag acc aag ggc cac     528
Lys Leu Thr Glu Asp Arg Trp Asn Lys Pro Gln Lys Thr Lys Gly His
                165                 170                 175 aga ggg agc cat aca atg aat gga cac tag                             558
Arg Gly Ser His Thr Met Asn Gly His
            180                 185
```

<210> SEQ ID NO 12
<211> LENGTH: 185
<212> TYPE: PRT
<213> ORGANISM: Artificial sequence
<220> FEATURE:
<223> OTHER INFORMATION: deletion construct derived from HIV Vif

<400> SEQUENCE: 12

```
Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
            20                  25                  30
```

```
Arg Lys Ala Lys Asp Trp Phe Tyr Arg His His Tyr Glu Ser Thr Asn
            35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Ala Ala Ala Leu Ala
    130                 135                 140

Ala Leu Ile Lys Pro Lys Gln Ile Lys Pro Pro Leu Pro Ser Val Arg
145                 150                 155                 160

Lys Leu Thr Glu Asp Arg Trp Asn Lys Pro Gln Lys Thr Lys Gly His
                165                 170                 175

Arg Gly Ser His Thr Met Asn Gly His
            180                 185

<210> SEQ ID NO 13
<211> LENGTH: 630
<212> TYPE: DNA
<213> ORGANISM: Artificial sequence
<220> FEATURE:
<223> OTHER INFORMATION: construct derived from HIV Vif fused to HA tag
<220> FEATURE:
<221> NAME/KEY: CDS
<222> LOCATION: (1)..(630)
<220> FEATURE:
<221> NAME/KEY: misc_feature
<222> LOCATION: (600)..(630)
<223> OTHER INFORMATION: encodes HA epitope tag

<400> SEQUENCE: 13 atg gag aac cgg tgg cag gtg atg att gtg tgg cag gtg gac cgc atg       48
Met Glu Asn Arg Trp Gln Val Met Ile Val Trp Gln Val Asp Arg Met
1               5                   10                  15 cgc att aac acc tgg aag cgc ctg gtg aag cac cac atg tac att agc       96
Arg Ile Asn Thr Trp Lys Arg Leu Val Lys His His Met Tyr Ile Ser
                20                  25                  30 cgc aaa gct aag gac tgg ttc tac cgc cac cac tac gag agc acc aac      144
Arg Lys Ala Lys Asp Trp Phe Tyr Arg His His Tyr Glu Ser Thr Asn
            35                  40                  45 ccc aag att agc agc gag gtg cac att ccc ctg ggc gac gcc aag ctg      192
Pro Lys Ile Ser Ser Glu Val His Ile Pro Leu Gly Asp Ala Lys Leu
    50                  55                  60 gtg att acg acc tac tgg ggc ctg cac acc ggc gag cgc gac tgg cac      240
Val Ile Thr Thr Tyr Trp Gly Leu His Thr Gly Glu Arg Asp Trp His
65                  70                  75                  80 ctg ggc cag ggc gtc tcc ata gaa tgg agg aaa aag aga tat agc aca      288
Leu Gly Gln Gly Val Ser Ile Glu Trp Arg Lys Lys Arg Tyr Ser Thr
                85                  90                  95 caa gta gac cct gac cta gca gac caa cta att cat ctg cac tat ttt      336
Gln Val Asp Pro Asp Leu Ala Asp Gln Leu Ile His Leu His Tyr Phe
            100                 105                 110 gat tgt ttt tca gaa tct gct ata aga aat acc ata tta gga cgt ata      384
Asp Cys Phe Ser Glu Ser Ala Ile Arg Asn Thr Ile Leu Gly Arg Ile
        115                 120                 125
```

```
gtt agt cct agg tgt gaa tat caa gca gga cat aac aag gta gga tct    432
Val Ser Pro Arg Cys Glu Tyr Gln Ala Gly His Asn Lys Val Gly Ser
    130                 135                 140 cta cag tac ttg gca cta gca gca tta ata aaa cca aaa cag ata aag    480
Leu Gln Tyr Leu Ala Leu Ala Ala Leu Ile Lys Pro Lys Gln Ile Lys
145                 150                 155                 160 cca cct ttg cct agt gtt agg aaa ctg aca gag gac aga tgg aac aag    528
Pro Pro Leu Pro Ser Val Arg Lys Leu Thr Glu Asp Arg Trp Asn Lys
                165                 170                 175 ccc cag aag acc aag ggc cac aga ggg agc cat aca atg aat gga cac    576
Pro Gln Lys Thr Lys Gly His Arg Gly Ser His Thr Met Asn Gly His
            180                 185                 190 gag aat tcg cgg ccg cta cac gtg tac cca tac gac gtc cca gac tac    624
Glu Asn Ser Arg Pro Leu His Val Tyr Pro Tyr Asp Val Pro Asp Tyr
        195                 200                 205 gct taa                                                            630
Ala
```

<210> SEQ ID NO 14
<211> LENGTH: 209
<212> TYPE: PRT
<213> ORGANISM: Artificial sequence
<220> FEATURE:
<223> OTHER INFORMATION: construct derived from HIV Vif fused to HA tag

<400> SEQUENCE: 14

```
Met Glu Asn Arg Trp Gln Val Met Ile Val Trp Gln Val Asp Arg Met
1               5                   10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

Glu Asn Ser Arg Pro Leu His Val Tyr Pro Tyr Asp Val Pro Asp Tyr
        195                 200                 205

Ala
```

<210> SEQ ID NO 15
<211> LENGTH: 33
<212> TYPE: DNA
<213> ORGANISM: artificial sequence

```
-continued

<220> FEATURE:
<223> OTHER INFORMATION: oligonucleotide primer; contains an XhoI
      restriction site
<220> FEATURE:
<221> NAME/KEY: misc_feature
<222> LOCATION: (4)..(9)
<223> OTHER INFORMATION: XhoI restriction site

<400> SEQUENCE: 15
gggctcgaga ggatgaagcc tcacttcaga aac                                    33

<210> SEQ ID NO 16
<211> LENGTH: 33
<212> TYPE: DNA
<213> ORGANISM: artificial sequence
<220> FEATURE:
<223> OTHER INFORMATION: oligonucleotide primer; contains a SfuI
      restriction site
<220> FEATURE:
<221> NAME/KEY: misc_feature
<222> LOCATION: (4)..(9)
<223> OTHER INFORMATION: SfuI restriction site

<400> SEQUENCE: 16
gggttcgaag ttttcctgat tctggagaat ggc                                    33
```

METHODS FOR IDENTIFYING INHIBITORS

REFERENCE TO RELATED CASES

This application claims the benefit of U.S. provisional application No. 60/473,357, filed May 23, 2003, which is incorporated herein in its entirety.

STATEMENT OF GOVERNMENT SUPPORT

This invention was made with United States government support pursuant to grant AI49729, from The National Institutes of Health; the United States government has certain rights in the invention.

FIELD OF THE DISCLOSURE

This disclosure relates to methods of identifying compounds that inhibit viral, particularly lentiviral, infectivity and replication. In particular, the disclosure relates to methods for identifying compounds that inhibit or interfere with an interaction between Vif and APOBEC3G, directly or indirectly, thereby inhibiting the infectivity and/or replication of a lentivirus.

BACKGROUND OF THE DISCLOSURE

HIV is a retrovirus that causes immunosuppression in humans (HIV disease), which culminates in a disease complex known as the acquired immunodeficiency syndrome (AIDS). This retrovirus is a member of the lentivirus subfamily, which includes non-oncogenic retroviruses that cause persistent (chronic active) infections in diseases with long incubation periods. These viruses usually infect cells of the immune system (particularly macrophages and T cells) and cause cytopathic effects in infected cells, such as syncytia and cell death. Lentiviral infections are not cleared by the immune system, and lead to accumulated immunologic damage over a period of many years.

The treatment of HIV disease has been significantly advanced by the recognition that combining different drugs with specific activities against different biochemical functions of the virus (combination therapy) can help reduce the rapid development of drug resistant viruses that was seen in response to single drug treatments. However, even with combination therapies, multi-drug resistant strains of the virus have emerged. There is therefore a continuing need for the development of new anti-retroviral drugs that act specifically at different steps of the viral infection and replication cycle.

The viral infectivity factor (Vif; also referred to as Sor or Q) encoded by HIV-1 is a small basic $M_r \sim 23,000$ phosphoprotein that is synthesized in a Rev-dependent manner during the late stages of virion production. Homologs of Vif exist in all lentiviruses, with the only exception being equine infectious anemia virus (EIAV) (Oberste & Gonda, *Virus Genes* 6; 95–102, 1992). There is significant conservation among vif open reading frames (ORFs) of the different lentiviruses (Sonigo et al., *Cell* 42; 369–382, 1985).

Although Vif has no effect on the release of HIV particles from infected cells, it enhances their infectivity fifty to one-hundred fold, in a manner that depends on the producer cells, and is independent of the target cells used to assay the infectivity. It is necessary for HIV-1 replication in vivo and in nonpermissive cells, which include T lymphocytes and macrophages and several leukemic T cell lines, but it is irrelevant in many other cells termed permissive (Gabuzda et al., *J. Virol.* 66, 6489–6495, 1992; Madani & Kabat, *J. Virol.* 72, 10251–10255, 1998; Simon et al., *Nat. Med.* 4, 1397–1400, 1998; Sheehy et al., *Nature* 418, 646–650, 2002). Consequently, HIV-1(Δvif) that has a deletion or mutation in its vif gene can efficiently replicate in permissive cell lines. Furthermore, the resulting HIV-1(Δvif) virions can also infect nonpermissive cells, resulting in proviral DNA integration and in production of virus-encoded proteins that are packaged with viral RNA into progeny virions that appear to have a normal composition (Gaddis et al., *J. Virol.* 77, 5810–5820, 2003; Ochsenbauer et al., *Gen. Virol.* 78, 627–635, 1997). However, these HIV-1(Δvif) virions that are derived from nonpermissive cells have been imprinted in a manner that severely inhibits reverse transcription during the subsequent cycle of infection (von Schwedler et al., *J. Virol.* 67, 4945–4955, 1993; Courcoul et al., *J. Virol.* 69, 2068–2074, 1995; Simon & Malim, *J. Virol.* 70, 5297–4305, 1996; Dettenhofer et al., *J. Virol.* 74, 8938–8945, 2000; Goncalves et al., *J. Virol.* 70, 8701–8709, 1996). Because these virions are inactive in all target cells including permissive or nonpermissive cells that contain Vif, the imprinting may be irreversible (Gabuzda et al., *J. Virol.* 66, 6489–6495, 1992; von Schwedler et al., *J. Virol.* 67, 4945–4955, 1993; Courcoul et al., *J. Virol.* 69, 2068–2074, 1995). This imprinting phenomenon, which is diagrammed in FIG. 1, has made elucidation of Vif function difficult because it is imposed in the cells producing virions but its outcome only becomes evident in the subsequently infected target cells.

The observed cellular specificity is believed to occur because nonpermissive (NP) cells but not permissive (P) cells contain an inhibitor of HIV-1 infectivity, and because Vif counteracts and neutralizes this inhibitor (Madani and Kabat, *J. Virol.* 27:10251–10255, 1998). Consequently, the vif gene is irrelevant for lentivirus replication in P cells because these cells lack the antiviral inhibitory factor. However, in NP cells the vif-deleted virions become inactivated during their release from the cells. Thus, NP cells can be infected with vif-deleted lentivirus particles that were made in P cells, but these infected NP cells release only noninfectious vif-deleted virions that cannot replicate within a culture or infected animal.

The nonpermissive phenotype is dominant in permissive x nonpermissive heterokaryons (Madani & Kabat, *J. Virol.* 72, 10251–10255, 1998; Simon et al., *Nat. Med.* 4, 1397–1400, 1998). This finding suggested that nonpermissive cells have a potent antiviral defense system that would efficiently inactivate HIV-1, were it not neutralized by Vif. This evidence implies that the antiviral inhibitory factor in NP cells can be countermanded and neutralized by Vif. This conclusion is supported by the finding that Vif functions in a species-restricted manner (Simon et al., *Embo J.,* 17:1259–1267, 1998). See also the recent paper by Mariani et al. (*Cell* 114:21–31, 2003). For example, Vif of African green monkey (SIVagm) does not have an effect in human cells, but it can neutralize the inhibitory factor in African green monkeys. Conversely, SIVagm viruses can replicate in human NP cells engineered to express the HIV-1 vif gene. The HIV Vif protein is therefore believed to neutralize an antiviral factor in nonpermissive human cells, but the HIV Vif protein would be unable to counteract the homologous antiviral factors of AGMs or of more distantly related species, such as mice.

Recently, Sheehy et al. (*Nature* 418, 646–650, 2002) proposed APOBEC3G (previously referred to as CEM-15), a member of the cytidine deaminase family of nucleic acid editing enzymes (Teng et al., *Science* 260, 1816–1819, 1993;

Harris et al., *Mol. Cell.* 10, 1247–1253, 2002), as the specific antiviral factor in nonpermissive cells. Most significantly, they reported that expression of APOBEC3G in permissive cell lines converted them to nonpermissive (Sheehy et al., *Nature* 418, 646–650, 2002).

Additionally, they reported that APOBEC3G is incorporated into HIV-1 virions regardless of whether Vif is present or absent in the producer cells. Since Vif is incorporated in small amounts into HIV-1 virions (Gaddis et al., *J. Virol.* 77, 5810–5820, 2003; Liu et al., *J. Virol.* 69, 7630–7638, 1995; Khan et al., *J. Virol.* 75, 7252–7265, 2001), and since it binds to RNA (Dettenhofer et al., *J. Virol.* 74, 8938–8945, 2000; Khan et al., *J. Virol.* 75, 7252–7265, 2001), Sheehy et al. suggested that Vif might bind to the HIV-1 genomic RNA and shield it from inactivation by APOBEC3G in the producer cells and/or in the released virions (*Nature* 418, 646–650, 2002; Gaddis et al., *J. Virol.* 77, 5810–5820, 2003), thus acting on the target of APOBEC3G rather than directly on the antiviral protein. Recently, it was shown that APOBEC3G causes cytidine deamination of HIV-1 negative strand DNA during the process of reverse transcription (Lecossier et al., *Science* 300, 1112, 2003; Zhang et al., *Nature* 424, 94–98, 2003; Mangeat et al., *Nature* 424, 99–103, 2003; Harris et al., *Cell* 113, 803–809, 2003).

It would be particularly advantageous to identify the mechanism by which Vif functions to neutralize APOBEC3G and related factors, because this mechanism (and its biochemical consequences and the pathways that influence this mechanism) would provide important targets in the treatment of HIV disease. Identification of the Vif mechanism would also enable the development of screening assays to test drugs that affect the intracellular expression or the mechanism by which Vif neutralizes the antiviral factor. Such drugs would be expected to interfere with the Vif mediated viral defense, and therefore would be useful to inhibit or interfere with lentiviral infection and/or replication.

SUMMARY OF THE DISCLOSURE

Vif binds to APOBEC3G and induces its rapid degradation, thus eliminating it from cells and preventing its incorporation into HIV-1 virions. Vif contains two domains, one that binds APOBEC3G and another with a conserved SLQ (Y/F)LA motif that mediates APOBEC3G degradation by a proteasome-dependent pathway. Provided herein are methods of exploiting these discoveries to identify and develop compounds useful to inhibit Vif degradation of APOBEC3G, and thereby inhibit viral infection and/or replication.

Provided herein in a first embodiment is a method for identifying an agent that affects the ability of a lentivirus to replicate in a cell in the presence of a Vif protein or peptide. Examples of such methods involve contacting the agent to the cell under conditions sufficient to allow interaction between the cell and the agent, evaluating an amount of an APOBEC3G protein or peptide in the cell, and comparing the amount of the APOBEC3G protein or peptide in the cell contacted with the agent to an amount of APOBEC3G protein or peptide in a control cell not treated with the agent, wherein a statistically significant difference in the amount of the APOBEC3G protein or peptide in the cell contacted with the agent, as compared to the control cell not treated with the agent, identifies the agent as one that affects the ability of a lentivirus to replicate in a cell.

Also provided are methods for identifying an agent that affects the ability of a lentivirus to replicate in a cell in the presence of a Vif protein or peptide, wherein an increase in the amount of APOBEC3G as compared to the control identifies the agent as one that inhibits lentiviral replication.

Yet another embodiment provides a method for identifying an agent that inhibits Vif-mediated degradation of APOBEC3G in a cell, which method involves contacting a cell which expresses Vif and APOBEC3G with a test agent under conditions sufficient to allow interaction between the cell and the agent; and determining whether the Vif-mediated degradation of APOBEC3G is inhibited.

Another embodiment provides for the use of an agent that interferes with Vif-mediated degradation of APOBEC3G in the manufacture of a medicament for the treatment of lentivirus infection. Also provided is use of an agent that interferes with Vif-mediated degradation of APOBEC3G in the manufacture of a medicament for the treatment of lentivirus infection, wherein the agent is identified using any one of the methods described herein.

Method of making a composition that inhibits the interaction of APOBEC3G and Vif are also provided, which methods involve incorporating an agent that inhibits Vif-mediated degradation of APOBEC3G in a pharmaceutically acceptable carrier. Also provided are methods of making a composition that inhibits the interaction of APOBEC3G and Vif, comprising incorporating an agent that inhibits Vif-mediated degradation of APOBEC3G in a pharmaceutically acceptable carrier, wherein the agent is identified using any one of the methods described herein.

Yet another embodiment is a method of inhibiting replication of a lentivirus (such as HIV, SIV, FIV or another lentivirus that contains a Vif gene) in a non-permissive (NP) cell, comprising interfering with Vif-mediated degradation of APOBEC3G in the cell.

Yet another embodiment is a method for preventing or inhibiting replication of a lentivirus in a cell, which method involves transferring a nucleic acid comprising a promoter operably linked to a nucleic acid sequence encoding APOBEC3G or an effective fragment or derivative thereof into the cell, wherein the transfer of the nucleic acid results in the expression of APOBEC3G and the inhibition of lentiviral replication. Optionally, the promoter is an inducible promoter or a constitutive promoter.

Also provided herein are specific protein and nucleic acid fusion molecules that include part or all of APOBEC3G and one or more additional peptides or domains that serve as a label or other agent capable of ready detection. Representative examples of such molecules include the nucleic acid molecules shown in SEQ ID NOs: 1, 3, and 5, and proteins shown in SEQ ID NOs: 2, 4, and 6.

The foregoing and other features and advantages will become more apparent from the following detailed description of several embodiments, which proceeds with reference to the accompanying figures.

BRIEF DESCRIPTION OF THE FIGURES

FIG. 1 illustrates the cellular specificity of HIV-1 viral infectivity factor (Vif).

FIG. 1A: Infection of permissive cells with HIV-1 (Δvif) (upper arrows) yields progeny HIV-1(Δvif) that can subsequently infect another permissive cell and continue to replicate within the culture. Nonpermissive cells (lower arrows) can be infected with HIV-1(Δvif) made by permissive cells, and they produce virions that appear to have a substantially normal protein and genomic RNA content. However, these HIV-1 (Δvif) virions are irreversibly imprinted (inactivated) in a manner that prevents completion of proviral DNA synthesis in the next cycle of infection, regardless of whether the target cells are permissive or nonpermissive.

FIG. 1B: HIV-1(wild-type) infection of either permissive or nonpermissive cells results in production of highly infectious HIV-1(wild-type) from both cell types. Although the imprinting mechanism is not shown here, recent evidence has indicated that it is caused by APOBEC3G incorporation into HIV-1(Δvif) virions made in nonpermissive cells. In contrast, APOBEC3G is excluded from virions when Vif is present.

FIG. 2 Viral infectivity factor (Vif) functions as a BC-box protein that specifically recruits APOBEC3G into an E1-E2-E3 Ub-enzyme complex for polyubiquitination and subsequent proteasomal degradation.

FIG. 2A: A consensus sequence alignment of the BC-box motif that occurs in suppressor of cytokine signaling (SOCS) proteins with the presumptive BC-box sequence that is conserved in lentiviral Vif proteins indicates significant homology between the two sequences (Φ being a hydrophobic residue, X being any amino acid). Cells contain different families of multisubunit E3 Ub-protein isopeptide ligases including the BC-box complex and a F-box containing complex called the SCF complex. BC-box and F-box sequences are unrelated and they exclusively recruit either Elongins B plus C or Skp-1, respectively (Margottin et al., *Mol Cell* 1, 565–574, 1998; VanDemark & Hill, *Curr Opin Struct Biol* 12, 822–830, 2003), but they are believed to have similar folded structures (VanDemark & Hill, *Curr Opin Struct Biol* 12, 822–830, 2003; Shamu et al., *Mol Biol Cell* 12, 2546–2555, 2001; Kikkert et al., *Biochem J* 358, 369–377, 2001). Although the multisubunit E3 ligase complex assembled by Vif was recently described as "SCF-like" (Yu et al., *Science* 302, 1056–1060, 2003), Vif appears to be a BC-box protein.

FIG. 2B–2E: Models representing BC-box complexes and SCF complexes. BC-box complexes contain Elongins B and C, a cullin, and a BC-box protein such as SOCS-1 (FIG. 2B); von Hippel Lindau tumor suppressor (VHL) (FIG. 2C); or Vif (FIG. 2D). SCF complexes contain Skp-1, a cullin, and an F-box protein such as β-transducin repeat containing protein (β-Trcp) (FIG. 2E). The BC-box (FIG. 2B–2D) or F-box (FIG. 2E) proteins associate with the general components of the E3 ligase complex (cullin and Rbx-1) via specific recognition by Elongin B plus C or Skp-1, respectively. SOCS-1 (FIG. 2B), VHL (FIG. 2C), Vif (FIG. 2D), and β-Trcp (FIG. 2E) recruit specific target proteins, JAK tyrosine kinase, hypoxia-inducible factor-1α (HIF1α), APOBEC3G, or β-catenin, respectively, to the E3 ligase complex for polyubiquitination and proteasomal degradation. Binding of the target protein JAK by SOCS-1 is dependent on tyrosine phosphorylation and HIF1α must undergo proline hydroxylation before it is recognized by the E3 ligase (modifications indicated by white ovals). The remaining components of the Ub pathway are recruited by the E3 ligase and include the E1-Ub activating enzyme, which transfers activated Ub to the E2-Ub conjugating enzyme. The E2 enzyme covalently transfers the Ub (small unlabeled circles) to form a Ub-target protein isopeptide bond.

FIG. 3 illustrates that expression of Vif down modulates APOBEC3G-Myc. 293T cells that had been cotransfected 36 hours earlier with plasmids for expression of APOBEC3G-Myc and for HIV-gpt(wt) or HIV-gpt(Δvif) were analyzed for the presence of APOBEC3G-Myc and Vif by Western immunoblotting.

FIG. 3C (right portion) is a Northern blot analysis of cellular RNAs. S2 is a loading control. Vif has no effect on expressions of APOBEC3G messenger RNA or of the negative control LacZ mRNA made using the same vector.

FIG. 4 illustrates that expression of human APOBEC3G-Myc in human 293T or African green monkey COS7 cells converts them to the nonpermissive phenotype. The cells were cotransfected with a plasmid for expression of APOBEC3G-Myc or pcDNA3.1-Myc in the presence of plasmids for expression of HIV-gpt(wild-type) or HIV-gpt (Δvif) viruses. Virions were subsequently harvested from the media. The titer of each virus made in the presence of APOBEC3G-Myc was normalized relative to the titer of the same virus made in the absence of APOBEC3G-Myc (n=6 for 293T cells and n=5 for COS7 cells; error bars are ±s.e.m.).

FIG. 5 illustrates the effects of Vif on APOBEC3G-Myc, analyzed by immunofluorescence microscopy. Five fields of cells with at least 100 cells/field were examined for each culture; error bars are ±s.e.m.

FIG. 7 illustrates the specificity of the Vif—APOBEC3G-Myc co-immunoprecipitation assay. 293T cells were cotransfected with pcDNA3.1-APOBECC3G-Myc, pcDNA3.1-LacZ-Myc, or a negative control pcDNA3.1-Myc vector, in the presence where indicated of pHIV-gpt (wild-type) or pHIV-gpt(Δvif).

FIG. 8 illustrates that Vif binds to APOBEC3G-Myc. APOBEC3G-Myc was immunoprecipitated with a Myc-specific monoclonal antibody from extracts of cultures that contained or lacked Vif, and the immunoprecipitates were subsequently analyzed by Western immunoblotting using a Vif-specific antiserum.

FIG. 9 illustrates control studies concerning Vif-induced APOBEC3G-Myc degradation. 293T cell cultures were cotransfected with vectors for expression of APOBEC3G-Myc and with HIV-gpt(wild-type) or HIV-gpt(Δvif).

FIG. 10 shows that Vif causes rapid degradation of APOBEC3G-Myc. 293T (FIG. 10A) and COS7 (FIG. 10B) cell cultures were cotransfected with vectors for expression of APOBEC3G-Myc and HIV-gpt(wt) or HIV-gpt(Δvif). After 36 hours, the cells were pulse-labeled by incorporation of L-[$^{35}$S]amino acids for 4 minutes and chased in the presence of cycloheximide for the times indicated. APOBEC3G-Myc was immunoprecipitated from the cell extracts and the immunoprecipitated proteins were analyzed by electrophoresis followed by autoradiographic detection. The relative intensities of the APOBEC3G-Myc bands were determined by densitometry.

FIG. 11 illustrates that APOBEC3G-Myc degradation by Vif involves a proteasome-dependent pathway. 293T cell cultures were cotransfected with vectors for expression of APOBEC3G-Myc and HIV-gpt(wt) or HIV-gpt(Δvif). Aliquots of the eluted protein were analyzed by Western immunoblotting using Myc-specific or ubiquitin-specific antibodies.

FIG. 12 shows that the YFP-APOBEC3G-Myc and APOBEC3G-Myc chimeras retain antiviral activity of the intact APOBEC3G protein.

SEQUENCE LISTING

Figure 3A:
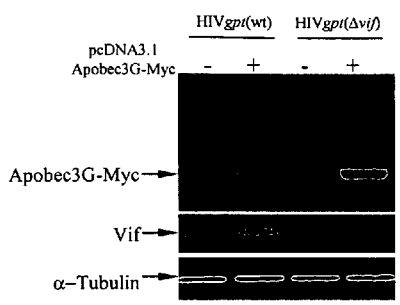
FIG. 3A shows that APOBEC3G-Myc is strongly down modulated by HIV-gpt(wt) compared to HIV-gpt(Δvif). The accuracy of the protein loading methods was verified by immunoblotting for α-tubulin. The HIV-gpt and APOBEC3G-Myc vectors were transfected in a 1:1 molar ratio.

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleotide and amino acid sequences of the fusion APOBEC3G-Myc. The amino acid sequence alone is shown in SEQ ID NO: 2.

SEQ ID NO: 3 shows the nucleotide and amino acid sequences of the fusion YFP-APOBEC3G-Myc. The amino acid sequence alone is shown in SEQ ID NO: 4.

SEQ ID NO: 5 shows the nucleotide and amino acid sequences of the fusion APOBEC3G-luciferase. The amino acid sequence alone is shown in SEQ ID NO: 6.

SEQ ID NO: 7 shows the nucleotide and amino acid sequences of Vif. The amino acid sequence alone is shown in SEQ ID NO: 8.

SEQ ID NO: 9 shows the nucleotide and amino acid sequences of Vif(Δ10). The amino acid sequence alone is shown in SEQ ID NO: 10.

SEQ ID NO: 11 shows the nucleotide and amino acid sequences of Vif(Δ12). The amino acid sequence alone is shown in SEQ ID NO: 12.

SEQ ID NO: 13 shows the nucleotide and amino acid sequences of HVif-HA, which contains an HA tag and employs the codon optimized version of VIF (HVif; Nguyen et al., *Virology* 319(2):163–175, 2004). The amino acid sequence alone is shown in SEQ ID NO: 14.

SEQ ID NOs: 15 and 16 show upstream and downstream primers for the APOBEC3G coding region. The upstream primer (SEQ ID NO: 15) contains an XhoI restriction site; the downstream primer (SEQ ID NO: 16) contains a SfuI restriction site.

DETAILED DESCRIPTION

I. Abbreviations

| | |
|---|---|
| APOBEC | apolipoprotein B mRNA editing enzyme complex |
| DMSO | dimethylsulfoxide |
| GFP | green fluorescent protein |
| gpt | guanine phosphoribosyltransferase |
| HIV | human immunodeficiency virus |
| NP | non-permissive (cells) |
| P | permissive (cells) |
| Vif | viral infectivity factor |
| YFP | yellow fluorescent protein |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

An "agent" includes conventional chemical pharmaceutical compounds, as well as polypeptides, peptidomimetics, biological agents, antibodies or other molecules with a desired function.

An "animal" is a living multicellular vertebrate organism, a category which includes, for example, mammals and birds. A "mammal" includes both human and non-human mammals. Similarly, the term "subject" includes both human and veterinary subjects.

The term "antibody" as used in this invention includes polyclonal and monoclonal antibodies. The term includes intact molecules as well as fragments thereof, such as Fab, F(ab')$_2$, and Fv which are capable of binding the epitopic determinant.

Antisense, Sense, and Antigene: Double-stranded DNA (dsDNA) has two strands, a 5' to 3' strand, referred to as the plus strand, and a 3' to 5' strand (the reverse complement), referred to as the minus strand. Because RNA polymerase adds nucleic acids in a 5' to 3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Array: An arrangement of molecules, particularly biological macromolecules (such as polypeptides or nucleic acids) or biological samples (such as tissue sections) in addressable locations on a substrate, usually a flat substrate such as a membrane, plate or slide. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized to such an extent that it benefits from microscopic examination for evaluation.

Within an array, each arrayed molecule (e.g., oligonucleotide) or sample (more generally, a "feature" of the array) is addressable, in that its location can be reliably and consistently determined within the at least two dimensions on the array surface. Thus, in ordered arrays the location of each feature is usually assigned to a sample at the time when it is spotted onto or otherwise applied to the array surface, and a key may be provided in order to correlate each location with the appropriate feature.

Often, ordered arrays are arranged in a symmetrical grid pattern, but samples could be arranged in other patterns (e.g., in radially distributed lines, spiral lines, or ordered clusters). Arrays are computer readable, in that a computer can be programmed to correlate a particular address on the array with information (such as identification of the arrayed sample and hybridization or binding data, including for instance signal intensity). In some examples of computer readable array formats, the individual spots on the array surface will be arranged regularly, for instance in a Cartesian grid pattern, that can be correlated to address information by a computer.

The sample application spot (or feature) on an array may assume many different shapes. Thus, though the term "spot" is used herein, it refers generally to a localized deposit of nucleic acid or other biomolecule, and is not limited to a round or substantially round region. For instance, substantially square regions of application can be used with arrays, as can be regions that are substantially rectangular (such as a slot blot-type application), or triangular, oval, irregular, and so forth. The shape of the array substrate itself is also immaterial, though it is usually substantially flat and may be rectangular or square in general shape.

Binding or interaction: A direct or indirect association between two substances or molecules, such as the hybridization of one nucleic acid molecule to another (or itself), or a specific association between two or more proteins, such as an antibody and its cognate antigen or components of a multi-protein complex.

cDNA: A DNA molecule lacking internal, non-coding segments (e.g., introns) and regulatory sequences that determine transcription. By way of example, cDNA may be synthesized in the laboratory by reverse transcription from messenger RNA extracted from cells.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Non-limiting examples of conservative amino acid substitutions include: Ala for Ser; Arg for Lys; Asn for Gln or His; Asp for Glu; Cys for Ser; Gln for Asn; Glu for Asp; His for Asn or Gln; Ile for Leu or Val; Leu for Ile or Val; Lys for Arg, Gln or Glu; Met for Leu or Ile; Phe for Met, Leu or Tyr; Ser for Thr; Thr for Ser; Trp for Tyr; Tyr for Trp or Phe; and Val for Ile or Leu;

DNA (deoxyribonucleic acid): DNA is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

The term "epitope" means any antigenic determinant on an antigen to which the paratope of an antibody binds. Epitopic determinants usually consist of chemically active surface groupings of molecules such as amino acids or sugar side chains, and usually have specific three dimensional structural characteristics, as well as specific charge characteristics.

Epitope tags: Short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of useful epitope tags include FLAG, T7, HA (hemagglutinin) and myc.

Fluorescent protein: A protein that either directly (through its primary, secondary, or tertiary structure) or indirectly (through a co-factor, non-protein chromophore, or a substrate, or due to the addition of a fluor) produces or emits fluorescent light. One non-limiting example of a fluorescent protein is the green fluorescent protein (GFP) from the Pacific Northwest jellyfish, *Aequorea Victoria*.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515–540 λ. Red fluorophores, for example Texas Red, Cy5 and tetramethylrhodamine, are characterized by their emission at wavelengths generally in the range of 590–690 λ.

Examples of fluorophores that may be used are provided in U.S. Pat. No. 5,866,366 to Nazarenko et al., and include for instance: 4-acetamido-4'-isothiocyanatostilbene-2,2'-disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Fusion protein: A protein that has two (or more) parts fused together, which are not found joined together in nature. In general, the two domains are genetically fused together, in that nucleic acid molecules that encode each protein part or domain are functionally linked together, for instance directly or by a linker oligonucleotide, thereby producing a single fusion-encoding nucleic acid molecule. The translated product of such a fusion-encoding nucleic acid molecule is the fusion protein. Fusion proteins are sometimes referred to as "chimeric" proteins, because they have fused parts derived from different origins.

Green fluorescent protein (GFP): GFP is a 238 amino acid, spontaneously fluorescent protein, originally isolated from the Pacific Northwest jellyfish *Aequorea victoria*. The amino acid sequence of wt GFP is well known (see, for instance, GenBank Accession Number M62654). This protein has become an extremely popular tool in molecular and cell biology (for reviews: Tsien, *Annu. Rev. Biochem.* 67:509–544, 1998; Remington, In *Bioluminescence and chemiluminescence* (eds. T. O. Baldwin and M. M. Sigler), pp. 195–211, 2000, Academic, San Diego, Calif.).

In addition to GFP being highly fluorescent, protease resistant, and very stable throughout a wide range of pH and solvent conditions, it also has the advantage of being functional as a single protein encoded by a single gene. These traits result in a biological probe molecule (marker) that can be expressed in nearly all organisms. It also can be targeted to subcellular organelles by a host cell, for instance through the inclusion of a targeting sequence on the construction from which it is expressed. GFP is a non-invasive indicator, which permits experiments to be conducted and monitored in a single cell over a period of time.

A "mutant" GFP is a green fluorescent protein (or nucleic acid encoding such) that has at least one residue that is different from (mutated from) the wt GFP. Mutations include, for instance, conservative or non-conservative amino acid substitutions, silent mutations (wherein the nucleic acid sequence is different from wild-type at a particular residue, but the amino acid sequence is not), insertions (including fusion proteins), and deletions. Myriad mutant GFPs are known, including for instance those disclosed in the following patent documents: U.S. Pat. Nos. 5,804,387; 6,090,919; 6,096,865; 6,054,321; 5,625,048; 5,874,304; 5,777,079; 5,968,750; 6,020,192; and 6,146,826; and published international patent application WO 99/64592.

Specific examples of mutant GFPs include proteins in which the fluorescence spectrum of the mutant protein is different from that of wt GFP, as well as proteins in which the fluorescence spectrum of the mutant is responsive to an environmental variable, such as temperature, proton concentration (pH), salt concentration, and redox status. A fluorescence spectrum is "responsive" to an environmental variable if the spectrum changes with changes in that variable.

Hybridization: Nucleic acid molecules that are complementary to each other hybridize by hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA or PNA target. An oligonucleotide need not be 100% complementary to its target nucleic acid sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, for example under physiological conditions in the case of in vivo assays, or under conditions in which the assays are performed.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. in *Molecular Cloning: A Laboratory Manual*, Cold Spring Harbor Laboratory Press (1989), chapters 9 and 11, herein incorporated by reference.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A composition detectable by spectroscopic, photochemical, biochemical, immunochemical, or chemical means. Typical labels include fluorescent proteins or protein tags, fluorophores, radioactive isotopes (including for instance $^{32}P$), ligands, biotin, digoxigenin, chemiluminescent agents, electron-dense reagents (such as metal sols and colloids), and enzymes (e.g., for use in an ELISA), haptens, and proteins or peptides (such as epitope tags) for which antisera or monoclonal antibodies are available. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987). A label often generates a measurable signal, such as radioactivity, fluorescent light or enzyme activity, which can be used to detect and/or quantitate the amount of labeled molecule.

Linker: A linker is a "chemical arm" between two moieties or domains in a molecule. Linkers may be used to join otherwise separate molecule moieties through a chemical reaction. The term "linker" also refers to the part of a fusion molecule between two moieties or subsections. In some embodiments, the linker in a fusion molecule, such as a fusion protein, is added by recombinant DNA techniques; in other embodiments, it is added through chemical means, such as cross-linking reactions or other in vitro chemical synthesis.

Many sorts of different chemical structures may constitute a linker (e.g., a peptide-to-peptide bond, a covalent bond between two protein domains, such as an amide, ester, or alkylamino linkages, or a single translated protein having two moieties "linked" by a series of residues). One non-limiting example of a linker is a synthetic sequence of amino acids. Other examples of linkers include streptavidin linkage, a straight or branched chain aliphatic group, particularly an alkyl group, such as $C_1$–$C_{20}$, optionally containing within the chain double bonds, triple bonds, aryl groups or heteroatoms such as N, O or S. Substituents on a diradical moiety can include $C_1$–$C_6$ alkyl, aryl, ester, ether, amine, amide, or chloro groups.

Additional types of bond combinations that may serve to link molecules are amino with carboxyl to form amide linkages, carboxy with hydroxy to form ester linkages or amino with alkyl halides to form alkylamino linkages, thiols with thiols to form disulfides, thiols with maleimides, and alkylhalides to form thioethers, for instance. Hydroxyl, carboxyl, amino and other functionalities, where not present may be introduced by known methods. Examples of specific linkers can be found, for instance, in Hennecke et al. (*Protein Eng.* 11: 405–410, 1998); and U.S. Pat. Nos. 5,767,260 and 5,856,456.

Linkers may vary in length in different embodiments, depending for instance on the molecular moieties being joined, on their method of synthesis, and on the intended function(s) of the DCTA molecule.

Linkers may be repetitive or non-repetitive. One classical repetitive peptide linker used in the production of single chain Fvs (SCFvs) is the $(Gly_4Ser)_3$ (or $(GGGGS)_3$ or $(G_4S)_3$) linker. More recently, non-repetitive linkers have been produced, and methods for the random generation of such linkers are known (Hennecke et al., *Protein Eng.* 11:405–410, 1998). In addition, linkers may be chosen to have more or less secondary character (e.g. helical character, U.S. Pat. No. 5,637,481) depending on the conformation desired in the final fusion molecule. The more secondary character a linker possesses, the more constrained the structure of the final fusion molecule will be. Therefore, substantially flexible linkers that are substantially lacking in secondary structure allow flexion of the fusion molecule at the linker.

Moiety: A part or portion of a molecule having a characteristic chemical, biochemical, structural and/or pharmacological property or function. As used herein, the term moiety refers to a subpart of a molecule (for instance, a protein) that retains an independent biochemical or structural activity from the remainder of the molecule, for instance the ability to generate a detectable signal such as fluorescence, or to bind or associate or interact with a target. A single molecule may have multiple moieties, each having an independent function.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers.

This term also encompasses DNA alterations that are present constitutionally, that alter the function of the encoded protein in a readily demonstrable manner, and that can be inherited by the children of an affected individual. In this respect, the term overlaps with "polymorphism," which generally refers to the subset of constitutional alterations.

Nucleic acid: A deoxyribonucleotide or ribonucleotide polymer in either single or double stranded form, and unless otherwise limited, encompassing known analogues of natural nucleotides that hybridize to nucleic acids in a manner similar to naturally occurring nucleotides.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA or RNA, of any length suitable for use as a probe or other indicator molecule, and that is informative about the corresponding gene.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear single-stranded polynucleotide sequence ranging in length from 2 to about 5,000 bases, for example a polynucleotide (such as DNA or RNA) which is at least 6 nucleotides, for example at least 10, 12, 15, 18, 20, 25, 50, 100, 200, 1,000, or even 5,000 nucleotides long. Oligonucleotides are often synthetic but can also be produced from naturally occurring polynucleotides.

An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Such analog molecules may also bind to or interact with polypeptides or proteins.

The terms "operatively linked" and "operably linked" refer to a juxtaposition wherein the components so described are in a relationship permitting them to function in their intended manner. For instance, a first nucleic acid sequence is operably linked with a second nucleic acid sequence when the first nucleic acid sequence is placed in a functional relationship with the second nucleic acid sequence. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of (upstream or 5' to) a protein-encoding sequence, a splicing signal for introns, maintenance of the correct reading frame of that gene to permit proper translation of mRNA, and secretion signals, and stop codons. The term "control sequences" is intended to included, at a minimum, components whose presence can influence expression, and can also include additional components whose presence is advantageous, for example, leader sequences and fusion partner sequences. Expression control sequences can include a promoter.

Open reading frame (ORF): A series of nucleotide triplets (codons) coding for amino acids without any internal termination codons. These sequences are usually translatable into a peptide.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with compositions provided herein are conventional. By way of example, Martin, in *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "pharmaceutical agent" refers to a chemical compound or composition capable of inducing a desired therapeutic or prophylactic effect when properly administered to a subject or a cell, for example when it is incubated or contacted with a cell. "Incubating" includes exposing for a sufficient amount of time for a drug to interact with a cell or cellular component, such as a protein. "Contacting" includes incubating a compound such as a drug, in solid or in liquid form, with a cell. An example of a desired effect is an anti-viral effect, which inhibits a virus from replicating or infecting cells. Similarly, an "anti-retroviral agent" is an agent that specifically inhibits a retrovirus from replicating or infecting cells.

The term "polynucleotide" or "nucleic acid sequence" refers to a polymeric form of nucleotides at least 10 bases in length. The nucleotides described herein can be ribonucleotides, deoxyribonucleotides, or modified forms of either nucleotide. The term includes single and double forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide.

The term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide, for example such a fragment which exhibits at least one useful epitope. The term "functional fragments of a polypeptide" refers to all fragments of a polypeptide that retain an activity of the polypeptide.

The term "functional fragment" of a APOBEC3G polypeptide refers to a fragment of a APOBEC3G polypeptide that retains at least one biological activity of APOBEC3G. Biological functions of APOBEC3G are discussed further herein, and include but are not limited to association with (directly or indirectly) Vif.

A functional fragment of APOBEC3G, as referred to herein in various embodiments, is a portion of the APOBEC3G protein capable of binding to Vif, a fragment capable of being degraded in a Vif-dependent manner, a fragment that has enzymatic activity, a fragment that contains a portion of the active site needed to bind substrate(s), a fragment that binds to cofactor(s) or accessory subunit(s), or a fragment capable of becoming incorporated into viral particles. Similarly, a functional fragment of Vif is, in various embodiments, a portion or domain of the Vif protein required for binding to APOBEC3G to elongins B and C, or a fragment capable of stimulating or causing degradation of APOGEC3G. Derivatives or mutant forms of APOBEC3G or Vif that retain one or more specific function(s) of the native protein could also be used to make functional fragments. These could differ from native fragments that have not been altered, but they would retain at least one of the activities useful in studying Vif function and/or Vif-dependent degradation of APOBEC3G.

Biologically functional fragments, for example, can vary in size from a polypeptide fragment as small as an epitope capable of binding an antibody molecule to a large polypeptide capable of participating in the characteristic induction or programming of phenotypic changes within a cell. The term "fragment" refers to a portion of a polypeptide which exhibits at least one useful epitope. The term "functional fragments of a polypeptide," refers to all fragments of a polypeptide that retain an activity of the polypeptide. Biologically functional fragments, for example, can vary in size from a polypeptide fragment as small as an epitope capable of binding an antibody molecule, to a large polypeptide capable of participating in the characteristic induction or programming of phenotypic changes within a cell.

Biologically functional peptides can also include fusion proteins, in which the peptide of interest has been fused to another peptide that does not substantially decrease its desired activity. An example is a GST-APOBEC3G fusion protein; another example would be a GFP-APOBEC3G fusion protein.

Probes and primers: Nucleic acid probes and primers can be readily prepared based on the nucleic acid molecules provided, as indicators of viral infection or replication, or the inhibition thereof, for instance. It is also appropriate to generate probes and primers based on fragments or portions of these nucleic acid molecules, particularly in order to distinguish between and among different alleles and haplotypes within a single gene. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as any of the sequences described herein, for example, by using computer programs intended for that purpose such as PRIMER (Version 0.5, © 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of an APOBEC3G or Vif protein encoding nucleotide will anneal to a target sequence, such as homolog of a designated APOBEC3G or Vif, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a target gene.

Also provided are isolated nucleic acid molecules that comprise specified lengths of target-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a specified nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Another mode of division, provided by way of example, is to divide a sequence, such as the sequence of APOBEC3G, based on the regions of the sequence that are relatively more or less homologous to sequences of other members of the APOBEC family. APOBEC3G has some homology to other members of the cytidine deaminase family of nucleic acid editing enzymes, especially in the two zinc-binding catalytic domains (e.g., about positions 65–100 for site 1 and 257–290 for site 2 of SEQ ID NO: 1). In addition, APOBEC3G has substantial other regions of homology, especially with APOBEC3F at the amino terminal region (e.g., about positions 1–60 of SEQ ID NO: 1) and with APOBEC3A and APOBEC3B near the carboxyl terminal end (e.g., about positions 335–383 of SEQ ID NO: 1).

The term "promoter" refers to a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

Purified: The term purified does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

RNA: A typically linear polymer of ribonucleic acid monomers, linked by phosphodiester bonds. Naturally occurring RNA molecules fall into three classes, messenger (mRNA, which encodes proteins), ribosomal (rRNA, components of ribosomes), and transfer (tRNA, molecules responsible for transferring amino acid monomers to the ribosome during protein synthesis). Total RNA refers to a heterogeneous mixture of all three types of RNA molecules.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs of a protein, and the corresponding cDNA or gene sequence, will possess a relatively high degree of sequence identity when aligned using standard methods. This homology usually will be more significant when the proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.*, 2: 482, 1981; Needleman & Wunsch *J. Mol. Biol.*, 48: 443, 1970; Pearson & Lipman *Proc. Natl. Acad. Sci. USA*, 85: 2444, 1988; Higgins & Sharp *Gene*, 73: 237–244, 1988; Higgins & Sharp *CABIOS*, 5: 151–153, 1989; Corpet et al. *Nuc. Acids Res.*, 16, 10881–90, 1988; Huang et al. *Computer Appls. in the Biosciences*, 8, 155–65, 1992; and Pearson et al. *Meth. Mol. Bio.*, 24, 307–31, 1994. Altschul et al. (*J. Mol. Biol.*, 215:403–410, 1990) presents a detailed consideration of sequence alignment methods and homology calculations.

The NCBI Basic Local Alignment Search Tool (BLAST) (Altschul et al. *J. Mol. Biol.*, 215:403–410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI BLAST Internet site. A description of how to determine sequence identity using this program is available at the NCBI BLAST help site, also on the Internet.

Homologs typically possess at least 60% sequence identity counted over full-length alignment with the amino acid sequence, using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10–20 amino acids, and may possess sequence identities of at least 85%, at least 90%, at least 95%, or even at least 98% or 99%, depending on their similarity to the reference sequence. Methods for determining sequence identity over such short windows are described at the NCBI BLAST Internet help page on the Internet.

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions, as described under "specific hybridization."

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Species compatibility (of a protein-protein interaction): In some instances, the functional interaction of two proteins is dependent on the species or strain of the sources of the two proteins. It has been noted before, for instance, that Vif functions in a species-restricted manner (Simon et al., *Embo J.*, 17:1259–1267, 1998). See also the recent paper by Mariani et al. (*Cell* 114:21–31, 2003). For example, Vif of African green monkey (SIVagm) does not have an effect in human cells, but it can neutralize the inhibitory factor in African green monkeys. Conversely, SIVagm viruses can replicate in human NP cells engineered to express the HIV-1 vif gene. The HIV Vif protein is therefore believed to neutralize an antiviral factor in nonpermissive human cells, but the HIV Vif protein would be unable to counteract the homologous antiviral factors of AGMs or of more distantly related species, such as mice. With the identification herein that Vif is interacting with APOBEC3G, it is now recognized that the interaction between Vif and APOBEC3G occurs in a species-restricted manner. This can be referred to as species compatibility of the Vif and APOBEC3G interaction.

Specific binding agent: An agent that binds substantially only to a defined target. Thus a protein-specific binding agent binds substantially only the specified protein. By way of example, as used herein, the term "X-protein specific binding agent" includes anti-X protein antibodies (and functional fragments thereof) and other agents (such as soluble receptors) that bind substantially only to the X protein (where "X" is a specified protein, or in some embodiments a specified domain or form of a protein, such as a particular allelic form of a protein).

Anti-X protein antibodies (for instance, antibodies that specifically recognize the APOBEC3G protein) may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-X protein monoclonal antibody, binds substantially only to the X protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Traditional hybridization with a target nucleic acid molecule labeled with [$^{32}$P]-dCTP is generally carried out in a solution of high ionic strength such as 6×SSC at a temperature that is 20–25° C. below the melting temperature, $T_m$, described below. For Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/µg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, *Proc. Natl. Acad. Sci. USA* 48:1390, 1962):

$$T_m = 81.5°\text{ C.} - 16.6(\log_{10}[\text{Na}^+]) + 0.41(\% \ G+C) - 0.63(\% \text{ formamide}) - (600/1)$$

where 1=the length of the hybrid in base pairs.

This equation is valid for concentrations of Na$^+$ in the range of 0.01 M to 0.4 M, and it is less accurate for calculations of Tm in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies may be made as follows: For this example, it is assumed that the filter will be washed in 0.3×SSC solution following hybridization, thereby: [Na+]= 0.045 M; % GC=45%; Formamide concentration=0; 1=150 base pairs; Tm=81.5–16.6($\log_{10}$[Na+])+(0.41×45)–(600/150); and so Tm=74.4° C.

The $T_m$ of double-stranded DNA decreases by 1–1.5° C. with every 1% decrease in homology (Bonner et al., *J. Mol. Biol.* 81:123, 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques may be utilized and that variations in experimental conditions will necessitate alternative calculations for stringency.

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25–30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids or with a known amount the target nucleic acids themselves) and referencing the hybridization intensity of unknowns with the known target nucleic acids (for example by generation of a standard curve).

Subject: Living, multicellular vertebrate organisms, a category that includes both human and veterinary subjects for example, mammals, birds and primates.

A "therapeutically effective amount" is a quantity of an agent, such as an anti-viral agent, sufficient to achieve a desired effect in a subject being treated. In one specific, non-limiting example, a therapeutically effective amount of an anti-viral agent is the amount necessary to inhibit viral replication, or to measurably alter outward signs and/or symptoms of the viral infection, for example by increasing T cell counts in the case of an HIV infection, and/or reducing cachexia or the incidence of opportunistic infections. When administered to a subject, a dosage will generally be used that will achieve target tissue concentrations (for example, in lymphocytes) that has been shown to achieve in vitro inhibition of viral replication Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

The term "Vif" refers to a viral infectivity factor (protein) encoded by lentiviruses, which affects infectivity but not production of virus particles. In the genome of naturally occurring lentiviruses, the vif gene includes an open reading frame encoding the Vif protein. This open reading frame is generally located after the open reading frame encoding pol, and overlaps the 3' end of pol. Homologues of vif exist in all lentiviruses, with the exception of equine infectious anemia virus (EIAV) (Oberste et al., *Virus Genes* 6; 95, 1992). The open reading frames (ORFs) of the different lentiviral vifs are compared in Sonigo et al., *Cell* 42; 369, 1985. The vif gene encodes a highly basic 23-Kd phosphoprotein that is synthesized in a Rev-dependent manner during the late stages of virion production.

A "virus" is a microscopic infectious agent that reproduces inside living cells. A virus consists essentially of a core of a nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. Viruses include, but are not limited to, lentiviruses such as a human immunodeficiency virus (e.g., HIV-1 and HIV-2).

"Retroviruses" are viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of retroviruses that cause slow ("lenti") diseases. The lentiviruses include human immunodeficiency virus (HIV) type 1 and type 2 (HIV-1 and HIV-2), simian immunodeficiency virus (SIV), and feline immunodeficiency virus (FIV), which are immunodeficiency viruses.

HIV is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, wherein the infection may be confirmed by antibody or western blot studies. Laboratory findings associated with this disease include a progressive decline in T-helper cells. The term "HIV disease" is a generic term that includes AIDS.

The term "wild-type" refers to the customary type of a molecule (or cell) before manipulation or mutation, or the functionally active general form. Thus, a wild-type form of a protein is the form of the protein found in a cell before manipulation or mutation, and a wild-type form of a virus is the form of a virus that infects a cell prior to manipulation or mutation.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein in a first embodiment is a method for identifying an agent that affects the ability of a lentivirus to replicate in a cell in the presence of a Vif protein or peptide. Examples of such methods involve contacting the agent to the cell under conditions sufficient to allow interaction between the cell and the agent, evaluating an amount of an APOBEC3G protein or peptide in the cell, and comparing the amount of the APOBEC3G protein or peptide in the cell contacted with the agent to an amount of APOBEC3G protein or peptide in a control cell not treated with the agent, wherein a statistically significant difference in the amount of the APOBEC3G protein or peptide in the cell contacted with the agent, as compared to the control cell not treated with the agent, identifies the agent as one that affects the ability of a lentivirus to replicate in a cell. Optionally, Vif is expressed in the cell, for instance, from a vector or a lentiviral vector. Optionally, the Vif is a fusion protein.

In certain of the provided methods, the Vif protein or peptide and the APOBEC3G protein or peptide are species compatible or derived from compatible species.

Cells as used in the provided methods may be, but need not be, cells in cell culture. Specific contemplated cells include, but are not limited to, a vertebrate cell (such as, for instance, a mammalian cell), an insect cell, or a fungal cell (such as, for instance, a yeast cell). Optionally, the cell is infected with a lentivirus.

In additional embodiments of the provided methods, the lentivirus is HIV-1, HIV-2, SIV, FIV or another lentivirus that contains a Vif gene. For instance, in specific contemplated methods the lentivirus is HIV-1 or HIV-2.

Also provided are methods for identifying an agent that affects the ability of a lentivirus to replicate in a cell in the presence of a Vif protein or peptide, wherein an increase in the amount of APOBEC3G as compared to the control identifies the agent as one that inhibits lentiviral replication.

Optionally, in certain methods evaluating the amount of APOBEC3G in the cell involves using a high throughput technique.

In some example methods, evaluating the amount of APOBEC3G in the cell comprises detecting labeled APOBEC3G. For instance and in some of the provided methods, the labeled APOBEC3G is labeled with one or more of the following: a fluorophore, a chemiluminescent agent, a radioisotope, an epitope tag, an enzyme, a ligand, a metal sol, or a colloid. Optionally, the labeled APOBEC3G is a fusion construct, containing all or part of the APOBEC3G protein and an otherwise detectable protein or peptide fragment, which is itself susceptible to degradation via the Vif-mediated degradation pathway.

It is particularly contemplated in specific example methods that affecting lentiviral replication involves at least one (or more) of the following: interfering with an interaction between Vif and APOBEC3G; interfering with Vif production prior to its interaction with APOBEC3G; interfering with targeting of Vif-associated APOBEC3G to a proteasome; and/or interfering with proteasomal degradation of Vif-associated APOBEC3G.

Yet another embodiment provides a method for identifying an agent that inhibits Vif-mediated degradation of APOBEC3G in a cell, which method involves contacting a cell which expresses Vif and APOBEC3G with a test agent under conditions sufficient to allow interaction between the cell and the agent; and determining whether the Vif-mediated degradation of APOBEC3G is inhibited. Optionally, in such methods, determining whether the Vif-mediated degradation of APOBEC3G is inhibited involves determining whether there is a statistically significant decrease in the interaction of Vif and APOBEC3G in the cell contacted with the test agent as compared to the interaction of Vif and APOBEC3G in a control cell not exposed to the test agent.

In examples of these methods, the agent may include, for instance, a peptide or peptidomimetic, a non-peptide compound, a polypeptide fragment or derivative of Vif, and/or a polypeptide fragment or derivative of APOBEC3G.

It is contemplated that in specific methods, inhibiting Vif-mediated degradation of APOBEC3G in a cell involves at least one of the following: interfering with an interaction between Vif and APOBEC3G; interfering with Vif production prior to its interaction with APOBEC3G; interfering with targeting of Vif-associated APOBEC3G to a proteasome; or interfering with proteasomal degradation of Vif-associated APOBEC3G.

Another embodiment provides for the use of an agent that interferes with Vif-mediated degradation of APOBEC3G in the manufacture of a medicament for the treatment of lentivirus infection. Also provided is use of an agent that interferes with Vif-mediated degradation of APOBEC3G in the manufacture of a medicament for the treatment of lentivirus infection, wherein the agent is identified using any one of the methods described herein.

Method of making a composition that inhibits the interaction of APOBEC3G and Vif are also provided, which methods involve incorporating an agent that inhibits Vif-mediated degradation of APOBEC3G in a pharmaceutically acceptable carrier. Also provided are methods of making a composition that inhibits the interaction of APOBEC3G and Vif, comprising incorporating an agent that inhibits Vif-mediated degradation of APOBEC3G in a pharmaceutically acceptable carrier, wherein the agent is identified using any one of the methods described herein.

Yet another embodiment is a method of inhibiting replication of a lentivirus (such as HIV, SIV, FIV or another lentivirus that contains a Vif gene) in a non-permissive (NP) cell, comprising interfering with Vif-mediated degradation of APOBEC3G in the cell. It is contemplated that, in examples of such methods, interfering with Vif-mediated degradation of APOBEC3G in a cell involves at least one of the following: interfering with an interaction between Vif and APOBEC3G; interfering with Vif production prior to its interaction with APOBEC3G; interfering with targeting of Vif-associated APOBEC3G to a proteasome; or interfering with proteasomal degradation of Vif-associated APOBEC3G.

Optionally, the method involves interfering with an interaction (directly or indirectly) between Vif and APOBEC3G. Such interaction optionally occurs in a subject, and is interfered with in a subject, particularly a subject that is infected with, or is at risk of being infected with, an immunodeficiency virus. In examples of such methods, interfering with the interaction of Vif and APOBEC3G includes administering to the subject a therapeutically effective amount of a peptide agent or non-peptide compound agent that inhibits an interaction between Vif and APOBEC3G.

It is contemplated that, in any of the provided methods, the interaction between Vif and APOBEC3G may optionally be mediated by or influenced by at least one additional protein or factor.

Yet another embodiment is a method for preventing or inhibiting replication of a lentivirus in a cell, which method involves transferring a nucleic acid comprising a promoter operably linked to a nucleic acid sequence encoding APOBEC3G or an effective fragment or derivative thereof into the cell, wherein the transfer of the nucleic acid results in the expression of APOBEC3G and the inhibition of lentiviral replication. Optionally, the promoter is an inducible promoter or a constitutive promoter. It is contemplated that the lentivirus is, in examples of such methods, HIV-1, HIV-2, SIV, FIV or another lentivirus that contains a Vif gene. In particular examples, the lentivirus is a human lentivirus.

Also provided herein are specific fusion molecules, both nucleic acid and protein, that include part or all of APOBEC3G and one or more additional peptides or domains that serve as a label or other agent capable of ready detection. Representative examples of such molecules include the nucleic acid molecules shown in SEQ ID NOs: 1, 3, and 5, and proteins shown in SEQ ID NOs: 2, 4, and 6.

IV. Vif-Mediated Degradation of APOBEC3G

The viral infectivity factor (Vif) encoded by human immunodeficiency virus (HIV-1) neutralizes a potent antiviral pathway that occurs in human T lymphocytes and in several leukemic T cell lines that are termed nonpermissive, but is not present in other cells. In the absence of Vif, this antiviral pathway efficiently destroys HIV-1. Recently, it was reported that APOBEC3G (also known as CEM-15), a cytidine deaminase nucleic acid editing enzyme, confers this antiviral phenotype on permissive cells. Here, evidence is described showing that Vif binds to APOBEC3G and induces its rapid degradation, thus eliminating it from cells and preventing its incorporation into HIV-1 virions. Studies of Vif mutants imply that this protein contains two domains, one that binds APOBEC3G and another, containing a conserved SLQ(Y/F)LA motif, that mediates APOBEC3G degradation by a proteasome-dependent pathway. Certain of these results have also been reported in Marin et al. (*Nature Med.* 9(11):1398–1403, November 2003), which is incorporated herein by reference in its entirety.

As shown in FIG. 2A, the SLQ(Y/F)LAΦΦΦΦ motif in lentiviral Vif proteins is strikingly similar to the most conserved sequence in the BC-box regions of the suppressors of cytokine signaling (SOCS) proteins. This similarity includes the location of the motifs in the carboxyl terminal domains of the proteins as well as a less conserved downstream proline-containing LPLP consensus sequence (Kile et al. *Trends Biochem Sci* 27, 235–241, 2002). Numerous BC-box proteins are known, including the von Hippel Lindau tumor suppressor (VHL) (Iwai et al. *Proc Natl Acad Sci USA* 96, 12436–12441, 1999; van & Kaelin, *Curr Opin Genet Dev* 11, 27–34, 2001). As illustrated in FIG. 2B, BC-box proteins function as assembly platforms to link proteins being targeted for rapid degradation to a multisubunit E3 Ub-protein isopeptide ligase that contains elongins B and C, a member of the cullin family, and Rbx-1. In this degradation pathway (Glickman & Ciechanover, *Physiol Rev* 82, 373–428, 2002; Pickart, *Annu Rev Biochem* 70, 503–533, 2001), an E1 activating enzyme transfers Ub to an E2 Ub conjugating enzyme. The E2-Ub then associates with the catalytic core (composed of cullin and Rbx-1) of the E3 ligase to covalently link the Ub onto a lysine side chain of the target protein. Transfer of multiple Ub moieties results in a polyubiquitinated protein that is transferred to proteasomes for degradation (Pickart, *Annu Rev Biochem* 70, 503–533, 2001). In agreement with the hypothesis that Vif is a BC-box protein, mutations of its SLQ(Y/F)LAΦΦΦΦ motif have no effect on binding to APOBEC3G but eliminate APOBEC3G degradation (Marin et al., *Nat Med* 9, 1398–1403, 2003; Yu et al. *Science* 302, 1056–1060, 2003). Moreover, small amounts of Vif appear to be capable of degrading large quantities of APOBEC3G (Kao, et al., *J Virol* 77, 11398–11407, 2003; Marin et al., *Nat Med* 9, 1398–1403, 2003; Sheehy et al., *Nat Med* 9, 1404–1407, 2003; Mehle et al., *J Biol Chem.* 279(9):7792–7798, 2004.).

Striking independent support for this mechanism of Vif function was recently described by Yu et al., who reported that Vif associates specifically with elongins B and C and with Cul5 and Rbx-1, as well as with APOBEC3G (Yu et al., *Science* 302, 1056–1060, 2003). Moreover, a SLQ-to-AAA mutation in the Vif BC-box consensus site caused dissociation of elongins B and C and Cul5 from the complex. Most significantly, dominant-negative mutants of Cul5 that were either incapable of being modified by the Ub-like small modifier Nedd8 or of associating with Rbx-1 prevented the degradation of APOBEC3G and restored its incorporation into progeny virions and its antiviral activity (Yu et al., *Science* 302, 1056–1060, 2003). This indicates that Vif's ability to induce degradation of APOBEC3G is necessary and sufficient to exclude APOBEC3G from virions and to neutralize its antiviral activity.

Cells contain different families of multisubunit E3 Ub-protein isopeptide ligases in addition to the BC-box family. A large family is the SCF group, in which an F-box protein binds to the target protein and links it to a complex that contains Skp-1 and a cullin (see FIG. 2C) (Kile et al., *Trends Biochem Sci* 27, 235–241, 2002). The HIV-1 Vpu protein recruits an SCF complex to specifically degrade CD4 (Margottin et al., *Mol Cell* 1, 565–574, 1998), which enhances release of progeny HIV-1 virions from the cell surfaces (Bour & Strebel, *Microbes Infect* 5, 1029–1039, 2003). BC-box and F-box sequences are unrelated and they exclusively recruit either elongins B plus C or Skp-1, respectively (Kile et al., *Trends Biochem Sci* 27, 235–241, 2002), but they are believed to have similar folded structures (VanDemark & Hill, *Curr Opin Struct Biol* 12, 822–830, 2002). Although the multisubunit E3 ligase complex assembled by Vif was recently described as "SCF-like" (Yu et al., *Science* 302, 1056–1060, 2003), Vif is clearly a BC-box protein.

V. Applications of the Vif-APOBEC3G Interaction and Degradation of APOBEC3G

Knowledge of the mechanism by which Vif counteracts APOBEC3G has revealed promising new targets and assays for drug development. HIV-1 and other lentiviruses have a high inherent rate of mutation, which enables escape from the immune system, adaptation to diverse tissue niches, and expansion of the coreceptor repertoire (Balzarini et al., *J Virol* 75, 5772–5777, 2001). This inherent variability is clearly advantageous for HIV-1, which is believed to operate near the threshold for error catastrophe beyond which its survival would become impossible (Janini et al., *J Virol* 75, 7973–7986, 2001). Consequently, a compound such as a drug that interferes even slightly with the Vif-mediated degradation of APOBEC3G might be very useful for increasing the mutation frequency and reducing viral fitness.

In evaluating potential drug targets it is prudent to consider the critical role of proteasomes in removing damaged and misfolded proteins as well as in regulating the cell cycle and apoptosis. Disruption of normal proteasome-mediated degradation pathways leads to numerous diseases including neurodegenerative disorders and cancer. Nevertheless, general proteasome inhibitors have provided effective therapies for cancer, without the pleiotropic effects that might be expected (Adams, *Cancer Treat Rev* 29 Suppl 1, 3–9, 2003). Therefore, inhibition of proteasomes might be beneficial.

In principle, the most efficient strategy would employ a small molecule inhibitor that could selectively disrupt association of Vif and APOBEC3G. Although interfering with protein-protein interactions is often difficult to achieve, the CCR5 inhibitors TAK779 and SHC351125 work by this mechanism to block binding of HIV-1 gp120 (Baba et al., *Proc Natl Acad Sci USA* 96, 5698–5703, 1999; Strizki et al., *Proc Natl Acad Sci USA* 98, 12718–12723, 2001). Compounds that prevent MDM2-mediated polyubiquitination and degradation of p53 by blocking their association have recently been developed (see: the internet publication at sciencemag.org/cgi/content/abstract/1092472). Other levels of intervention in the Ub-dependent proteasome-mediated degradation pathway also offer a varied degree of specificity for APOBEC3G degradation. Targets upstream of the proteasome, which include E1 and E2 Ub-conjugating enzymes, have been well studied and the wealth of information on their structure and enzymatic function could direct the design of effective inhibitory agents. In particular, there are numerous E2 enzymes (~50 identified to date) that interact with specific E3 ligases to contribute to target specificity, but factors determining this specificity are poorly understood (Pray et al., *Drug Resist Updat* 5, 249–258; 2002; Nalepa & Wade Harper, *Cancer Treat Rev* 29 Suppl 1, 49–57, 2003).

Additionally, the E3 ligase components elongins B and C, Cul5, and Rbx-1 that associate with Vif present multiple points of intervention. Cul5 belongs to a family of proteins that are covalently modified by the Ub-like protein NEDD8.

Neddylation, which is critical for cullin recruitment of the E2-Ub enzyme to the E3 ligase, occurs by an enzymatic cascade similar to that of ubiquitination, thus providing additional potential targets for inhibition (Ohh et al., *EMBO Rep* 3, 177–182, 2002). A compound that eliminated interaction of the BC-box of Vif with the E3 ligase would also be expected to restore APOBEC3G antiviral activity. An additional benefit of these discoveries and methods is that any drugs for these pathways may have potential uses in investigation or treatment of other diseases in which proteasome functions are implicated.

Thus, with the surprising discovery that Vif binds to APOBEC3G and mediates the rapid degradation of APOBEC3G, methods are now enabled for screening for agents that influence (for instance, inhibit) this pathway. Such agents, and particularly agents that inhibit Vif-mediated degradation of APOBEC3G, can be used, for instance, to inhibit lentiviral infection or replication in a cellular system. Similarly, agents that inhibit the binding of Vif to APOBEC3G also are predicted to be able to inhibit the degradation of APOBEC3G within cells and in animals.

In particular, methods are provided for rapidly screening in a cell based system for such agents by exploiting labeled or otherwise detectable APOBEC3G, since an agent that inhibits one or more steps in the degradation pathway can be identified by the increased presence of APOBEC3G when the system is incubated with the candidate agent.

In a further screening approach, methods are described for measuring APOBEC3G binding to Vif in a cell-free system. Agents that inhibit this binding would also be potentially useful for inhibiting lentiviral replication in cells and animals. Alternatively, it is contemplated that yeast cells could be used to detect the binding of APOBEC3G with Vif, for example by using a two-hybrid assay. Similarly, bacterial cells developed to monitor protein-protein interactions could also be used. In these cases, agents could be screened for their abilities to disrupt these associations within the yeast or bacterial cells.

It is specifically contemplated that Vif may not interact directly with APOBEC3G in order to mediate its degradation. Thus, the terms "interact" and "interaction" and "binding" as used herein include both situations where there is a direct interaction between Vif and APOBEC3G, and where the interaction is mediated or influenced positively or negatively by one or more other molecules, for instance, other proteins that act in the degradation pathways, or that bind to APOBEC3G in cells and influence its subcellular localization, or that covalently modify APOBEC3G or Vif in cells and thereby alter their association. It is one benefit of the screening methods provided herein, and particularly cell-based methods, that it does not matter whether the interaction between Vif and APOBEC3G is direct or indirect; the provided screening systems will identify agents that disrupt the interaction based on the observed phenotypic effect of accumulation of (or loss of) APOBEC3G. It is currently believed that the binding between Vif and APOBEC3G is direct, although it might be modified and/or controlled by post-translational modifications and/or by other cellular factors.

Representative assays for the cell-based approach utilize cells, particularly mammalian cells, that co-express Vif and APOBEC3G, or detectable or otherwise modified versions of these proteins. The Vif derivative used will usually retain its ability to bind to (directly or indirectly) the APOBEC3G derivative and to induce its degradation. The APOBEC3G derivative will in most such embodiments retain its ability to bind to Vif and to be degraded as a consequence. It is not necessary that cells of the screening system be infected with a lentivirus.

In a first contemplated cell-based screening assay, using non-infected cells, an expression vector comprising a sequence encoding a visually (or otherwise) detectable APOBEC3G fusion protein (such as EGFP-ApoBec3G or YFP-APOBEC3G or APOBEC3G-luciferase) is transfected or transduced or otherwise introduced into a (mammalian) cell. Also in that same cell along with the visually (or otherwise) detectable APOBEC3G fusion protein is a second expression vector, comprising a sequence encoding the HIV-1 Vif gene product or an active derivative or fragment thereof, such that a Vif is also expressed in the cell. Upon co-expression, it is expected that the level of APOBEC3G will be relatively low; this is readily determined, based on the detectability of the APOBEC3G fusion protein. These doubly transformed cells are grown, for instance in sterile culture plates (such as multi-well plates), and test compounds are incubated within the various culture wells for a period of time. Preferably the period of time is sufficiently long for newly synthesized APOBEC3G fusion protein to accumulate, if the test compound inhibits the Vif-mediated APOBEC3G degradation pathway. An appropriate positive control compound is an inhibitor of the ubiquitin tagging/processing system (the proteasomal degradation pathway). An appropriate negative control is a labeled protein such as beta-galactosidase, which is not degraded by Vif.

After the period of time (which may be varied), the cell cultures are assayed to determine the amount of APOBEC3G, for instance in comparison to the amount detectable in an equivalent cell line not incubated with the compound, or incubated with a different compound. In certain embodiments, the cells can be assayed directly in the culture plates, which enables automated assay systems.

It is expected that those cells that were contacted with a compound that (1) effectively disrupts the Vif-mediated APOBEC3G degradation pathway and (2) was not toxic the cells, will contain, upon examination, new detectable APOBEC3G. Such compounds are good candidates for therapeutic compounds, useful in the inhibition of lentiviral infection or replication. If the cells do not accumulate APOBEC3G, or in other words, if no detectable APOBEC3G is observed, this indicates that the compound contacted with that cell culture either (1) was toxic to the cell, or (2) did not sufficiently inhibit the targeted degradation pathway. Such compounds are not necessarily good lead compounds for further investigation.

It is believed that such assays will identify agents that influence, and more particularly inhibit, Vif-mediated degradation of APOBEC3G at any stage of the pathway, including but not limited to the interaction of Vif with a necessary component of the pathway, the interaction of APOBEC3G with a necessary component of the pathway, the targeting of APOBEC3G to degradative systems within the cell (such as the proteasome), the function of such degradative system(s), and so forth.

It is believed that any cells that contain proteasomes (and therefore are capable of degrading proteins via the proteasomes) can be used in the cell-based assays described, including for instance avian cells, insect cells, or yeast cells, as these may be capable of degrading APOBEC3G in a manner stimulated by Vif. If additional cellular factors from mammalian cells are needed for the Vif-dependent degradation of APOBEC3G, these factors could be engineered into the cells.

It is also conceived that yeast or bacterial cells could mediate the Vif-dependent degradation of APOBEC3G. They could also be used to screen for Vif-APOBEC3G association/degradation by approaches such as the two-hybrid screening methods. Such methods would not work if the Vif construct used caused complete degradation of APOBEC3G, but one could use a fragment of Vif that binds to APOBEC3G but lacks sequences required for degradation, such as the conserved SLQ(Y/F)LA motif that is needed for the degradation but not for the binding.

In one embodiment, the vector for Vif is a lentiviral vector, in which case the Vif expression will depend on other requirements such as the viral Tat and Rev proteins. In that case, any agent that interferes with Vif expression (including agents that inhibit Tat or Rev or the viral promoter) will result in increased expression/maintenance of APOBEC3G, which would be detected by the assay. Thus, in this embodiment, the provided screen would be able to detect agents that interfere with lentiviral replication at multiple levels.

In another assay embodiment that employs cells, the cells are used to detect association of Vif with APOBEC3G, rather than degradation per se. These assays employ approaches such as the yeast two-hybrid method, in which case the growth of the cells or their production of measurable compounds can be made to depend on the Vif-APOBEC3G association; such systems are known in the art. Agents that disrupt the association between Vif and APOBEC3G, as identified in these methods, would be potentially useful for inhibiting lentiviral replication in mammalian cells or in animals, and could be tested further.

In yet another embodiment, the association of Vif with APOBEC3G (or suitable derivatives of these proteins) would be analyzed in a cell-free system. In such systems, the association can be monitored by standard binding assays such as ELISA assays or other methods known to those of skill in the art. Agents that are identified in such screens as capable of disrupting this association would potentially be useful for inhibiting lentiviral replication in mammalian cells or in animals, and can be tested further for this property.

In another embodiment, only the Vif catalytic fragment is expressed, rather than the entire Vif protein. Such assays can be used to more specifically screen for agents that block APOBEC3G degradation by blocking Vif catalytic ubiquitination signals. In various embodiments described herein, it would not be necessary to express or use the entire Vif or APOBEC3G proteins. Active fragments, derivatives or mutant versions could be employed. For instance, the provided binding assays, including those involving yeast two-hybrid methods, would for example only require domains of these proteins needed for their association.

VI. Marked/Labeled/Detectable APOBEC3G Proteins

The current disclosure provides APOBEC3G fusion proteins that can be used in screening procedures, in order to readily identify agents that influence Vif-mediated degradation of APOBEC3G. Such agents are potential lead compounds for use in the inhibition of lentiviral replication and/or infectivity. Representative provided screening methods employ a labeled or marked APOBEC3G protein, for instance, that is detectable in the system. Easy and reliable detection of the APOBEC3G protein enables rapid identification of agents that inhibit its Vif-dependent degradation.

It is contemplated that the APOBEC3G protein(s) used in the described procedures can be labeled chemically, for instance by cross-linking and the like. Cross-linkers are well known, and examples of molecules used for cross-linking can be found, for instance, in U.S. Pat. No. 6,027,890 ("Methods and compositions for enhancing sensitivity in the analysis of biological-based assays") and Hermanson, *Bioconjugate Techniques*, (Academic Press, San Diego, Calif., 1996). Additional chemical methods for labeling proteins are known to those of ordinary skill in the art.

In preferred embodiments, it is contemplated that the APOBEC3G protein is detectable due to its fusion (usually through genetic engineering techniques) to a readily detectable peptide or polypeptide element. Non-limiting examples of readily detectable peptide or polypeptide elements include peptide tags or fluorescent proteins.

However the detectable moiety is attached or linked to the APOBEC3G, it is preferred that the detectable APOBEC3G used in provided methods be of a nature that is readily degradable by the pathway(s) responsible for Vif-dependent degradation of native APOBEC3G (for instance, substantially polypeptide), as this permits the easy identification of agents that influence that pathway through the detection of retained (or lost) labeled APOBEC3G from a system. If the detectable moiety or agent were not degraded by the pathway, it would be more difficult to distinguish those agents that were blocking (versus not blocking) the degradation of APOBEC3G.

With the provision herein of detectable APOBEC3G proteins, and the description of specific APOBEC3G fusion proteins, the construction of other detectable APOBEC3G proteins that maintain sufficient native bio-activity to be used in the provided screen procedures is now enabled. The construction and use of representative APOBEC3G fusion molecules is described herein.

VII. Selection of APOBEC3G Fusion Components

APOBEC3G: It is contemplated that in some embodiments, all or substantially all of the APOBEC3G protein will be incorporated into the fusion protein. Shorter segments of APOBEC3G can in some cases be used. The choice of appropriate APOBEC3G protein domains and/or peptides for incorporation into the fusion proteins will be dictated by the need to include a sufficient portion of the protein in order that it should still be subject to Vif-mediated degradation in the assay system.

Fragments of APOBEC3G or of related targets that are degraded in a Vif-dependent manner would be suitable, as would derivatives of APOBEC3G that are subject to this degradation. The only known requirement for this degradation would be a portion of APOBEC3G that binds to Vif and that contains at least one lysine residue that serves as a target site for Vif-dependent polyubiquitination. In this regard, a fragment of APOBEC3G containing residues 54–124 has been reported to associate with Vif (Conticello et al., *Curr. Biol.* 13:2009–2013, 2003).

Selection of a label/detectable peptide portion for a fusion protein of the current disclosure will depend on the assay in which the fusion is intended to be used, as well as the facilities and such available to the practitioner construction the fusion and carrying out the assay(s). Detectable peptide portions can be short peptides (such as tags), or longer peptide molecules or protein domains or proteins (such as fluorescent or otherwise detectable proteins). Merely by way of example, functionalizing peptide tags that can be used in fusions according to this disclosure include epitope tags (such as myc, T7, GST, HA, or FLAG), translocation/transduction tags (such as Tat), purification tags (such as the hexa-histidine tag) and peptide labels, such as green fluorescent protein (GFP) and aequorin. An epitope tag can be added to a APOBEC3G fusion protein in order to allow the resultant fusion protein to be identified through the use of an antibody that recognizes the epitope. A purification tag can be added to a APOBEC3G fusion protein in order to allow the resultant fusion protein to be purified, for instance through column chromatography. Directly detectable moieties, such as fluorescent proteins (such as GFP or YFP, and proteins derived therefrom) provide the added benefit of being directly detectable.

The choice of appropriate linker, if any linker is used to facilitate the joining of domains within the fusion protein, also will be influenced by the selected portions of the molecule, and whether these portions can or must interact or should or can be held apart from each other. In general, a linker used in an APOBEC3G fusion will be of a length and secondary character sufficient to permit the detectable portion of the fusion protein to perform its function without hindering the required activity of the APOBEC3G portion. Linkers can be a simple as a few amino acids that are included to facilitate construction of the fusion, for instance by the addition of one or more restriction endonuclease sites in the corresponding recombinant nucleic acid fusion molecule.

VII. Assembly of APOBEC3G Fusion Proteins

The construction of fusion proteins from domains of known proteins, or from whole proteins or proteins and peptides, is well known. In general, a nucleic acid molecule that encodes the desired protein and/or peptide portions are joined using genetic engineering techniques to create a single, operably linked fusion oligonucleotide. Appropriate molecular biological techniques may be found in Sambrook et al. (1989). Examples of genetically engineered multi-domain proteins, including those joined by various linkers, and those containing peptide tags, can be found in the following patent documents:

U.S. Pat. No. 5,994,104 ("Interleukin-12 fusion protein");

U.S. Pat. No. 5,981,177 ("Protein fusion method and construction");

U.S. Pat. No. 5,914,254 ("Expression of fusion polypeptides transported out of the cytoplasm without leader sequences");

U.S. Pat. No. 5,856,456 ("Linker for linked fusion polypeptides");

U.S. Pat. No. 5,767,260 ("Antigen-binding fusion proteins");

U.S. Pat. No. 5,696,237 ("Recombinant antibody-toxin fusion protein");

U.S. Pat. No. 5,587,455 ("Cytotoxic agent against specific virus infection");

U.S. Pat. No. 4,851,341 ("Immunoaffinity purification system");

U.S. Pat. No. 4,703,004 ("Synthesis of protein with an identification peptide"); and WO 98/36087 ("Immunological tolerance to HIV epitopes").

In particular, patent disclosures related to fusion proteins containing a GFP moiety include the following:

U.S. Pat. No. 6,180,343 ("Green fluorescent protein fusions with random peptides");

WO 99/54348 ("Rapidly degrading GFP-fusion proteins and methods of use");

WO 99/19470 ("GFP-annexin fusion proteins")

WO 98/14605 ("Renilla luciferase and green fluorescent protein fusion genes"); and EP 949269 ("Biosensor protein").

The placement of the marker peptide portion within the subject APOBEC3G fusion proteins is influenced by the activity of the marker peptide portion and the need to maintain at least sufficient APOBEC3G biological activity in the fusion in order to mediate its involvement in the Vif-mediated degradation pathway. Thus, fusion proteins should be tested in a control system before being used in screening procedures, to ensure that the specific fusion protein is effectively subject to degradation by the pathway in the absence of any test agents.

It is believed that any location within the protein could be used. By way of examples, attachments at the amino terminus are suitable (e.g., as shown in YFP-APOBEC3G; SEQ ID NOs: 3 and 4). Similarly, the carboxyl terminus is also suitable, for instance as shown in the APOBEC3G-luciferase fusion protein (SEQ ID NOs: 5 and 6), which also can be efficiently degraded by Vif). Thus, a proven aspect of this application is that multiple different labeled derivatives of APOBEC3G are feasible and that this cell-based assay system works.

IX. Expression of Nucleic Acid Molecules and Polypeptides

The expression and purification of proteins, such as an APOBEC3G protein or fusion protein, can be performed using standard laboratory techniques. Examples of such methods are discussed or referenced herein. After expression, purified protein have many uses, including for instance functional analyses, antibody production, diagnostics, and patient therapy. Furthermore, the DNA sequences of APOBEC3G and fusion cDNAs can be manipulated in studies to understand the expression of the gene and the function of its product. Variant or allelic forms of APOBEC3G may be isolated based upon information contained herein, and may be studied in order to detect alteration in expression patterns in terms of relative quantities, tissue specificity and functional properties of the encoded APOBEC3G variant protein (e.g., influence on viral infectivity). Partial or full-length cDNA sequences, which encode for the subject protein or fusion protein, may be ligated into bacterial expression vectors. Methods for expressing large amounts of protein from a cloned sequence introduced into *Escherichia coli* (*E. coli*) or baculovirus/Sf9 cells may be utilized for the purification, localization and functional analysis of proteins. For example, fusion proteins consisting of peptides encoded by a portion of a gene native to the cell in which the protein is expressed (e.g., a *E. coli* lacZ or trpE gene for bacterial expression) linked to a APOBEC3G protein or domain or fragment thereof may be used in various procedures, for instance to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence. In addition, fusion proteins (for instance, proteins that contain an indicator molecule, such as a protein or peptide, linked to a APOBEC3G protein or domain or fragment thereof) can be used in methods described herein, for screening for compounds that inhibit or interfere with lentiviral infection.

Intact native APOBEC3G protein may also be produced in large amounts for functional studies. Methods and plasmid vectors for producing fusion proteins and intact native proteins in culture are well known in the art, and specific methods are described in Sambrook et al. (In *Molecular Cloning: A Laboratory Manual*, Ch. 17, CSHL, New York, 1989). Such fusion proteins may be made in large amounts, are easy to purify, and can be used for instance to elicit antibody response, or for functional assays or as therapeutic molecules. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989).

Proteins, including fusion proteins, may be isolated from protein gels, lyophilized, ground into a powder and used as an antigen.

Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986).

The DNA sequence can also be transferred from its existing context to other cloning vehicles, such as other plasmids, bacteriophages, cosmids, animal viruses and yeast artificial chromosomes (YACs) (Burke et al., *Science* 236: 806–812, 1987). These vectors may then be introduced into a variety of hosts including somatic cells, and simple or complex organisms, such as bacteria, fungi (Timberlake and Marshall, *Science* 244:1313–1317, 1989), invertebrates, plants (Gasser and Fraley, *Science* 244:1293, 1989), and animals (Pursel et al., *Science* 244:1281–1288, 1989), which cell or organisms are rendered transgenic by the introduction of the heterologous cDNA.

For expression in mammalian cells, a cDNA sequence may be ligated to heterologous promoters, such as the simian virus (SV) 40 promoter in the pSV2 vector (Mulligan and Berg, *Proc. Natl. Acad. Sci. USA* 78:2072–2076, 1981), and introduced into cells, such as monkey COS-1 cells (Gluzman, *Cell* 23:175–182, 1981), to achieve transient or long-term expression. The stable integration of the chimeric gene construct may be maintained in mammalian cells by biochemical selection, such as neomycin (Southern and Berg, *J. Mol. Appl. Genet.* 1:327–341, 1982) and mycophenolic acid (Mulligan and Berg, *Proc. Natl. Acad. Sci. USA* 78:2072–2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

A cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078–2076, 1981; Gorman et al., *Proc. Natl. Acad. Sci USA* 78:6777–6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319–328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072–2076, 1981) or neo (Southern and Berg, *J. Mol. Appl. Genet.* 1:327–341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163–2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Protein, such as fusion protein, encoding sequences can also be delivered to target cells in vitro via non-infectious systems, for instance liposomes.

These eukaryotic expression systems can be used for studies of APOBEC3G and APOBEC3G fusion protein encoding nucleic acids and mutant forms of these molecules, including variant proteins and mutant forms of these proteins. The eukaryotic expression systems may also be used to study the function of the normal complete protein, specific portions of the protein, or of naturally occurring or artificially produced mutant proteins.

Using the above techniques, the expression vectors containing a APOBEC3G or APOBEC3G fusion encoding sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175–182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the APOBEC3G gene or cDNA sequences, for expression in a suitable host, either alone or as a fusion protein, such as a labeled or otherwise detectable fusion protein. The DNA is operatively linked in the vector to an expression control sequence in the recombinant DNA molecule so that a APOBEC3G polypeptide or fusion polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other *bacilli*; other bacteria; yeast; fungi; insect; mouse or other animal; plant hosts; or human tissue cells.

It is appreciated that for mutant or variant APOBEC3G DNA sequences, similar systems are employed to express and produce the mutant product. In addition, fragments of a APOBEC3G protein can be expressed essentially as detailed above, as can fusion proteins comprising all of APOBEC3G or a fragment or fragments thereof. Such fragments include individual APOBEC3G protein domains or sub-domains, as well as shorter fragments such as peptides. APOBEC3G protein fragments having therapeutic one or more properties may be expressed in this manner also, including for instance substantially soluble fragments, or fragments that associate with Vif directly or indirectly.

X. Purification

In some embodiments, it is beneficial to obtain isolated and purified APOBEC3G fusion protein, for instance for use in cell free in vitro screening tests. One skilled in the art will understand that there are myriad ways to purify recombinant polypeptides, and such typical methods of protein purification may be used to purify the disclosed APOBEC3G fusion proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification (e.g., in addition to another functionalizing portion of the fusion, such as a targeting domain or another tag, or a fluorescent protein, peptide, or other marker). A specific proteolytic site, for instance a thrombin-specific digestion site, can be engineered into the protein between the tag and the remainder of the fusion to facilitate removal of the tag after purification, if such removal is desired.

Commercially produced protein expression/purification kits provide tailored protocols for the purification of proteins made using each system. See, for instance, the QIAexpress™ expression system from QIAGEN (Chatsworth, Calif.) and various expression systems provided by INVITROGEN (Carlsbad, Calif.). Where a commercial kit is employed to produce an APOBEC3G fusion protein, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (The QIAexpressionist, QIAGEN, 1997).

More generally, the binding specificities of either the APOBEC3G or marker peptide domain, or both, of a disclosed fusion protein may be exploited to facilitate specific purification of the proteins. One example method of performing such specific purification would be column chromatography using column resin to which the target molecule, or an appropriate epitope or fragment or domain of the target molecule, has been attached.

In addition to protein expression and purification guidelines provided herein, protein expression/purification kits are produced commercially. See, for instance, the QIAexpress™ expression system from QIAGEN (Chatsworth, Calif.) and various expression systems provided by INVITROGEN (Carlsbad, Calif.). Depending on the details provided by the manufactures, such kits can be used for production and purification of APOBEC3G fusion proteins.

XI. Generation of Variant and Fragment APOBEC3G Polypeptides

Certain functional characteristics of the proteins and fusion proteins disclosed herein lie not in the precise amino acid sequence of the proteins, but rather in the three-dimensional structure inherent in the amino acid sequences encoded by the DNA sequences. It is possible to recreate the functional characteristics of the fusion proteins or protein domains by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a detectable APOBEC3G fusion protein useful in the assays described. Such substitutions, however, may not produce functional variants of the disclosed fusion proteins if the substitutions are made at essential amino acid positions, for instance, binding-specificity essential residues within APOBEC3G, amino acids necessary for the detection (for instance, fluorescence) of the detectable moiety, and so forth. Thus, it is useful to assay the activity of variant fusion proteins (or the appropriate portion of the variant fusion proteins) using available protocols, including for instance those described herein.

Variant APOBEC3G fusion proteins include proteins that differ in amino acid sequence from the disclosed sequences, and sequence constructed from the disclosed protein portions, but that share structurally significant sequence homology with such proteins. Variation can occur in any single domain of the fusion protein (e.g. the functionalizing domain, the APOBEC3G protein domain, or the linker if such is present in the fusion). Variation can also occur in more than one of such domains in any particular variant protein. Such variants may be produced by manipulating the nucleotide sequence of the, for instance, APOBEC3G-encoding sequence, using standard procedures, including site-directed mutagenesis or mutagenic nucleic acid amplification (e.g., using PCR). The simplest modifications involve the substitution of one or more amino acids for amino acids having similar biochemical properties. These so-called "conservative" substitutions are likely to have minimal impact on the activity of the resultant protein, especially when made outside of the binding site of each domain.

More substantial changes in protein structure may be obtained by selecting one or more amino acid substitutions that are less conservative than those listed herein. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant APOBEC3G fusion protein-encoding sequences may be produced by standard DNA mutagenesis techniques, for example, M13 primer mutagenesis. Details of these techniques are provided in Sambrook (Ch. 15, In *Molecular Cloning: A Laboratory Manual*, CSHL, New York, 1989). By the use of such techniques, variants may be created which differ in minor ways from native APOBEC3G encoding sequences (for instance, BC024268 or NM-021822). DNA molecules and nucleotide sequences that are derivatives of native APOBEC3G-encoding sequences and that differ from such sequence by the deletion, addition, or substitution of nucleotides while still encoding a protein that has APOBEC3G biological activity, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed fusion sequences. For example, because of the degeneracy of the genetic code, four nucleotide codon triplets—GCT, GCG, GCC and GCA—code for alanine. The coding sequence of any specific alanine residue within a subject fusion protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode a APOBEC3G fusion protein, but which vary from the disclosed nucleic acid sequences by virtue of the degeneracy of the genetic code.

One APOBEC3G-GST fusion protein was described by Stopak et al. (*Molecular Cell,* 12:591–601, 2003). Recombinant APOBEC3G (produced in *E. coli*) is commercially available from ImmunoDiagnostics, Inc. (Woburn, Mass. 01801). In addition, the APOBEC3G-Myc fusion protein described herein (SEQ ID NO: 2) is further described in the paper by Marin et al. (*Nat. Med.* 9:1398–1403, 2003)), which is incorporated herein by reference. Sheehy et al. also used a APOBEC3G-HA tagged derivative (*Nature* 418, 646–650, 2002).

XII. Peptide Modifications

The present disclosure includes biologically active APOBEC3G molecules that are readily detectable in cell-based or cell-free systems, and specifically that maintain the ability to be degraded by the Vif-mediated degradation pathway. The proteins of the disclosure include synthetic embodiments of fusion proteins described herein, as well as analogues molecules (non-peptide organic molecules), derivatives (chemically functionalized protein molecules obtained starting with the disclosed peptide sequences) and variants (homologs) of these proteins that specifically maintain at least the susceptibility to such degradation and ready detectability (which function will be dependent on the label/marker moiety chosen). Proteins of the disclosure is comprised of a sequence of amino acids, which may be either L- and/or D-amino acids, naturally occurring and otherwise.

Proteins may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the protein side chains may be converted to $C_1$–$C_{16}$ alkoxy or to a $C_1$–$C_{16}$ ester using well-recognized techniques. Phenyl and phenolic rings of the protein side chains may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the protein side chains can be extended to homologous $C_2$–$C_4$ alkylenes. Thiols can be protected with any one of a number of well-recognized protecting groups, such as acetamide groups. Those skilled in the art will also recognize methods for introducing cyclic structures into the proteins provided herein to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the protein backbone and component amino acid side chains in a APOBEC3G fusion protein, resulting in such peptido- and organomimetics of the proteins of this disclosure having at least one APOBEC3G biological activity and are additionally detectable (conveyed by the "label" or "marker" portion of the molecule, such as a tag or fluorescent element, as discussed herein). For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165–174 and *Principles of Pharmacology* Munson (ed.) 1995, Ch. 102, for descriptions of techniques used in CADD. Also included within the scope of the disclosure are mimetics prepared using such techniques that produce biologically active, for the sake of the described assays, APOBEC3G fusion proteins.

It will be appreciated that the protein/peptide domains of fusions of the current disclosure may be combined to produce fusion protein molecules without necessarily splicing the components in the exact place identified herein. It is believed to be possible to use shorter or longer fragments of each component domain, for instance, longer or short portions of APOBEC3G. It is, however, usually not beneficial to use so short a portion of a tag or marking peptide that the tag or marking peptide is no longer functional (and therefore cannot provide detectability to the fusion protein).

XIII. Activity of Functionalized APOBEC3G Fusion Proteins

It is important to assess the activity (e.g., chemical, physical and/or biological activity) of fusion proteins used in the disclosed methods. Among other uses, such assays permit optimization of the domains chosen, optimization of the placement of the label portion within the fusion protein, optimization of the length and conformation of the linkers used to connect portions of the fusion, and determination of the effect(s) of variant amino acid changes in the fusion proteins. Appropriate control molecules can be included in each activity assay. Such controls molecules can include individual domains used to construct the fusion (e.g., a part or all of the APOBEC3G protein), composite domains expressed as separate molecules and mixed in the reaction, for instance in a 1:1 molar ratio, or fusions that include only one portion of the APOBEC3G fusion coupled to another protein or peptide (e.g., a different label on the same APOBEC3G protein or fragment thereof, or the same label on a different subject protein, either another APOBEC3G or a different fragment protein).

A. APOBEC3G Protein Activity

The key activity of the APOBEC3G portion of the provided fusion proteins in some embodiments is ability to be degraded, in the absence of inhibitory agent(s), via the Vif-dependent degradation pathway. Ample examples of how such activity can be examined are provided throughout this disclosure.

Another activity of APOBEC3G is its ability to interact with Vif, even without need to assay its ability to be degraded in a Vif-dependent manner. For instance, it is contemplated that some forms of APOBEC3G (for example, a derivative or fragment in which the APOBEC3G construction is missing a Lys-residue involved in Vif-mediated polyubiquitination) would still bind to Vif without in fact being effectively targeted for degradation. In assays that depend on the binding itself, such as for instance, ELISAs or the yeast two-hybrid system, it is import to ensure that the protein construct comprising APOBEC3G or a portion thereof is still capable of the interaction with Vif (in the absence of potential inhibitory agents).

By way of example, the inventors have shown that the binding of Vif to APOBEC3G occurs rapidly at 0° C. in cell extracts. If a sample containing Vif is mixed with a sample that contains APOBEC3G, complexes form that can readily be detected by immunoprecipitation (see, e.g., FIG. 13). In addition, APOBEC3G-Myc also can be adsorbed onto an agarose bead and the loaded bead add a sample that contains Vif. The Vif binds to these beads and can then be sedimented at low speed centrifugation from the solution. The Vif bound on the beads can then be detected and/or measured. Similarly, ELISAs can be used to measure the binding in cell extracts or other solutions. Additional techniques for determining the binding of two proteins to each other are well known to those of ordinary skill in the art.

B. Activity of a Detectable/Labeling Peptide

The biological activity of a detectable peptide that is fused to a APOBEC3G protein portion to form a fusion can be assayed independently of the APOBEC3G biological activity(s) of the fusion. The appropriate assay(s) for measuring functionalizing peptide activity will be dictated largely by the functionalizing peptide or protein. Fluorescent or other visibly detectable label moieties can be assayed by detection and/or measurement of the appropriate wavelength of emitted light, for instance after exposure to light of a selected wavelength.

The functionality of an epitope tag can be tested by detecting the fusion protein using an antibody (or antibody derivative) known to bind to the epitope, for instance in an immunoblot ("western"), ELISA, or other assay system; such techniques are well known. Other identification tags can be tested for functionality based on their intended method of identification—e.g., based on differential mobility or other added function. The functionality of a purification tag can be tested by using it to purify the fusion protein, for instance using column chromatography or other conventional techniques.

The effective functionality of a targeting domain within a fusion protein can be tested by examining the targeting of the fusion protein in an experimental or clinical system. Such targeting can be examined using conventional techniques, for instance fractionation, in situ hybridization, or through cell or tissue-specific biological effects that result from the targeting of the fusion protein (e.g., APOBEC3G mediated effects caused by the delivery of the fusion protein). Of course, detection of the detectable portion of the fusion protein is also contemplated.

Other passenger proteins can be assayed based on the native or expected function of the passenger protein. Assays appropriate for any particular passenger protein will be specific to that passenger, and will be known to those of ordinary skill in the art. In general, the assay will involve at least detection of the passenger, or the fusion as a whole.

The following examples are provided to illustrate certain particular features and/or embodiments. These examples should not be construed to limit the invention to the particular features or embodiments described.

EXAMPLES

Example 1

HIV-1 Vif Protein Binds the Editing Enzyme APOBEC3G and Induces its Degradation

This example demonstrates that Vif binds to APOBEC3G and induces its rapid degradation, thus eliminating it from cells and preventing its incorporation into HIV-1 virions (Marin et al., *Nat. Med.* 9:1398–1403, 2003).

Studies of Vif mutants imply that it contains two domains, one that binds APOBEC3G and another with a conserved SLQ(Y/F)LA motif that mediates APOBEC3G degradation by a proteasome-dependent pathway.

Methods

Expression vectors: pHIV-gpt(wt) and its derivative pHIV-gpt(Δvif) were previously described (Madani & Kabat, *J. Virol.* 72, 10251–10255, 1998; Page et al., *J Virol* 64, 5270–5276, 1990; Madani & Kabat, *J. Virol.* 74, 5982–5987, 2000). pcDNA3.1-Vif was donated by D. Gabuzda (Dana-Farber Cancer Institute, Harvard, Boston, Mass.). Rev-dependent plasmids for expression of the Vif mutants Δ2, Δ5, Δ6, Δ7, Δ9, Δ10, Δ12 and Δ13 (Simon et al., *J. Virol.* 73, 2675–2681, 1999) were provided by M. Malim (Medical Research Council, Cambridge, UK) and were coexpressed with pHIV-gpt(Δvif). APOBEC3G cDNA was cloned from H9 cells (nonpermissive) by reverse transcriptase-PCR (Barnes, *Proc. Natl. Acad. Sci. USA* 91, 2216–2220, 1994; Sambrook et al., *Molecular Cloning. A Laboratory Manual*, Chapter 14, 14.5–14.34., CSHL Press, Cold Spring Harbor, 1989) using primers complementary to the 5' and 3' ends of APOBEC3G coding region (Sheehy et al., *Nature* 418, 646–650, 2002) (upstream primer, 5'-GGG CTCGAGAGGATGAAGCCTCACTTCAGAAAC-3' (SEQ ID NO: 15) containing an XhoI restriction site [underlined]; downstream primer, 5'-GGG TTCGAAGTTTTCCTGATTCTGGAGAATGGC-3' (SEQ ID NO: 16) containing a SfuI restriction site [underlined]). The cDNA was cloned between XhoI and SfuI into the pcDNA3.1/Myc-His C mammalian expression vector (Invitrogen) to obtain the pcDNA3.1-APOBEC3G-Myc vector. The pSVIIIEnv vector was used to pseudotype HIV-gpt virions (Helseth et al., *J. Virol.* 64, 2416–2420, 1990). Transfections employed PolyFect reagent (Qiagen, Inc.) according to the manufacturer's instructions, with equimolar ratios of all plasmids and with harvests after 36 hours unless otherwise mentioned.

Viruses: HIV-gpt virions were produced and titered as previously described (Page et al., *J Virol* 64, 5270–5276, 1990; Page et al., *J Virol* 66, 524–533, 1992; Platt et al., *J. Virol.* 75, 12266–12278, 2001). For viral purifications, 27 ml of the virus-containing media from 293T cells were pelleted through 2 ml of a 20% sucrose at 100,000 g for 1.5 hours. Virions were resuspended in TSE (0.1 M NaCl, 1 mM EDTA, 0.01M Tris-Cl, pH 7.4), and centrifuged to equilibrium in 5 ml 20–60% sucrose gradients in TSE at 200,000 g for 2.5 hours. Virus-containing fractions were detected by immunoblotting using HIV Immunoglobulin serum (AIDS Research & Reference Program, Division of AIDS, NIAID, NIH: contributed by NABI and NHLBI). Peak fractions were pooled, diluted with TSE, and pelleted through 20% sucrose at 100,000 g for two hours.

Analysis of proteins and RNAs: Extracts of cotransfected 293T and COS7 cultures were prepared using either TX (1% Triton X-100, 150 mM NaCl, 10 mM Tris-Cl, pH 7.5, 1 mM MgCl) or RIPA (50 mM Tris-Ci pH 7.4, 1% Nonidet P40, 0.1% sodium deoxycholate, 150 mM NaCl) buffers with complete protease inhibitors (Roche), followed by centrifugation at 1,500 g for 5 minutes to sediment nuclei. Extracts were adjusted to equivalent protein concentrations using the Bradford reagent (BioRad Laboratories), and equal aliquots were then used for Western immunoblotting (Marin et al., *J. Virol.* 74, 8085–8093, 2000) or for immunoprecipitations (Klippel et al., *Mol. Cell. Biol.* 14, 2675–2685, 1994) using the antibodies HIV-1 HXB2 Vif rabbit antiserum #2221, (AIDS Research and Reference Reagent Program, Division of AIDS, NIAID, NIH: contributed by Dr. D. Gabuzda), Myc-specific monoclonal antibody clone 9E10 (Sigma) (Marin et al., *J. Virol.* 74, 8085–8093, 2000), or the ubiquitin-specific mouse monoclonal antibody (Zymed). This procedure for ensuring equal loading of proteins into the lanes of the illustrated gels was verified by immunoblotting with an antiserum specific for α-tubulin (Sigma). Where indicated, cultures were preincubated with 50 μM concentrations of the proteasome inhibitors ALLN, MG-132, or Proteasome Inhibitor-I (Calbiochem).

For immunoprecipitations, cell lysates were precleared by adsorption onto protein A-coated Sepharose 4B (Sigma) followed by incubations with Myc-specific antibody 9E10 and subsequent addition of protein A-coated Sepharose 4B. For Apobec-3G-Myc purifications based on its 6× His tag, culture extracts adjusted to equal volumes and protein concentrations were incubated with 100 μl/ml of Ni-NTA-agarose beads (50% slurry), followed by thorough washing (100 mM $NaH_2PO_4$, 10 mM Tris-Cl, 8M urea, pH 6.3) and elution (100 mM $NaH_2PO_4$, 10 mM Tris-Cl, 8M urea, pH 4.5) in denaturing conditions known to remove contaminants (Qiagen, Inc.).

Figure 5A:
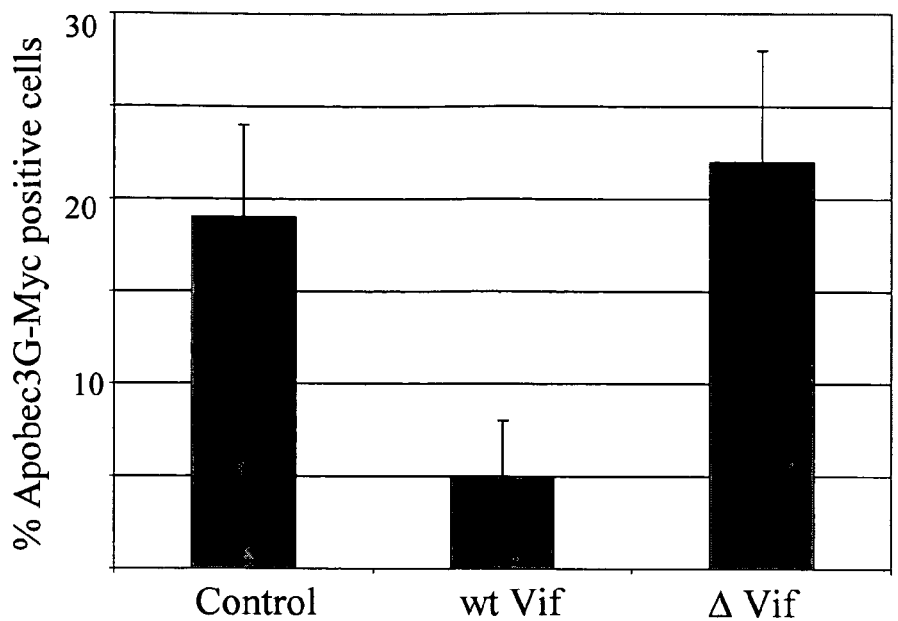
FIG. 5A shows a quantitative analysis of the effects of wild-type Vif on APOBEC3G-Myc expression at the cellular level, as seen in the immunofluorescence microscopy experiments. Whereas approximately 20% of the cells contained APOBEC3G-Myc in the cultures cotransfected 36 hours earlier with the negative control vector or with pHIV-gpt(Δvif), a much smaller percentage of cells contained APOBEC3G-Myc in cultures that contained wild-type Vif. Double immunofluorescence microscopy (i.e., staining for both APOBEC3G-Myc and for Vif with different colored dyes) showed that the small number of APOBEC3G-positive cells in this latter culture lacked Vif and, conversely, that Vif occurred almost exclusively in cells that lacked APOBEC3G (Marin et al., *Nature Med.* 9(11):1398–1403, 2003). These results imply that wild-type Vif efficiently eliminates APOBEC3G from cells, thereby reducing the number of APOBEC3G-positive cells in the cotransfected cultures and leaving APOBEC3G alone within the relatively small group of cells that lack any Vif.
Figure 5B:
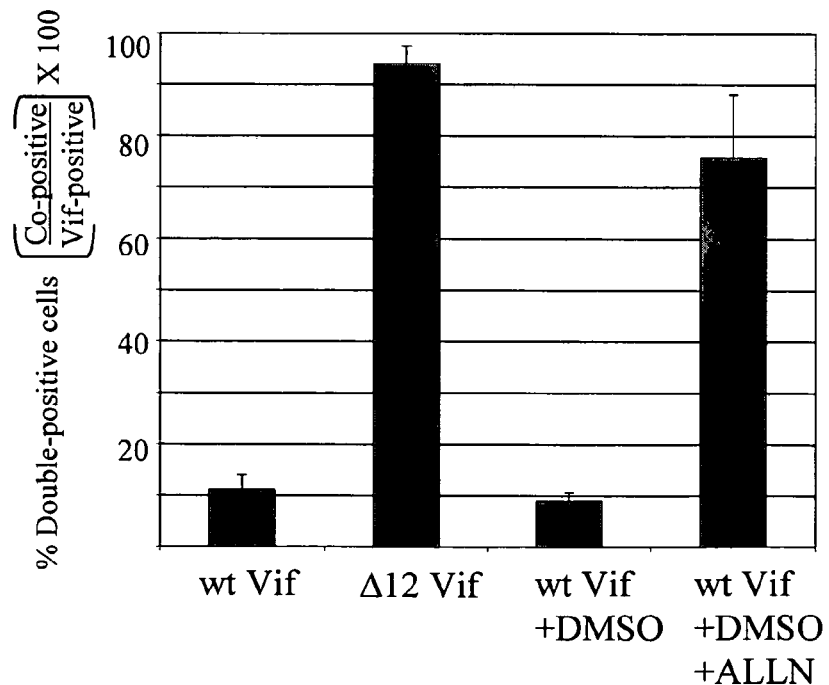
FIG. 5B shows the results of a quantitatively analysis of the effects of wild-type Vif and mutant Δ12Vif on coexpression of APOBEC3G-Myc within single cells. Only the wild-type Vif but not the mutant Vif caused elimination of APOBEC3G from the cells. Thus, over 90% of cells with Vif(Δ12) also contained APOBEC3G-Myc, whereas a relatively small number that contained wild-type Vif also contained APOBEC3G-Myc. In addition, the effects of the proteasome inhibitor ALLN dissolved in dimethylsulfoxide (DMSO) and of DMSO alone where examined. Approximately 25% of cells were Vif-positive in all of the cultures. Vif-positive cells were examined for the percentages that coexpressed APOBEC3G-Myc (double-positive). Wild-type Vif caused a large decrease in APOBEC3G-Myc coexpression independently of DMSO, and this decrease was alleviated by ALLN. This quantitative data supports a conclusion that wild-type but not mutant Vif proteins cause degradation of APOBEC3G by a proteasome-dependent pathway.

For immunofluorescence, COS7 cells were used because they are more adherent than 293T cells. Cells cultured in Permanox chamber slides (Nalge Nunc International) were fixed in 5% formaldehyde and 2% sucrose in PBS (Invitrogen) at room temperature for 20 minutes, and permeabilized with 1% Triton X-100 in PBS with 10% sucrose for 30 minutes. Primary antibodies were Vif antiserum #2221 or the Myc-specific monoclonal antibody 9E10. Secondary fluorescent antibodies were Alexa Fluor 488 goat anti-rabbit IgG(H+L) and Alexa Fluor 594 goat anti-mouse IgG (H+L) (Molecular Probes Inc), which reacted only with their species-specific primary antibodies. Slides were mounted in FluoroGuard (BioRad Laboratories), and observed with a Zeiss Axiovert 200M deconvolution microscope. The percentage of double-positive cells in FIG. 5B is defined as the percentage of the Vif-positive cells and that contained APOBEC3G-Myc. RNA extraction and Northern blot analyses were previously described (Tailor et al., *Proc. Natl. Acad. Sci. USA* 96, 927–932, 1999). A cDNA probe for the S2 ribosomal protein was used as a loading control.

Pulse-chase experiments: Tran$^{35}$S-label (ICN Biochemicals, Inc.) was diluted with unlabeled L-cysteine and L-methionine to a final specific radioactivity of 20 Ci/mmole. Cultures were washed and incubated with DMEM lacking cysteine and methionine for 60 minutes at 37° C. They were pulse-labeled in the same medium with 80 μCi/ml of the Tran$^{35}$S-label solution for 4 minutes and rapidly washed and chased in complete growth medium supplemented with 10× unlabeled methionine and cysteine plus cycloheximide (50 μg/ml) (Sigma). Cytosolic RIPA buffer extracts were immunoprecipitated with Myc antibody 9E10. Low exposure autoradiograms were scanned by densitometry.

Figure 4A:
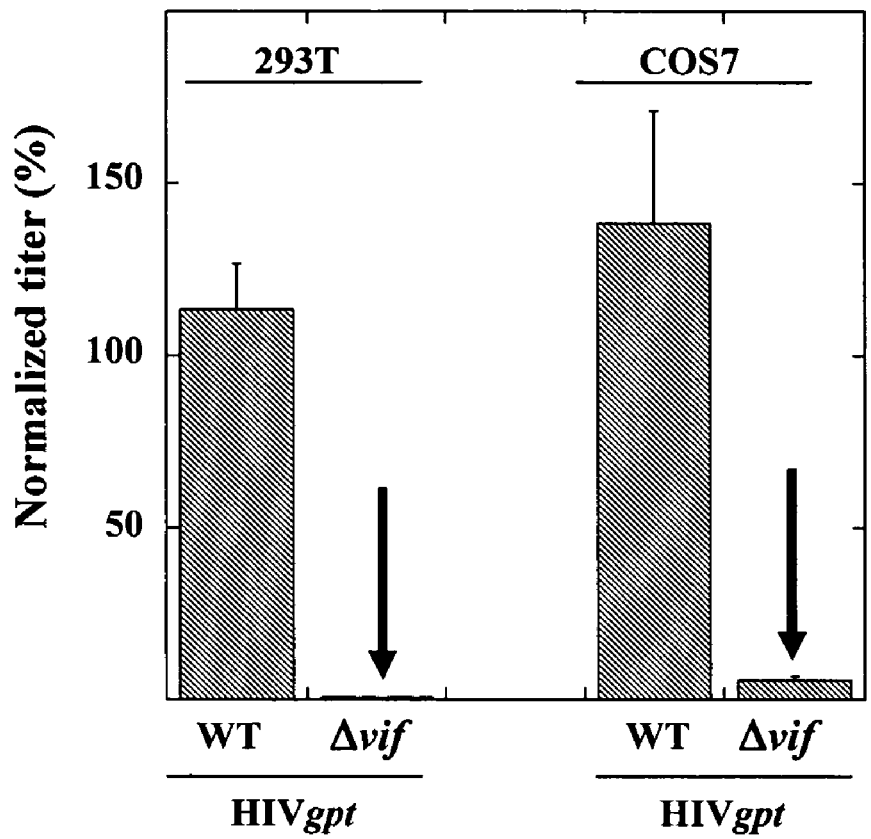
FIG. 4A is a bar graph showing that APOBEC3G had no significant effect on titers of HIV-gpt (wild-type) but strongly reduced titers of HIV-gpt(Δvif).
Figure 4B:
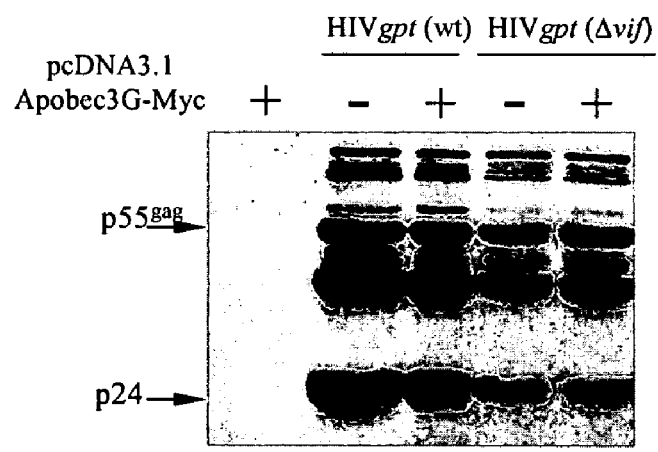
FIG. 4B is a Western Blot, indicating that APOBEC3G-Myc had no effect on synthesis of Gag proteins, consistent with the classical NP phenotype. Extracts of cotransfected 293T cells were analyzed for HIV-1-encoded Gag proteins by immunoblotting. As expected, NP cells produce HIV-1 (Δvif) proteins and virions in the same amounts they produce HIV-1 (wild-type) proteins and virions, but the released Δvif virions have a very low infectivity to particle ratio (Gaddis et al., *J. Virol.* 77, 5810–5820, 2003; Ochsenbauer et al., *Gen. Virol.* 78, 627–635, 1997).

Expression of APOBEC3G-Myc Converts Human and Monkey Permissive Cells to Nonpermissive To analyze the antiviral activity of pcDNA3.1-APOBEC3G-Myc, human 293T and African green monkey COS7 cells were transiently cotransfected with pcDNA3.1-APOBEC3G-Myc in the presence of vectors for expression of HIV-gpt(wt) or HIV-gpt(Δvif) [these are derivatives of wild-type (wt) or vif deleted (Δvif) HIV-1 with the bacterial gpt gene replacing the viral env gene; Madani & Kabat, *J. Virol.* 72, 10251–10255, 1998; Page et al., *J Virol* 64, 5270–5276, 1990; Madani & Kabat, *J. Virol.* 74, 5982–5987, 2000]. Virions were subsequently harvested from the culture media and analyzed their infectivities in HeLa-CD4 (clone HI-J) cells. APOBEC3G-Myc reproducibly decreased the titers of HIV-gpt(Δvif) virions by approximately 25–100-fold, but had no effect on titers of HIV-gpt(wt), strongly suggesting that it converts human and African green monkey permissive cells to nonpermissive (see FIG. 4). Consistent with this conclusion, APOBEC3G-Myc had no significant or reproducible effect on synthesis of HIV-1 encoded proteins in the producer cells or on their packaging into virions. Similar results were obtained with owl monkey kidney cells. Thus, HIV-1 Vif neutralizes human APOBEC3G-Myc in both human and monkey cells.

Vif Eliminates the APOBEC3G Protein from Cells

Figure 3B:
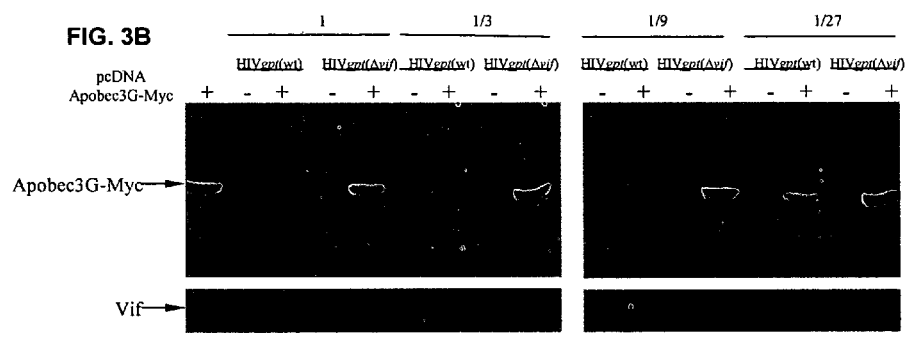
FIG. 3B shows the effects of altering quantities of pHIV-gpt plasmids relative to the APOBEC3G-Myc plasmid. Down modulation of APOBEC3G-Myc is most extensive when the plasmid molar ratio is 1:1, but it remains substantial even when pHIV-gpt plasmids are reduced by 27-fold.
Figure 3C:
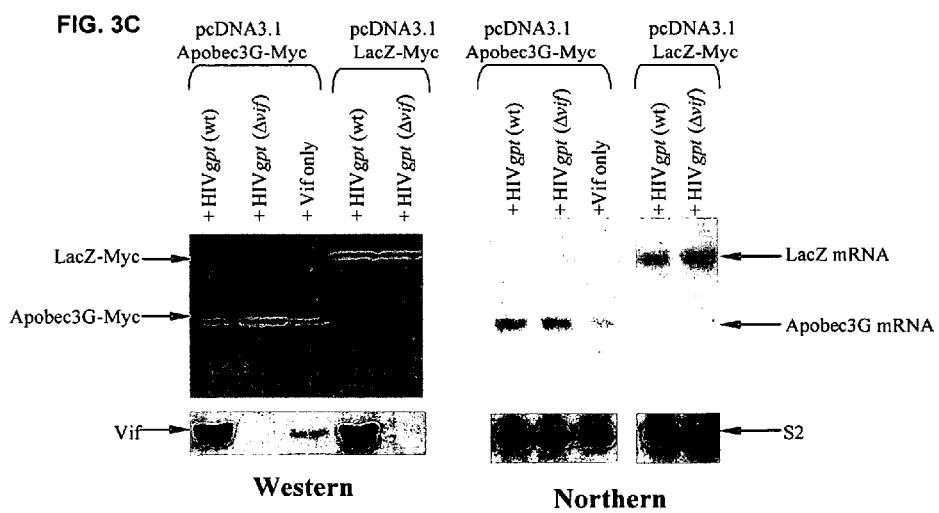
FIG. 3C (left portion) shows that APOBEC3G-Myc down modulation also occurs with a pcDNA3.1-Vif vector (Vif only) in the absence of other HIV-1-encoded proteins, and that Vif has no effect on expression of LacZ-Myc encoded by the same vector.

A transient cotransfection system was then used to analyze the mechanism by which Vif neutralizes the antiviral activity of APOBEC3G. Extracts of cultures that had been cotransfected with the indicated vectors were adjusted to equal protein concentrations prior to Western blot analysis. Cultures that had been cotransfected with pHIV-gpt(wt) reproducibly contained approximately 4–10-fold less APOBEC3G-Myc (SEQ ID NO: 2) than cultures that had been cotransfected with pHIV-gpt(Δvif) (FIG. 3). Vif-induced down modulation of APOBEC3G-Myc was largest when the pcDNA3.1-APOBEC3G-Myc and pHIV-gpt plasmids were cotransfected in equimolar amounts, but was still substantial when the pHIV-gpt plasmids were reduced 27-fold (FIG. 3B). APOBEC3G-Myc down modulation also occurred when the cells were cotransfected with a pcDNA3.1-Vif vector, suggesting that it did not require HIV-1-encoded proteins in addition to Vif (FIG. 3C). Vif had no effect on expression of LacZ-Myc expressed from the same pcDNA3.1 vector or on the quantities of APOBEC3G or LacZ mRNAs in the cell cultures (FIG. 3C) or in HIV-1-infected H9 leukemic T cells (nonpermissive). APOBEC3G-Myc had no effect on expression of Vif (FIGS. 3A and 3B). The accuracy of the protein concentration adjustments was substantiated by immunoblotting of the control protein α-tubulin (FIG. 3A).

Effects of Vif on APOBEC3G-Myc were also analyzed by immunofluorescence microscopy. Normally, when two plasmids are cotransfected into cultured cells, nearly all of the cells that take up the aggregate of foreign DNA coexpress the proteins encoded by the two distinct plasmids. In contrast, most other cells in the culture generally express neither of the plasmid-encoded proteins, although a small fraction of the cells do often synthesize only one of the proteins. Thus, in the cotransfected COS7 cultures, it would be expected that most of the cells that expressed Vif would also contain APOBEC3G. However, in striking contrast to this expectation, it was found that the cells with Vif lacked readily detectable APOBEC3G, and that the few cells with APOBEC3G lacked readily detectable Vif. Thus, there was almost complete segregation in expression of these proteins rather than the expected coexpression.

In striking contrast, when a plasmid was cotransfected that encoded an inactive mutant of Vif with a plasmid that encodes APOBEC3G-Myc, almost complete coexpression of these proteins was observed. Additionally, cultures cotransfected with vectors for APOBEC3G-Myc and wild-type Vif and treated with the proteasome inhibitor ALLN showed a dramatic increase in coexpression of both proteins within single cells. These results strongly suggested that wild-type Vif eliminates APOBEC3G from cells by a pathway that requires degradation by proteasomes. Immunofluorescent photographs illustrating these results were published in Marin et al. (*Nature Med.* 9(11):1398–1403, November 2003), which is incorporated herein by reference.

Immunofluorescence microscopy indicated almost complete segregation of APOBEC3G-Myc from wild-type Vif within the transiently cotransfected cultures, with some cells containing APOBEC3G-Myc but no Vif, and with others containing Vif but no APOBEC3G-Myc. Moreover, the percentage of cells with APOBEC3G-Myc was approximately four times lower in the cultures that had been cotransfected with pHIV-gpt(wt) than in cultures that had been cotransfected with a negative control vector or with pHIV-gpt(Δvif) (FIG. 5A). This Vif-dependent reduction in the proportion of cells with APOBEC3G-Myc corresponds within experimental error to the degree of APOBEC3G-Myc down modulation seen by immunoblotting. This implies that APOBEC3G-Myc expression is eliminated in cells that contain wild-type Vif, and that the residual APOBEC3G-Myc that remains in the cultures is in a small population of cells that lack Vif.

Consistent with this interpretation, mutations in Vif that eliminate its activity all blocked its ability to down modulate APOBEC3G-Myc (see below), and these mutant Vif proteins were extensively coexpressed with APOBEC3G-Myc within single cells. For example, approximately 95% of the cells that expressed the previously described (Simon et al., *J. Virol.* 73, 2675–2681, 1999) inactive Δ12Vif mutant contained APOBEC3G-Myc, whereas only approximately 10% of the cells with wild-type Vif had APOBEC3G-Myc (FIG. 5B). The latter double-positive cells may have been overestimated because they had only trace amounts of wild-type Vif that were difficult to distinguish from the background staining with this antiserum. It is believed that these cells might have only recently begun to synthesize wild-type Vif.

Figure 6:
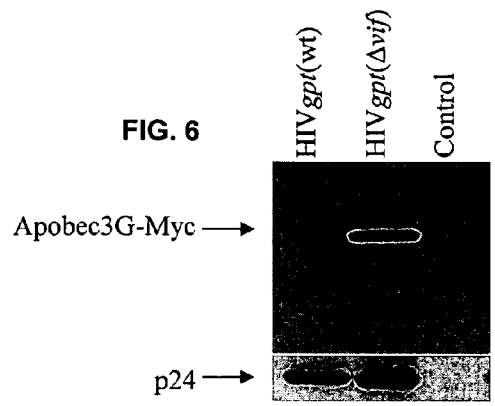
FIG. 6 illustrates that Vif blocks incorporation of APOBEC3G into purified HIV-1 virions. Cultures of 293T cells were cotransfected with pcDNA3.1-APOBEC3G-Myc in the presence of vectors for expression of HIV-gpt(wt) or HIV-gpt(Δvif). Virions from the culture media were purified by equilibrium density centrifugation. The HIV-gpt(wt) virions lacked APOBEC3G-Myc, whereas the HIV-gpt(Δvif) virions contained APOBEC3G-Myc. The virion samples contained similar amounts of HIV-1 Gag protein p24. A control preparation from the culture medium of cells expressing APOBEC3G-Myc alone was negative, indicating the absence of APOBEC3G-Myc in cell-derived microvesicles that heavily contaminate HIV-1 preparations (Gluschankof et al., *Virology* 230, 125–133, 1997). Because Vif eliminates APOBEC3G from cells (see FIG. 5), the HIV-gpt(wt) are made in cells that lack APOBEC3G, which explains why these virions specifically lack APOBEC3G.

Vif and the HIV-1 core and envelope proteins accumulate coordinately in a Rev-dependent manner late in the infection cycle (Garrett et al., *J. Virol.* 65, 1653–1657, 1991). Therefore, production of progeny virions would be expected to occur almost exclusively in cells that contain large amounts of Vif and that consequently lack APOBEC3G (see FIG. 5A). In agreement with this prediction, APOBEC3G-Myc was reproducibly detected in the HIV-gpt(Δvif) virions but not in the HIV-gpt(wt) virions (FIG. 6). A control using cells that express APOBEC3G-Myc alone excluded a contribution to our results of contaminating cell-derived microvesicles (Gluschankof et al., *Virology* 230, 125–133, 1997).

Vif Binds to APOBEC3G-Myc

Figure 7A:
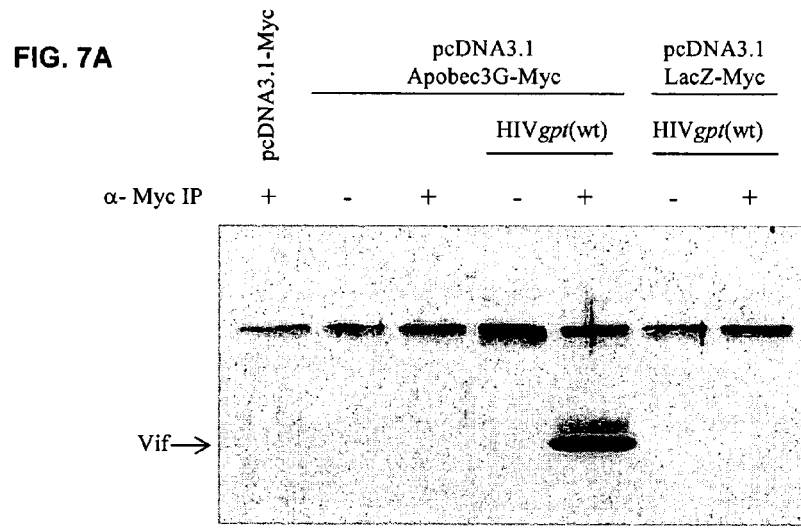
FIG. 7A: The cell extracts were precleared by adsorption onto protein A-Sepharose 4B beads. The precleared extracts were then divided into two portions, one that received the 9E10 anti-Myc antibody (labeled +) and the other without (labeled −) before adsorption onto additional protein A-Sepharose 4B beads. The eluted proteins were analyzed by immunoblots that were developed using the Vif-specific rabbit antiserum. Vif co-immunoprecipitates with APOBEC3G-Myc in a highly specific manner.
Figure 7B:
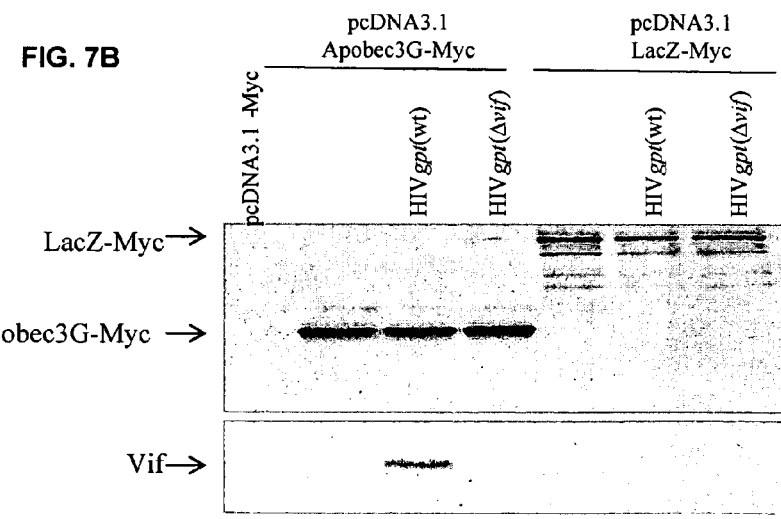
FIG. 7B: 293T cell cultures were separately transfected with the individual plasmids, and cell extracts were then prepared from these cells and from the negative control cells. The extracts were then mixed for 30 minutes at 0° C. prior to preclearing and immunoprecipitation using the Myc-specific monoclonal antibody, and the immunoprecipitated proteins were then analyzed for Vif by Western immunoblotting. The results show that Vif and APOBEC3G made in separate cell cultures formed a specific complex when the cell extracts were mixed prior to immunoprecipitation. Vif had no effect on the quantity of APOBEC3G-Myc in these mixed extracts incubated at 0° C. Thus, Vif did not cause degradation of APOBEC3G-Myc in the cell extracts at 0° C. These results show that Vif-APOBEC3G complexes can form rapidly in cell extracts, and that the presence of complexes does not prove that the complexes occurred within cells prior to making the extracts. This is important because our immunofluorescence microscopy results show that Vif and APOBEC3G are segregated into different cells in the cotransfected cultures prior to lysis.
Figure 8A:
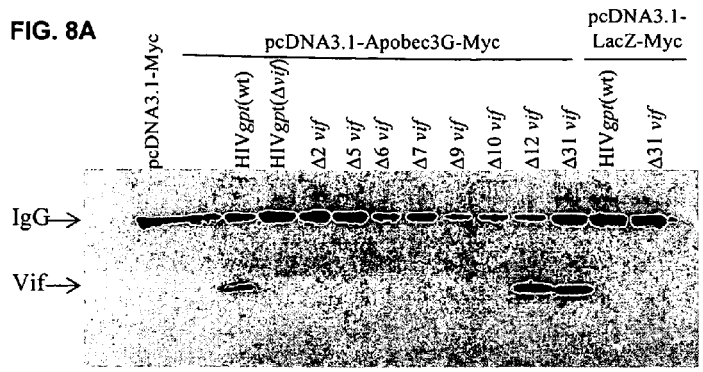
FIG. 8A shows that wild-type Vif co-immunoprecipitated with APOBEC3G-Myc but not with LacZ-Myc. A series of small in-frame Vif deletion mutants, which all eliminate Vif activity by at least 93% (Simon et al., *J. Virol.* 73, 2675–2681, 1999), were also analyzed. Only the Δ12 and Δ31 mutants bind to APOBEC3G. These mutations overlap and they both eliminate the SLQ(Y/F)LA motif that is the most conserved sequence in lentiviral Vif proteins. Therefore, this motif-containing region of Vif is not needed for binding to APOBEC3G, although it is required for APOBEC3G degradation. Therefore, Vif function requires two regions, one that binds to APOBEC3G and a second that includes the conserved motif that is required for the degradation but not for the binding.

Vif coimmunoprecipitates with APOBEC3G-Myc from RIPA buffer extracts of cell cultures that contain these proteins. This is a specific association that requires both proteins as well as the monoclonal antibody to Myc (FIG. 8A). Vif did not co-immunoprecipitate with LacZ-Myc using the same monoclonal antibody. Initially, this was confusing because immunofluorescence results indicated that Vif and APOBEC3G-Myc are segregated into different cells within the cultures (FIG. 5). This was resolved by finding that the association of Vif with APOBEC3G-Myc occurs in cell extracts and is not indicative of pre-existing intracellular complexes. Thus, complexes were coimmunoprecipitated from mixtures of two cell extracts that individually contained the discrete proteins (see FIG. 7). These results do not establish whether the binding of Vif to APOBEC3G is direct or is mediated by other factors, such as one or more additional proteins or other cell components.

Figure 8B:
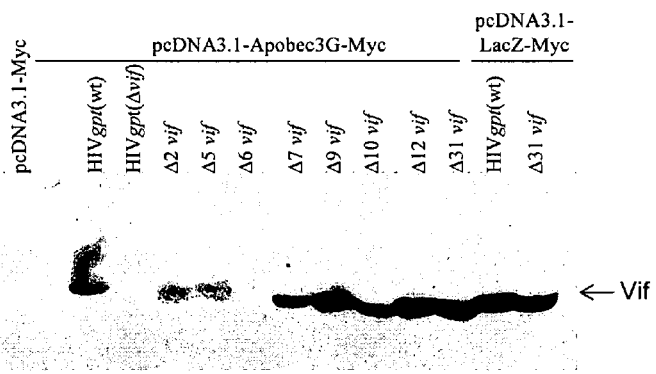
FIG. 8B shows an immunoblot analysis of Vif in aliquots of the cell extracts that were not immunoprecipitated. All of the mutant Vif proteins were produced in the cells and were detected with Vif antiserum except for the Δ6 mutant. The Vif antiserum was a gift from the NIH AIDS Repository, and was provided to them by Dr. Dana Gabuzda (Dana Farber Institute, Harvard Medical School, Boston, Mass.).
Figure 8C:
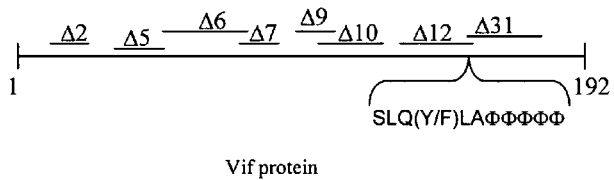
FIG. 8C is a linear map of Vif with positions of the deletion mutations.
Figure 8D:
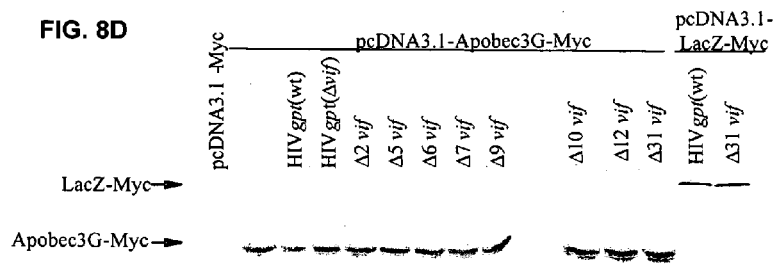
FIG. 8D shows the effects of wild-type and mutant Vif proteins on down modulation of APOBEC3G. Only wild-type Vif down modulated APOBEC3G. Thus, all of the Vif mutants we used lacked ability to neutralize the nonpermissive phenotype of cells, and they correspondingly were all unable to degrade APOBEC3G. This strongly suggests that the Vif-dependent degradation of APOBEC3G is necessary and sufficient to neutralize the NP phenotype of cells.

A series of small deletion mutations at different positions in Vif was analyzed. All of the deletion mutations severely inhibit Vif's activity by at least 93% (Simon et al., *J. Virol.* 73, 2675–2681, 1999). Coimmunoprecipitation assays indicated that most of these Vif mutations prevented association with APOBEC3G-Myc (FIG. 8A). All mutant Vif proteins were detected in the cell extracts, except the Δ6 mutant, which may be rapidly degraded or unreactive with the presently tested antiserum (FIG. 8B). However, the Δ12 and Δ31 deletion mutants clearly bound to APOBEC3G-Myc. Interestingly, these two deletions overlap and they both remove the SLQ(Y/F)LAΦΦΦΦ motif that is the most conserved site in Vif proteins of HIV-1 and other lentiviruses (Oberste & Gonad, *Virus Genes* 6, 95–102, 1992) (FIG. 8C). All mutations that prevent Vif function blocked Vif-induced down modulation of APOBEC3G-Myc (FIG. 8D).

Vif Induces Rapid Degradation of APOBEC3G

Based on the above evidence, we postulated that association with wild-type Vif might induce rapid APOBEC3G-Myc degradation. However, because the transiently cotransfected cultures contain a small proportion of cells that lack wild-type Vif and therefore accumulate APOBEC3G-Myc (FIG. 5), it was anticipated that this residual APOBEC3G-Myc would have a relatively long lifespan. To analyze this background, the cotransfected 293T cultures were treated with cycloheximide to block protein synthesis. The quantities of APOBEC3G-Myc was subsequently analyzed by Western immunoblotting. These studies established that the residual APOBEC3G-Myc in the cultures cotransfected with pHIV-gpt(wt) and the APOBEC3G-Myc in the cultures cotransfected with pHIV-gpt(Δvif) both turn over slowly, with half-lives of approximately eight hours.

Figure 9A:
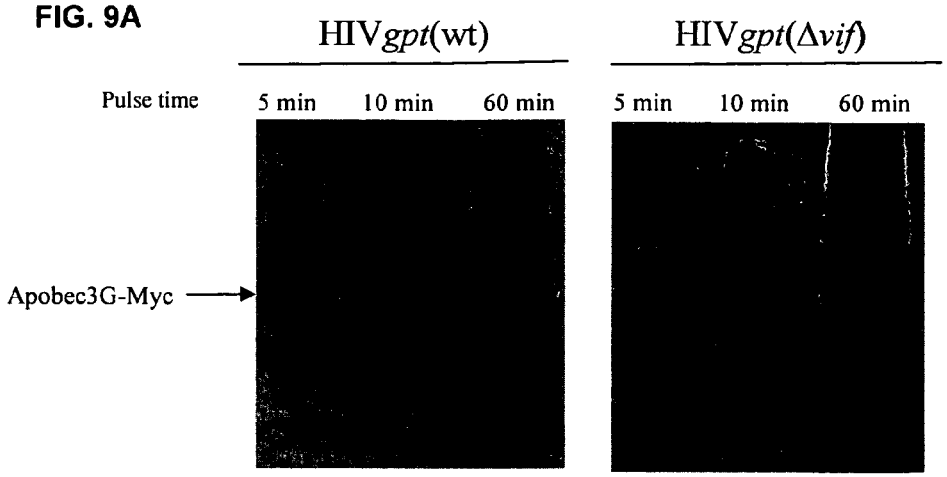
FIG. 9A: After 36 hours, the cultures were washed 2× with DMEM lacking cysteine and methionine and incubated with the same media for 60 minutes at 37° C. The cells were then labeled in the continuous presence of L-[$^{35}$S]amino acids (final specific radioactivity of 10 Ci/mmole) for 5, 10, or 60 minutes. APOBEC3G-Myc was immunoprecipitated from the cell extracts and the immunoprecipitated proteins were analyzed by electrophoresis followed by autoradiographic detection. The amounts of [$^{35}$S]APOBEC3G-Myc in the two cultures were similar after 5 minutes of labeling. However, by 60 minutes of continuous incorporation the culture lacking Vif had accumulated approximately 4–5 times more [$^{35}$S]APOBEC3G-Myc than the culture containing Vif. The results suggest that a large proportion of the [$^{35}$S]APOBEC3G-Myc synthesized in cultures that contain Vif is rapidly degraded. The remainder accumulates in cells that lack Vif (see FIG. 5).
Figure 9B:
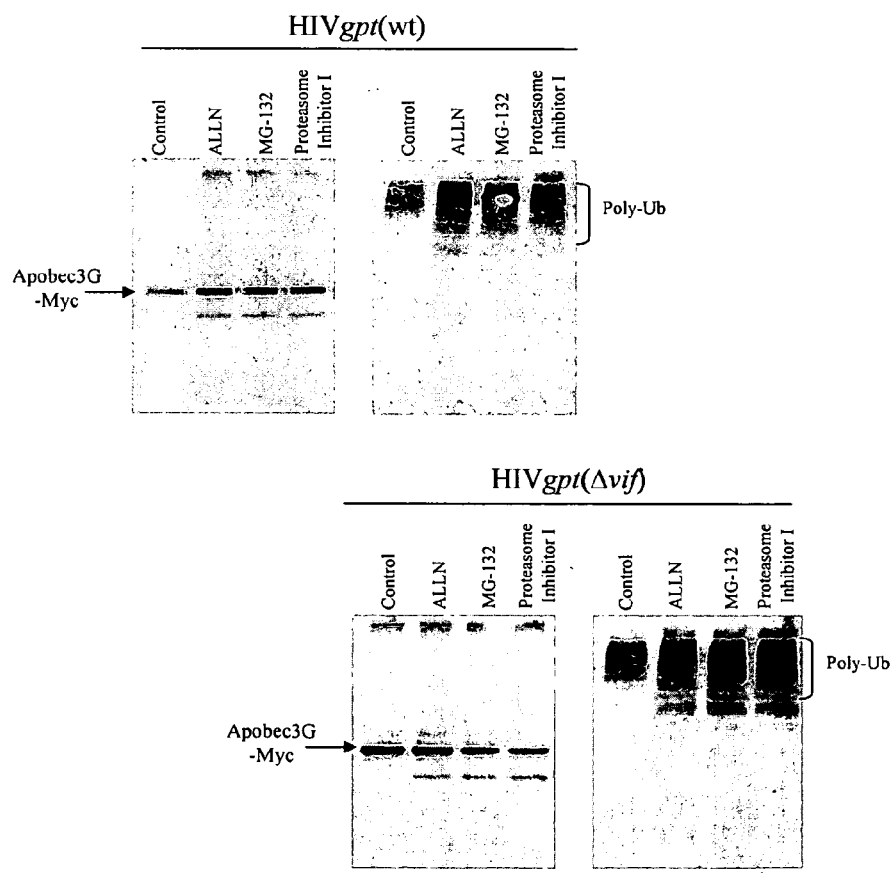
FIG. 9B is an analysis of proteasome inhibitor activities in 293T cultures that express APOBEC3G-Myc in the presence or absence of Vif. The cultures were preincubated for 6 hours with the proteasome inhibitors ALLN, MG-132, or Proteasome Inhibitor-I prior to lysis and Western blot analyses of the total cell culture extracts. In the left panels of each pair of blots, we used the antibody specific for Myc. The proteasome inhibitors increased the quantities of APOBEC3G-Myc in the cultures that contained Vif but not in the cultures that lacked Vif. This supports the conclusion that Vif induces relatively rapid degradation of APOBEC3G-Myc by a proteasome-dependent pathway, and substantiates the immunofluorescence microscopy data on this same issue. The right panels of each pair of blots are analyses of proteins in the total cell culture extracts that bind to the ubiquitin-specific antibody. The proteasome inhibitors were active in both cultures, as indicated by their augmentations of the quantities of total cellular polyubiquitinated proteins. The polyubiquitinated proteins in these extracts consist of numerous cellular proteins and are not specifically related to APOBEC3G-Myc.

To initially determine whether Vif induces rapid APOBEC3G-Myc degradation, APOBEC3G-Myc-positive cultures that contained or lacked Vif were incubated in the continuous presence of L-[$^{35}$S]methionine plus L-[$^{35}$S]cysteine, and the labeling of APOBEC3G-Myc measured as a function of time. When the labeling periods were 5 minutes or less, the amounts of [$^{35}$S]APOBEC3G-Myc were usually very similar in these cultures, but by 60 minutes the cultures without Vif contained 4–5 times more [$^{35}$S]APOBEC3G-Myc (see FIG. 9). These studies suggested that a large proportion of the APOBEC3G-Myc synthesized in the cultures that contained Vif had a very short half-life.

Pulse-chase labeling experiments confirmed these conclusions, and indicated that the 293T and COS7 cultures with Vif transient contain a substantial pool of APOBEC3G-Myc that is degraded within minutes of its synthesis (FIG. 10). In contrast, newly synthesized APOBEC3G-Myc is stable in the cultures that lack Vif. Indeed, the Vif-dependent component of APOBEC3G-Myc degradation was so rapid that it was difficult to detect unless the pulse-labeling time was 5 minutes or less and the chase times were also very short. Furthermore, optimal detection of this degradation required that the chase medium function quickly to terminate incorporation and that delays associated with rinsing the culture plates be minimized. If these conditions are not all met, as in a recent report (Gluschankof et al., *Virology* 230, 125–133, 1997), only the slow degradation that occurs in the cells lacking Vif can be detected. Based on many pulse-chase analyses, we conclude that the Vif-dependent component of APOBEC3G-Myc degradation is extremely rapid ($t_{1/2}$~1–2 minutes).

Figure 11A:
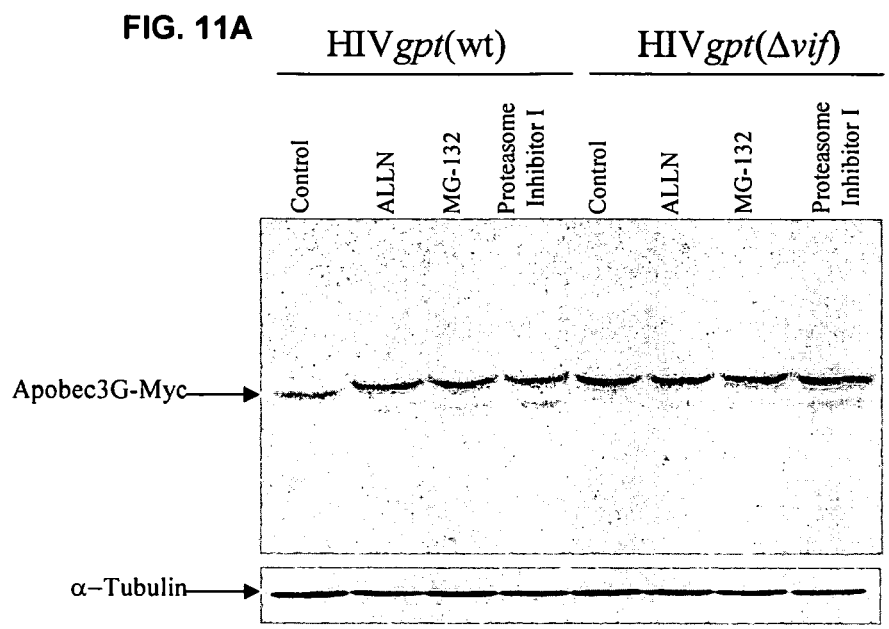
FIG. 11A shows cultures that were incubated for 10 hours with the proteasome inhibitors ALLN, MG-132, or Proteasome Inhibitor-I, prior to analysis of lysates by immunoblotting of APOBEC3G-Myc or the α-tubulin loading control. The inhibitors specifically increased the quantity of APOBEC3G-Myc in the cultures that contained Vif, but not in those that lacked Vif. This shows that the Vif-dependent down modulation of APOBEC3G-Myc involves proteasomes.
Figure 11B:
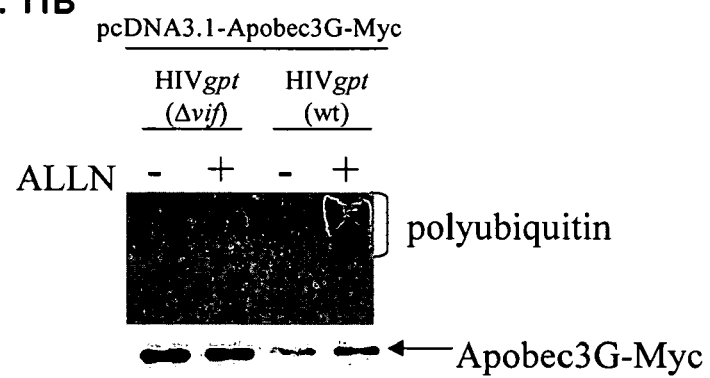
FIG. 11B shows cultures that were incubated for 10 hours with the proteasome inhibitor ALLN prior to purification of APOBEC3G-Myc from cell extracts using Ni-NTA agarose and washing and elution buffers that contained 8M urea. The purified APOBEC3G-Myc proteins were analyzed by western immunoblotting with a ubiquitin-specific antibody. The results suggest that APOBEC3G is polyubiquitinated and that the amount of polyubiquitinated APOBEC3G is greatly increased by Vif and by proteasome inhibitors.
Figure 12A:
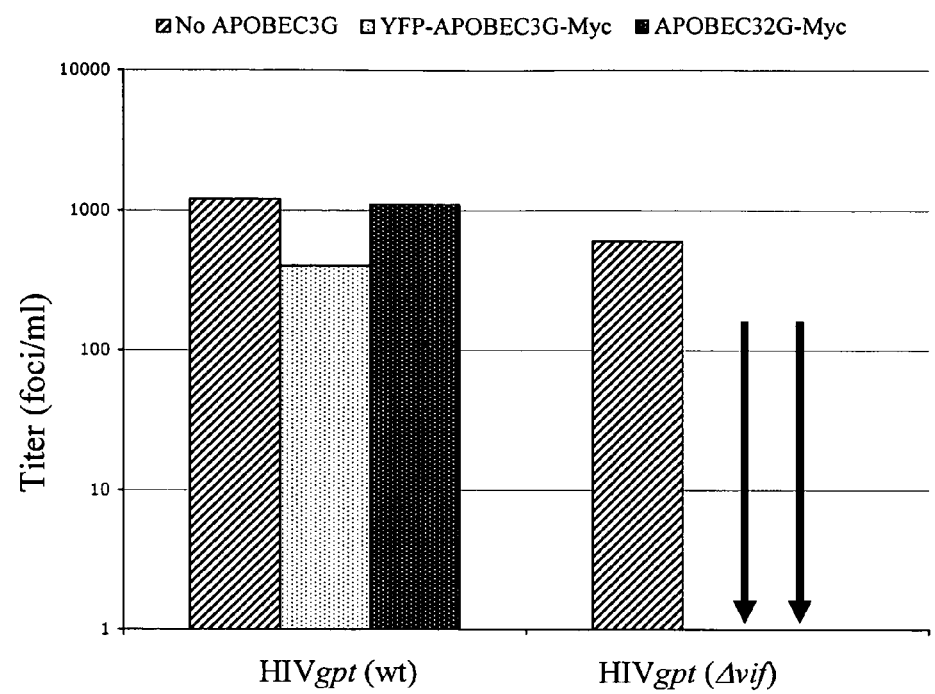
FIG. 12A is a graph showing the titer of various viral constructs produced from human 293T cells. Cells that express YFP-APOBEC3G-Myc or APOBEC3G-Myc in the absence of Vif produce only defective inactive HIV-1 virions, as shown by low titer (indicated by the arrows). In contrast, virions made in cultures that contain Vif (No APOBEC3G) are fully active. Similarly, an APOBEC3G-luciferase chimera with luciferase at its carboxyl terminal end also has antiviral activity only in the absence of Vif (not shown).
Figure 12B:
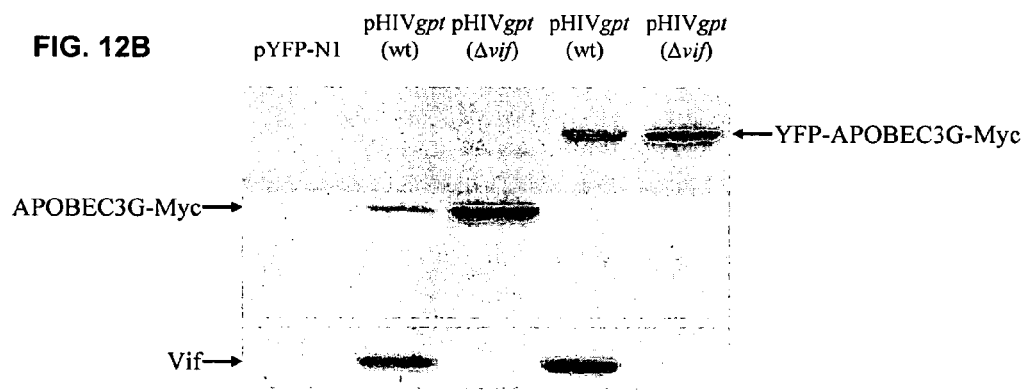
FIG. 12B is a western blot of the YFP-APOBEC3G-Myc and APOBEC3G-Myc chimeric proteins in transfected 293T cultures, illustrating that Vif down-modulates the amount of YFP-APOBEC3G-Myc in the culture (lanes 4 and 5). Similarly, Vif down modulates expression of APOBEC3G-Myc (lanes 2 and 3). Vif similarly down-modulated APOBEC3G-luciferase in a similar assay (not shown). This supports the data in FIG. 12A in showing that Vif neutralizes the antiviral activity of both YFP-APOBEC3G-Myc and the control protein APOBEC3G-Myc.
Figure 12C:
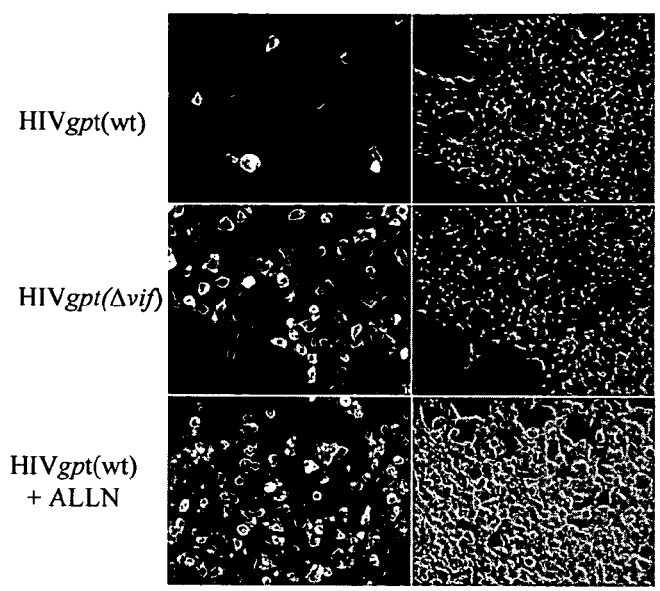
FIG. 12C is a series of fluorescence micrographs of cultures that had been transfected with vectors for expression of YFP-APOBEC3G-Myc in the presence or absence of Vif, and include an analysis of the proteasome inhibitor ALLN. The left panels are fluorescent images of the same field of cells shown in the right panels in phase contrast images. The phase contrast images show all cells in the fields, whereas only the cells that contain YFP-APOBEC3G-Myc appear in the fluorescent images. The data shows that the fields of cells being compared all contain similar numbers of cells, but differ dramatically in the number that fluoresce. As seen by the fluorescent images, cotransfection with a plasmid that encodes Vif caused a dramatic decrease in the percentage of cells that show a detectable amount of YFP-APOBEC3G-Myc fluorescence. However, treatment of a culture that contains Vif and YFP-APOBEC3G-Myc with ALLN for eight hours caused YFP-APOBEC3G-Myc to accumulate in many more cells. This further supports the conclusions stated in Marin et al. (*Nature Med.* 9(11): 1398–1403, 2003) and herein, that the presence of Vif in cells causes elimination of APOBEC3G-Myc by a mechanism that requires proteasomes.
Figure 12D:
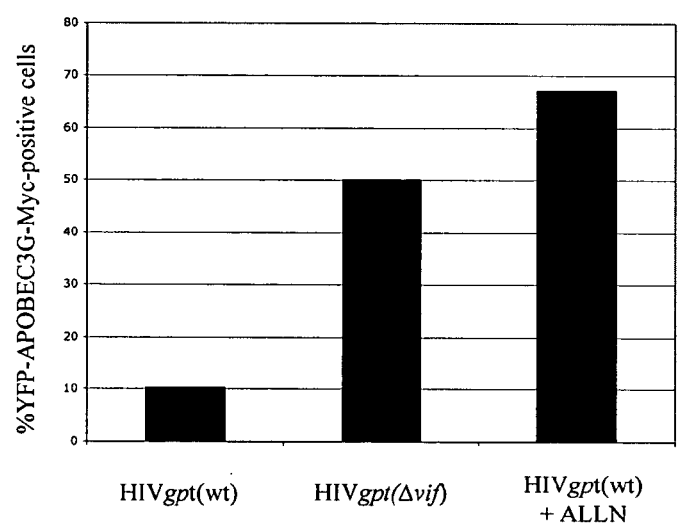
FIG. 12D is a bar graph showing quantitative analysis of the data shown in FIG. 12C.

Consistent with these interpretations, treatments with the proteasome inhibitors ALLN, MG-132, or Proteasome Inhibitor-I for 6–10 hour reproducibly increased the quantities of APOBEC3G-Myc in the cultures that contained Vif, but not in the cultures that lacked Vif, and had no effect on the control protein α-tubulin (FIG. 11A). These inhibitors were active in both cultures, as indicated by their enhancements in the amounts of total polyubiquitinated proteins (see FIG. 9). Immunofluorescence microscopy confirmed that ALLN also caused a dramatic increase in the percentage of cells that coexpressed wild-type Vif and APOBEC3G-Myc (see FIGS. 5A and 5B). Because the APOBEC3G-Myc fusion protein contains a 6×His tag adjacent to the Myc epitope, we were able to purify it away from Vif and other associated factors in highly denaturing conditions containing 8M urea. Interestingly, these preparations contained large polyubiquitinated proteins in amounts that were increased by Vif and by proteasome inhibitors (FIG. 11B). It is believed, based on these results and the sequence evidence described herein, that Vif-induced APOBEC3G degradation occurs by a proteasome-dependent pathway that may involve ubiquitination.

Discussion

These results substantially clarify the mechanism by which Vif neutralizes an innate antiviral pathway in human T lymphocytes. Specifically, Vif binds to the APOBEC3G cytidine deaminase and targets it for rapid degradation by a proteasome-dependent pathway. The rate of this Vif-induced degradation ($t_{1/2}$~1–2 minutes) was similar to that of omithine decarboxylase, which is the most rapidly degraded protein previously known (Verma and Deshaies, *Cell* 101, 341–344, 2000). Thereby APOBEC3G is eliminated from cells that contain wild-type Vif (FIG. 5) and it is consequently absent from HIV-1 progeny virions that are produced by these cells (FIG. 6). Although additional investigations of the mechanism of Vif-induced degradation of APOBEC3G are necessary, the results presented here suggest that this pathway may involve ubiquitination. Specifically, large polyubiquitinated derivatives of APOBEC3G-Myc have been detected in amounts that are substantially increased by Vif and by the proteasome inhibitor ALLN (FIG. 11B). Since there is much less APOBEC3G-Myc in samples purified from the Vif-positive cultures (FIG. 11B), and since steady-state levels of APOBEC3G-Myc are very low in the cells that contain Vif (FIG. 5), the detected polyubiquitination must be extremely accelerated and efficient in the cells that are rapidly degrading APOBEC3G-Myc. Nevertheless, a relatively slow and inefficient process of APOBEC3G-Myc polyubiquitination also occurs in the absence of Vif.

Accordingly, we note that the SLQ(Y/F)LAΦΦΦΦ motif in Vif and the downstream proline-rich region is very similar to the BC-box sequence SLQYLC - - - Φ in human SOCS6 (suppresser of cytokine signaling) that also occurs in other proteins including the von Hippel-Lindau tumor suppressor (Kamura et al., *Genes Dev.* 12, 3872–3881, 1998). BC-box proteins associate with Elongins B and C and a cullin to target other proteins for ubiquitination and degradation (Iwai et al., *Proc. Natl. Acad. Sci. USA* 96, 12436–12441, 1999). This correspondence strongly supports the results presented here, and indicates that Vif may (without being bound to this proposed mechanism) function in association with these or related proteins as an E3 ubiquitin-protein isopeptide ligase. Interestingly, the HIV-1 encoded Vpu protein targets CD4 for degradation by a different ubiquitin-dependent pathway (Schubert et al., *J. Virol.* 72, 2280–2288, 1998; Margottin et al., *Mol. Cell.* 1, 565–574, 1998).

Additional considerations support these interpretations. Two Vif mutants (Δ12 and Δ31) that have overlapping deletions of the conserved SLQ(Y/F)LAΦΦΦΦ core sequence retain ability to bind APOBEC3G but have lost the capability for inducing its degradation (FIG. 8). This indicates that Vif binding to APOBEC3G is insufficient for neutralizing the antiviral phenotype and that the conserved core region of Vif then mediates the targeted degradation, as discussed above. A catalytic mechanism is also suggested by the observation that small amounts of Vif expression vectors suffice for efficient APOBEC3G elimination and that a pcDNA3.1-Vif vector that causes relatively little Vif expression also strongly down modulates APOBEC3G (FIG. 3). The concentration of Vif is unaffected by coexpression of APOBEC3G (FIGS. 3A and 3B), which also implies that Vif functions repetitively.

The conclusion that Vif eliminates APOBEC3G from cells is consistent with the studies of HIV-1 virions (see FIG. 5). Thus, in controlled studies APOBEC3G was reproducibly found to be absent from HIV-1 virions made in cells that contain Vif, whereas it occurs in HIV-1 virions purified from cells that lack Vif. Although the data do not establish whether the APOBEC3G-mediated attack on HIV-1(Δvif) occurs in nonpermissive producer cells, or later in virion particles, or in subsequently infected target cells, recent evidence supports the latter alternative (Lecossier et al., *Science* 300, 1112, 2003; Zhang et al., *Nature* 424, 94–98, 2003; Mangeat et al., Nature 424, 99–103, 2003; Harris et al., *Cell* 113, 803–809, 2003). Specifically, these reports indicate that APOBEC3G causes cytidine deamination of the negative DNA strand during reverse transcription in the target cells. Therefore, we believe that the Vif-induced elimination of APOBEC3G from virus-producing cells and thereby from progeny virions is the primary mechanism for control of viral infectivity in nonpermissive cells.

These results are encouraging from a drug development perspective, because they indicate that Vif has a conserved core with an SLQ(Y/F)LAΦΦΦΦ motif that mediates APOBEC3G degradation. The conservation of this core during lentiviral evolution (Oberste & Gonad, *Virus Genes* 6, 95–102, 1992) suggests that it has been difficult to mutate without loss of viral fitness, implying that drug escape mutants might have low replicative efficiencies. Moreover, APOBEC3G is clearly a grave threat to HIV-1 as indicated by its need for the vif gene (Gabuzda et al., *J. Virol.* 66, 6489–6495, 1992; von Schwedler et al., *J. Virol.* 67, 4945–4955, 1993; Desrosiers et al., *J. Virol.* 72, 1431–1437, 1998). Consequently, drug selection strategies focused on the binding and degradative processes described are provided herein.

Example 2

Cell-Based System Capable of Identifying Inhibitors of Vif-Mediated APOGEC3G Degradation This example provides an additional APOBEC3G fusion protein, YFP-APOBEC3G (SEQ ID NO: 4), and demonstrates its use in a cell-based system for use in methods of identifying inhibitors of Vif-mediated APOBEC3G degradation.

Using methods essentially similar to those described in Example 1, a vector was constructed that encodes a chimeric protein containing the yellow fluorescent protein (YFP) at the amino terminus and APOBEC3G at the carboxyl terminus (YFP-APOBEC3G; SEQ ID NOs: 3 and 4). Cotransfection of plasmids that encode this chimera and Vif into human 293T cell cultures results in only a few fluorescent cells, consistent with a Vif-induced degradation (FIG. 13A, top two panels). In contrast, cotransfection with a vector lacking Vif results in a much larger fraction of fluorescent cells. Moreover, treatment of the culture that contains Vif and YFP-APOBEC3G with a proteasome inhibitor such as ALLN reverses the Vif-dependent elimination of the chimeric protein and causes cells in the Vif-containing culture to accumulate YFP-APOBEC3G, thereby causing the percentage of APOBEC3G-positive cells to increase.

This cell based system can be used in examples of the herein described screening strategies. A cell culture is produced that expresses an easily measured or detected protein that will become degraded and eliminated by Vif (here, the YFP-APOBEC3G fusion protein). Anything that blocks or reduces the Vif-mediated degradation pathway, or that interferes with Vif synthesis, would cause the culture to express greatly elevated amounts of the easily measured protein, as in this case with YFP. The results shown in FIG. 13 demonstrate that the method is feasible, and that the proteasome inhibitor ALLN blocks Vif-mediated elimination of YFP-APOBEC3G from the cultured cells. Thus, proteasome inhibitors are one expected category of molecules that may be identified using the methods described herein.

Example 3

Rapid Binding Assay to Detect Vif-APOBEC3G Association

This example provides a description of one method for detecting the binding or association of Vif with APOBEC3G.

Figure 13:
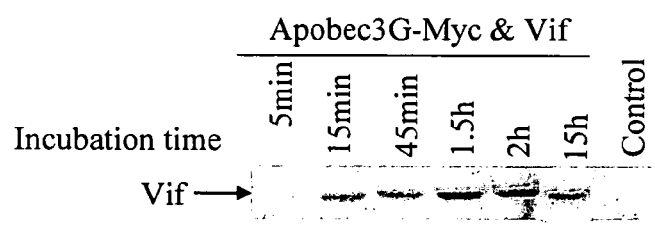
FIG. 13 shows that Vif rapidly binds to Ni-NTA-agarose beads with adsorbed APOBEC3G-Myc. APOBEC3G-Myc attached onto beads or other surfaces actively adsorbs Vif from solution. The blot shows a time course for the binding at 0° C. of either wild-type Vif (SEQ ID NO: 10) or Vif(Δ12) (SEQ ID NO: 12), which has a deletion mutation that eliminates the conserved SLQ(Y/F)LA BC-box motif in the Vif protein. Both Vif proteins bind strongly and rapidly to APOBEC3G-Myc. In contrast, control beads lacking APOBEC3G-Myc do not bind Vif. Control: Vif but no APOBEC3G.

APOBEC3G-Myc attached onto beads (results shown) or other surfaces (results not shown) actively adsorbs Vif from solution. FIG. 13 shows the results of using this as a rapid binding assay to detect Vif-APOBEC3G association. 293T cultures were transiently transfected or cotransfected with either pcDNA3.1APOBEC3G-Myc-His, pHIVgptWT, or pHIVgptΔvif and pcDNA3 Δ12 Vif. Thirty-six hours post-transfection, cells transiently expressing APOBEC3G-Myc-His were lysed in RIPA buffer (50 mM Tris-Cl (pH 7.4), 1% Nonidet P40, 0.1% sodium deoxycholate, 150 mM NaCl) and 350 μl of lysate was combined with 70 μl of Ni-NTA agarose (Qiagen, Chatsworth, Calif.) and rotated at 4° C. for 4 hours. APOBEC3G-Myc-His bound to Ni-NTA agarose was washed three times in 300 μl RIPA buffer to remove all unbound proteins. Cultures transiently expressing HIVgptWT or co-expressing HIVgptΔvif and Δ12 Vif were lysed in RIPA buffer. The protein content of these lysates was normalized using Bradford Reagent assay (BioRad Laboratories). An aliquot of 350 μl of normalized lysate was added to Ni-NTA agarose bound to APOBEC3G-Myc-His (lanes #1–6) or to Ni-NTA agarose that was previously incubated with untransfected 293T cell lysate (control lane #7) and rotated at 4° C. for indicated incubation times. Following incubation, Ni-NTA agarose was washed immediately three times with 300 μl RIPA buffer and Ni-NTA agarose beads were resuspended in 45 μl 2× Laemmli sample buffer. Ni-NTA precipitated samples were heat denatured at 95° C. for 5 minutes and equal volumes were loaded onto a 10% SDS-PAGE gel for Western blot analysis with rabbit anti-Vif antiserum #2221 (NIH AIDS Research and Reference Reagent Program, Division of AIDS, NIAID, NIH, contributed by Dr. D. Gabuzda). The figure shows a time course for the binding at 4° C. of either wild-type Vif (SEQ ID NO: 8) or Vif(Δ12) (SEQ ID NO: 10), which has a deletion mutation that eliminates the conserved SLQ(Y/

F)LA BC-box motif in the Vif protein. Both Vif proteins bind strongly and rapidly to APOBEC3G-Myc. In contrast, control beads lacking APOBEC3G-Myc do not bind Vif.

This and related assays such as ELISA assays can be used to detect Vif-APOBEC3G binding. Drugs that interfere with the binding can be identified and characterized using this and related assays, as explained herein.

Example 4

General Approach to Screening for Anti-Lentiviral Drugs

Now that it is known that APOBEC3G is a target of Vif, and that APOBEC3G/Vif interaction (either direct or indirect) is a component in the inhibition of a cell's antiviral response, screening tests can be used to screen for, analyze, and characterize compounds that interfere with this interaction.

In one embodiment, APOBEC3G (or a variant or analog or fusion protein) is attached to a matrix, or introduced into wells of a microtiter plate. Extracts that contain normal or modified forms of Vif are incubated with the matrices or plates, and the Vif protein adsorbs onto the APOBEC3G but not onto control matrices or wells that lack APOBEC3G. After washing away the unabsorbed Vif, the matrices or plates are analyzed by standard methods such as ELISA for detection of the adsorbed Vif. The assay can be done in the reverse manner also, by attaching the Vif and by measuring the adsorption of APOBEC3G or a derivative thereof.

Drug candidates are added to the assay wells, to determine whether any agent, such as a chemical compound, antibody or peptide, blocks binding of Vif to the matrices or plates that contain APOBEC3G (or a variant or analog or fusion protein). The assays could also be done inversely, by binding Vif and by studying the adsorption of APOBEC3G (or its variants, isoform or homologues or fusion proteins) onto the immobilized Vif. Such assays can also be performed with small fragments of APOBEC3G that contain only the domain needed for Vif binding. Optionally, cell extract can be included in the incubation, in order to enable the interaction of additional protein(s) or other factors that may influence or mediate the interaction between Vif and APOBEC3G.

Similarly, assays for Vif-APOBEC3G interactions can be investigated using intact cells. For example, a yeast two-hybrid assay or the inverse two-hybrid assay method of Schreiber and coworkers (*Proc. Natl. Acad. Sci., USA* 94:13396, 1977) can be used to screen for a drug that disrupts the Vif-APOBEC3G association. Since Vif mediates the degradation of APOBEC3G by a pathway that requires their binding, any compound that blocks Vif association with APOBEC3G in the two-hybrid assay (whether the interaction is direct or indirect) would be expected to restore normal levels and/or functions of APOBEC3G within lentiviral infected mammalian cells, as discussed herein. Therapeutic agents identified by these or other approaches are tested for inhibitory effects of lentivirus replication, for instance, HIV-1 replication in human lymphocytes.

Therapeutic agents identified with these or other approaches, including the specific assays and screening systems described herein, are used as lead compounds to identify other agents having even greater antiviral activity. For example, chemical analogs of identified chemical entities, or variant, fragments of fusions of peptide agents, are tested for their activity in the assays described herein.

Candidate agents also can be tested in virus-infected cultures to determine whether they inhibit lentivirus replication and/or infection. The agents also can be tested for safety in animals, and then used for clinical trials in animals or humans. Since any compound that blocks Vif would be expected to inhibit infectivity of wild-type lentivirus released from NP cells, but would have no effect on the titer of virus made in P cells, P cells can be used as controls to identify nonspecific effects of the drug or agent on cell growth or viability, or on lentiviral encoded proteins other than Vif.

Examples of agents that interfere with an indirect or direct interaction of Vif and APOBEC3G, identified using assays provided herein, include: chemical compounds; fragments and fusions of Vif; peptidomimetics; antibodies; synthetic ligands that bind Vif, agents which cause the disassociation of Vif from one or more components of the Vif-mediated APOBEC3G degradation pathway; APOBEC3G fragments, or other fragments of natural or synthetic ligands or chemical compounds that bind to Vif and prevent the interaction of Vif and APOBEC3G (or another component of the pathway), and thereby affect lentivirus virus replication. The determination and isolation of ligand/compositions is well described in the art. See, e.g., Lerner, *Trends NeuroSci.* 17:142–146, 1994.

Example 5

Screening Assays for Molecules that Inhibit Direct Binding

Rapid screening assays can be used to screen a large number of agents to determine if they bind to Vif or APOBEC3G (prescreening agents), or if they disrupt a binding between Vif and APOBEC3G directly. Rapid screening assays for detecting binding to HIV proteins have been disclosed, for example in U.S. Pat. No. 5,230,998, which is incorporated by reference. In that assay, Vif or APOBEC3G is incubated with a first antibody capable of binding to Vif or APOBEC3G, and the agent to be screened. Excess unbound first antibody is washed and removed, and antibody bound to the Vif or APOBEC3G is detected by adding a second labeled antibody which binds the first antibody. Excess unbound second antibody is then removed, and the amount of the label is quantitated. The effect of the binding effect is then determined in percentages by the formula:

(quantity of the label in the absence of the drug)–
(quantity of the label in the presence of the
drug/quantity of the label in the absence of the
drug)×100

If prescreening is used, agents that are found to have a high binding affinity to the Vif or APOBEC3G can then be used in other assays more specifically designed to test inhibition of the Vif/APOBEC3G interaction, or inhibition of viral replication.

Whether or not this prescreening step is used, a cell or sample containing both an APOBEC3G and a Vif is contacted with the test agent. The sample is then subjected to molecular assay(s) to evaluate the interaction of APOBEC3G and Vif. An example of such an assay is an ELISA, GST-pull down assay, Western blot or a co-immunoprecipitation assay. By way of example, the interaction is measured using antibodies that bind either APOBEC3G or Vif. In one embodiment, the interaction of Vif and APOBEC3G in a cell or sample contacted with a test agent is compared to a control value. Control values can be obtained, for example, using a reference standard, or the binding of Vif/APOBEC3G in a cell or sample not contacted with a test agent.

In another embodiment, an assay is performed on a sample including purified Vif and APOBEC3G in vitro. Purified Vif and APOBEC3G are contacted with the agent, and the interaction of Vif and APOBEC3G is assayed. The interaction of APOBEC3G and Vif in the presence of the agent may be compared to a control, such as a reference standard, or a sample including purified Vif and APOBEC3G in the absence of the agent.

In each case, an agent that is determined to reduce the binding/interaction between an APOBEC3G and a Vif is identified as having the potential to be useful in inhibition of viral replication or disease. Agents so identified can beneficially subjected to further testing and characterization.

Example 6

Test Agents

Test agents used in assays and screening methods described herein may be obtained from a combinatorial library for screening a plurality of compositions/ligands. Agents identified from the library are further evaluated, detected, cloned, sequenced, and the like, either in solution or after binding to a solid support, by any method usually applied to the detection of a specific DNA sequence, such as PCR, oligomer restriction (Saiki et al., *Bio/Technology*, 3:1008–1012, 1985), allele-specific oligonucleotide (ASO) probe analysis (Conner et al., *Proc. Natl. Acad. Sci. USA*, 80:278, 1983), oligonucleotide ligation assays (OLAs) (Landegren et al., *Science*, 241:1077, 1988), and the like.

Any of a variety of procedures may be used to clone genes of interest when the test composition is expressed as a gene product in a combinatorial library (as opposed to a chemical composition). One such method entails analyzing a shuttle vector library of DNA inserts (derived from a cell which expresses the composition) for the presence of an insert which contains the gene. For example, cells are transfected with the vector, and then assayed for expression of the product of interest. The preferred method for cloning these genes entails determining the amino acid sequence of the composition protein, for example by purifying the desired protein and analyzing it with automated sequencers.

The proteins can be extracted and purified from the culture media or a cell by using known protein purification techniques, such as extraction, precipitation, ion exchange chromatography, affinity chromatography, gel filtration and the like. The therapeutic proteins can be isolated by affinity chromatography, for example taking advantage of a binding interaction between the protein and Vip to isolate the protein of interest.

The therapeutic agents that are isolated using these approaches can have a variety of mechanisms of action. For example, the agent can be a chemical compound that binds to Vif and prevents or decreases an interaction (direct or indirect) between Vif and APOBEC3G. Alternatively, the chemical compound binds to or inhibits an activity of APOBEC3G so that APOBEC3G is not subject to an interaction with Vif, or is not degraded or targeted for degradation by Vif, but continues to perform an anti-viral function against HIV or other lentiviruses. Other useful agents will bind APOBEC3G in a target cell, to prevent or inhibit the interaction of APOBEC3G with Vif, while still maintaining an anti-viral activity of APOBEC3G. Other agents will bind Vif in a target cell and prevent or inhibit the interaction of APOBEC3G with Vif, without affecting the anti-viral activity of APOBEC3G. Assays can be designed to assess each of these activities in the cell, or all of them at once, to screen for therapeutically useful compounds.

However, the specific mechanism of action of the agent need not even be known, as long as the agent inhibits or blocks HIV or other lentiviral replication or infectivity. Inhibition of HIV replication can be determined, for example, by evaluating the production of p24 protein or envelope mediated cell fusion, or using a reverse transcriptase assay (e.g., see Platt et al., *J. Virol.* 71: 883–890, 1997; Kozak et al., *J. Virol.* 71: 873–882, 1977). The replication of the immunodeficiency virus in a cell or cell culture or subject contacted with the agent is compared to a control, such as a cell (or culture, or subject) not contacted with the agent, or a pre-determined standard value.

Agents identified by the assays described herein may be selected for further study if, for example, they show a statistically different result from a control. For example, when the assay is a reverse transcriptase assay, a student's T-test is used to compare the values obtained in the assay with the control values. A statistically significant result is then considered to be one in which $p<0.05$.

The assays are also useful to identify agents useful in the study of HIV infection, for example labeled agents that bind to Vif and APOBEC3G, or to another component of the Vif-mediated APOBEC3G degradation pathway. In addition, the assay can identify candidate agents for inhibiting or stimulating HIV-induced cytokine production, or for studying HIV replication. For example, the identified agents could be used in vitro to block or to enhance HIV replication. Thus, the assays described herein identify new pharmaceutical or laboratory compositions comprising isolated and purified agents that interfere with the interaction of Vif and APOBEC3G.

Example 7

Peptide Agents to Inhibit Viral Replication

Pharmaceutical agents developed for the treatment of lentiviral infections are often organic chemical entities that are more conveniently administered to subjects, and which survive oral administration and first pass hepatic inactivation. However an increasingly important type of therapeutic agent is a peptide based drug, for example a fragment of Vif or APOBEC3G that binds or blocks a (direct or indirect) interaction between a Vif and APOBEC3G, or between one of these and another component of the Vif-mediated APOBEC3G degradation pathway, but does not have the biological function of Vif or APOBEC3G. In some embodiments, derivatives, analogs, and mutants of Vif or APOBEC3G are screened to assess the presence of this function.

Particular examples of such peptides are APOBEC3G fragments, fusions or variants (including analogs, homologs, derivatives, muteins and mimetics) that bind Vif, and do not have a biological activity of APOBEC3G, and/or do not interfere with a function of intact APOBEC3G in the cell. Other examples are Vif fragments, fusions or variants (including analogs, homologs, derivatives, muteins and mimetics) that bind APOBEC3G and prevent the binding of intact Vif to APOBEC3G, but do not target APOBEC3G to degradation by the proteasome or through another system, or interfere with a function of intact APOBEC3G in the cell. Any fragments, variants or fusions of Vif and APOBEC3G may be used as long as they influence (e.g., inhibit) the replication of a lentivirus (such as HIV) in a cell or cell culture or animal, or inhibit the direct or indirect interaction of Vif and APOBEC3G, but do not significantly or detrimentally interfere with a biological activity of APOBEC3G.

Minor modifications of the APOBEC3G primary amino acid sequence may result in proteins that can bind Vif with a different affinity, as compared to the unmodified counterpart polypeptide. Such modifications can be made deliberately by site-directed mutagenesis, or may be spontaneous. In one embodiment, a variant of APOBEC3G is a protein having at least 80%, 90%, 95%, or 99% sequence identity to APOBEC3G, and which retains the ability to bind to Vif, but without losing its anti-viral activity. In another example, the variant has higher than normal binding affinity to Vif or a component in the Vif-mediated APOBEC3G degradation pathway, such that it is preferentially bound, thereby interfering with Vif-mediated degradation of endogenous APOBEC3G.

Variants and fragments also can be created by recombinant techniques employing genomic or cDNA cloning methods. Site-specific and region-directed mutagenesis techniques can be employed. See *Current Protocols in Molecular Biology* vol. 1, ch. 8, Ausubel et al., eds., J. Wiley & Sons 1989 & Supp. 1990–93; *Protein Engineering*, Oxender & Fox eds., A. Liss, Inc., 1987. In addition, linker-scanning and PCR-mediated techniques can be employed for mutagenesis. See *PCR Technology*, Erlich ed., Stockton Press, 1989; *Current Protocols in Molecular Biology*, vols. 1 & 2. Protein sequencing, structure and modeling approaches for use with any of the above techniques are disclosed in *Protein Engineering, loc. cit*., and *Current Protocols in Molecular Biology*, vols. 1 & 2.

Non-peptide compounds that mimic the binding and function of APOBEC3G ("mimetics") can be produced, for instance, by the approach outlined in Saragovi et al., *Science* 253: 792–95, 1991. Mimetics are molecules which mimic elements of protein secondary structure. See, for example, Johnson et al., "Peptide Turn Mimetics," in *Biotechnology and Pharmacy*, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions.

Peptides based therapeutics can be administered as nucleic acids that express the peptide. For example, a therapeutic polynucleotide is introduced into cells infected with, or at risk of infection with, a lentivirus. The therapeutic polynucleotide may encode any of the therapeutic peptides described, or others having the provided characteristics. The therapeutic polynucleotides include sequences that are degenerate as a result of the degeneracy of the genetic code. Such polynucleotides are operatively linked to a promoter sequence that facilitates the efficient transcription of the inserted genetic sequence of the host. An expression vector used to express a therapeutic polynucleotide typically contains an origin of replication, a promoter, as well as specific gene(s) that allow phenotypic selection of the transformed cells. Vectors suitable for use in the present invention include, but are not limited to the pMSXND expression vector for expression in mammalian cells (Lee and Nathans, *J. Biol. Chem.* 263:3521, 1988) and retrovirus derived vectors. The DNA segment can be present in the vector operably linked to regulatory elements, for example, a promoter (e.g., immunoglobulin, T7, metallothionein I, or polyhedron promoters).

Delivery of the therapeutic polynucleotide can be achieved using a recombinant expression vector such as a chimeric virus or a colloidal dispersion system. Delivery can also be achieved with the use of targeted liposomes. Various viral vectors which can be utilized for the introduction of nucleic acids in a cell as taught herein include adenovirus, herpes virus, vaccinia, or an RNA virus such as a retrovirus. In one embodiment, the vector is a retroviral vector derived from a murine or avian retrovirus. Examples of retroviral vectors in which a single foreign gene can be inserted include, but are not limited to: Maloney murine leukemia virus (MoMuLV), Harvey murine sarcoma virus (HaMuSV), murine mammary tumor virus (MuMTV), and Rous Sarcoma Virus (RSV). When the subject is a human, a gibbon ape leukemia virus (GaLV) or an amphotropic MoMuLv is utilized.

A number of additional retroviral vectors can incorporate multiple genes. By inserting a sequence encoding a fragment or fusion or mutant Vif or APOBEC3G polypeptide, or other therapeutic polypeptide, into the viral vector, along with another gene that encodes the ligand for a receptor on a specific target cell, the vector becomes target specific. Retroviral vectors can be made target-specific by attaching, for example, a sugar, a glycolipid, or a protein. Targeting is also accomplished by using an antibody to target the retroviral vector.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. In one embodiment, the colloidal system is a liposome. RNA, DNA and intact virions can be encapsulated within the aqueous interior and be delivered to cells in a biologically active form (Fraley et al., *Trends Biochem. Sci.* 6:77, 1981). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Example 8

Screening Assays for Compounds that Modulate APOBEC3 Expression or Activity

The following additional assays are designed to identify compounds that interact with (e.g., bind to) an APOBEC3G or a variant thereof (including, but not limited to a fusion protein that contains all or part of APOBEC3G with an indicator molecule, such as GFP or another detectable marker), compounds that interact with (e.g., bind to) intracellular proteins that interact with APOBEC3G (including, but not limited to, proteins involved in mediating interactions between APOBEC3G and Vif, or component(s) of cellular mechanisms responsible for transporting or targeting such a complex to the proteasome), compounds that interfere with the interaction of a APOBEC3G with transmembrane or intracellular proteins involved in signal transduction, and to compounds which modulate the activity of a APOBEC3G gene (i.e., modulate the level of gene expression) or modulate the level of activity of a variant form of or fusion comprising an APOBEC3G. Assays may additionally be utilized which identify compounds that bind to APOBEC3G gene regulatory sequences (e.g., promoter sequences) and which may or influence APOBEC3G expression and thereby its interaction with Vif. See, e.g., Platt, *J Biol Chem* 269:28558–28562, 1994.

The compounds that may be screened in accordance with the disclosure include, but are not limited to peptides, antibodies and fragments thereof, and other organic compounds (e.g., peptidomimetics, small molecules) that influence Vif-mediated degradation of APOBEC3G. Such compounds, as identified by the methods described herein, may bind to or interact with APOBEC3G directly, Vif directly, or a component of the Vif-mediated APOBEC3G degradation pathway as described herein, and thereby influence the Vif-mediated degradation of APOBEC3G.

Such compounds may include, but are not limited to, peptides such as, for example, soluble peptides, including but not limited to members of random peptide libraries; (see, e.g., Lam et al., *Nature* 354:82–84, 1991; Houghten et al., *Nature* 354:84–86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell* 72:767–778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), and small organic or inorganic molecules.

Other compounds that can be screened in accordance with the disclosure include but are not limited to small organic molecules that are able to gain entry into an appropriate cell and affect the Vif-mediated APOBEC3G degradation pathway (e.g., by interacting with the regulatory region or transcription factors involved in gene expression in that pathway); or such compounds that affect the activity of APOBEC3G or the activity of some other intracellular factor involved in the Vif-mediated APOBEC3G degradation pathway.

Computer modeling and searching technologies permit identification of compounds, or the improvement of already identified compounds, that can modulate expression or activity of a component of the Vif-mediated APOBEC3G degradation pathway. Having identified such a compound or composition, the active sites or regions mediating its effect(s) can be identified. Such active sites might typically be binding sites, such as the interaction domain(s) between Vif or APOBEC3G and a component of the pathway, or between other components of the pathway.

The active site can be identified using methods known in the art including, for example, from the amino acid sequences of peptides, from the nucleotide sequences of nucleic acids, or from study of complexes of the relevant compound or composition with the component(s) of the pathway. In the latter case, chemical methods can be used to find the active site by finding where on the component the complexed compound is found. Next, the three dimensional geometric structure of the active site is determined. This can be done by known methods can determine a complete molecular structure. On the other hand, solid or liquid phase NMR can be used to determine certain intra-molecular distances. Any other experimental method of structure determination can be used to obtain partial or complete geometric structures, such as high resolution electron microscopy. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, additional candidate modulating compounds can be identified by searching databases containing compounds along with information on their molecular structure. Such a search seeks compounds having structures that match the determined active site structure and that interact with the group(s) defining the active site. Such a search can be manual, but is preferably computer assisted. Compounds found from such a search are potential therapeutic compounds, for use in influencing and affecting the Vif-mediated degradation of APOBEC3G.

Alternatively, these methods can be used to identify improved modulating compounds from an already known modulating compound or ligand. The composition of the known binding compound can be modified and the structural effects of modification can be determined using the experimental and computer modeling methods described herein, applied to the new composition. The altered structure is then compared to the binding/active site structure of the compound to determine if an improved fit or interaction results, and/or it can be tested in one of the model systems described herein. In this manner systematic variations in composition, such as by varying side groups, can be quickly evaluated to obtain modified modulating compounds or ligands of improved specificity or activity.

Further experimental and computer modeling methods useful to identify potential therapeutic compounds based upon identification of binding/active sites within the Vif-mediated APOBEC3G degradation pathway will be apparent to those of ordinary skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al. *Acta Pharmaceutical Fennica* 97:159–166, 1988; Ripka, *New Scientist* 54–57, 1988; McKinaly and Rossmann, *Annu Rev Pharmacol Toxicol* 29:111–122, 1989; Perry and Davies, *OSAR: Quantitative Structure-Activity Relationships in Drug Design* pp. 189–193, 1989 (Alan R. Liss, Inc.); Lewis and Dean, *Proc R Soc Lond* 236:125–140 and 141–162, 1989; and, with respect to a model receptor for nucleic acid components, Askew et al., *J Am Chem Soc* 111: 1082–1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding between two or more components of the Vif-mediated APOBEC3G degradation pathway, one could also screen libraries of known compounds, including natural products or synthetic chemicals, and biologically active materials, including proteins, for compounds which are inhibitors or activators of the pathway.

Compounds identified via assays such as those described herein may be useful, for example, in influencing the Vif-mediated APOBEC3G degradation pathway, for instance in order to influence viral infection and/or replication.

Example 9

In Vitro Screening Assays for Compounds that Bind to APOBEC3G and/or Vif

In vitro systems may be designed to identify compounds capable of interacting with (e.g., binding to) any component of the Vif-mediated APOBEC3G degradation pathway, including Vif and/or APOBEC3G. At least some of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly.

The principle of assays used to identify compounds that bind to a component of the Vif-mediated APOBEC3G degradation pathway (for instance, Vif or APOBEC3G) involves preparing a reaction mixture of the component polypeptide and a test compound under conditions and for a time sufficient to allow the two to interact and bind, thus forming a complex that can be removed from and/or detected in the reaction mixture. The component polypeptide used can vary depending upon the goal of the screening assay. For example, where agonists or antagonists are sought, the full length pathway component (such as APOBEC3G or Vif), or a truncated version thereof, which contains a domain of the component known or believed to interact with another component(s) of the pathway, or a fusion protein (such as one that comprises a protein, polypeptide or other added element that provides an advantage to the assay system, such as for identifying or isolating the resultant complex), can be employed.

The in vitro screening assays can be conducted in a variety of ways. For example, the pathway component (such as APOBEC3G or Vif), fragment, or fusion protein, or the test compound(s), could be anchored onto a solid phase. In this embodiment, pathway component/test compound complexes are captured on the solid phase at the end of the reaction, and the complex is detected and/or measured on the solid surface or after being removed therefrom. In one embodiment of such a method, the pathway component is anchored onto a solid surface, and the test compound(s), which is not anchored, may be labeled, either directly or indirectly, so that its capture by the component on the solid surface can be detected. In other examples, the test compound(s) are anchored to the solid surface, and the pathway component, or fragment or fusion protein, which is not anchored, is labeled or in some way detectable.

In practice, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any specific complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components. The complexes can be detected, for instance, using an immobilized antibody specific for the pathway component protein, fragment polypeptide, or fusion protein, or the test compound, to anchor or capture from the solution any complexes formed in solution. A labeled antibody specific for the other component of the possible complex then can be used to detect anchored/captured complexes.

Alternatively, cell-based assays, membrane vesicle-based assays and membrane fraction-based assays can be used to identify compounds that influence interactions in the Vif-mediated APOBEC3G degradation pathway. To this end, cell lines that express a Vif or APOBEC3G, or a fusion protein containing a domain or fragment of such protein (or a combination thereof), or cell lines (e.g., COS cells, CHO cells, HEK293 cells, etc.) that have been genetically engineered to express such protein(s) or fusion protein(s) (e.g., by transfection or transduction of APOBEC3G or Vif DNA) can be used. Test compound(s) that influence the degradation pathway for example, can be detected by monitoring a change in the level or amount or turnover rate of APOBEC3G or a fusion protein containing a domain or fragment thereof.

Example 10

Assays for Intracellular Proteins that Interact with APOBEC3G and/or Vif

Also contemplated herein are methods for identifying additional components of the pathway(s) involved in Vif-mediated degradation of ABOBEC3G. Such methods may involve, for instance, assays to detect and identify intracellular proteins that interact within this such pathway, for instance, proteins that directly or indirectly interact with APOBEC3G or Vif. In some embodiments, it is contemplated that such proteins can themselves be used to influence (e.g., inhibit) viral infectivity and replication in a cell culture or subject, or used to develop compounds useful for such inhibition.

Any method suitable for detecting protein-protein interactions may be employed for identifying transmembrane or intracellular proteins that interact with Vif or APOBEC3G. Among traditional methods that may be employed are co-immunoprecipitation, cross-linking and co-purification through gradients or chromatographic columns of cell lysates or proteins obtained from cell lysates to identify proteins in the lysate that interact with the target (e.g., Vif, APOBEC3G, or a fragment thereof). For such assays, the target component used can be a full length protein (e.g., Vif or APOBEC3G), a fragment thereof, a peptide corresponding to a region of such protein that mediates an interaction (direct or indirect) between Vif and APOBEC3G, and so forth.

Once isolated, such an intracellular or transmembrane protein can be identified and can, in turn, be used, in conjunction with standard techniques, to identify proteins with which it interacts. For example, at least a portion of the amino acid sequence of an intracellular protein which interacts with APOBEC3G (or another target) can be ascertained using techniques well known to those of skill in the art, such as via the Edman degradation technique. See, e.g., Creighton *Proteins: Structures and Molecular Principles*, W. H. Freeman & Co., N.Y., pp. 34–49, 1983. The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well known. See, e.g., Ausubel et al. *Current Protocols in Molecular Biology* Green Publishing Associates and Wiley Interscience, N.Y., 1989; and Innis et al., eds. *PCR Protocols: A Guide to Methods and Applications* Academic Press, Inc., New York, 1990.

Additionally, methods may be employed in the simultaneous identification of genes that encode the transmembrane or intracellular protein(s) interacting with a target in the Vif-mediated APOBEC3G degradation pathway. These methods include, for example, probing expression libraries, in a manner similar to the well known technique of antibody probing of λgt11 libraries, using labeled APOBEC3G protein, or another polypeptide, peptide or fusion protein, e.g., a variant APOBEC3G polypeptide or APOBEC3G domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One example of this system has been described (Chien et al., *PNAS USA* 88:9578–9582, 1991) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to an APOBEC3G nucleotide sequence encoding APOBEC3G, a variant APOBEC3G polypeptide, peptide or fusion protein, and the other plasmid consists of nucleotides encoding the transcription activator protein's activation domain fused to a cDNA (or collection of cDNAs) encoding an unknown protein(s) that has been recombined into the plasmid as part of a cDNA library. The DNA-binding domain fusion plasmid and the activator cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or other such methodology may be used to screen activation domain libraries for proteins that interact with the "bait" gene product. By way of example, and not by way of limitation, APOBEC3G may be used as the bait gene product. Total genomic or cDNA sequences are fused to the DNA encoding an activation domain. This library and a plasmid encoding a hybrid of a bait APOBEC3G gene product fused to the DNA-binding domain are cotransformed into a yeast reporter strain, and the resulting transformants are screened for those that express the reporter gene. For example, and not by way of limitation, a bait APOBEC3G gene sequence, such as the open reading frame of APOBEC3G (or a domain of APOBEC3G, such as a domain involved in mediating it degradation by Vif) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait APOBEC3G gene product are to be detected can be made using methods routinely practiced in the art. For example, the cDNA fragments can be inserted into a vector such that they are translationally fused to the transcriptional activation domain of GAL4. This library can be co-transformed along with the bait APOBEC3G gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait APOBEC3G gene product will reconstitute an active GAL4 protein and thereby drive expression of the HIS3 gene. Colonies, which express HIS3, can be detected by their growth on Petri dishes containing semi-solid agar based media lacking histidine. The cDNA can then be purified from these strains, and used to produce and isolate the bait APOBEC3G gene-interacting protein using techniques routinely practiced in the art.

Example 11

Pharmaceutical Preparations and Methods of Administration

Therapeutic compound(s) can be administered directly to the mammalian subject for control of viral infection or replication, in vivo. Administration is by any of the routes normally used for introducing a compound into ultimate contact with the tissue to be treated. The compounds are administered in any suitable manner, optionally with pharmaceutically acceptable carrier(s). Suitable methods of administering therapeutic compounds, particularly for the control of viral infection or replication, are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17th ed. 1985).

Formulations suitable for administration include aqueous and non-aqueous solutions, isotonic sterile solutions (which can contain antioxidants, buffers, bacteriostats, and solutes that render the formulation isotonic), and aqueous and non-aqueous sterile suspensions (which can include suspending agents, solubilizers, thickening agents, stabilizers, and preservatives). By way of example, compositions can be administered, for example, orally. The formulations of compounds can be presented in unit-dose or multi-dose sealed containers, such as ampoules and vials. Solutions and suspensions can be prepared from sterile powders, granules, and tablets of the kind previously described.

The disclosure also contemplates various pharmaceutical and laboratory compositions that inhibit or block lentivirus, such as immunodeficiency virus, infection. The compositions are prepared using an agent that blocks or inhibits to a measurable degree the Vif-mediated degradation of APOBEC3G, such as a chemical or other compound; a mimetic; an isolated and purified peptide fragment of Vif; an isolated and purified peptide fragment of APOBEC3G; or a nucleic acid sequence encoding such a protein or peptide.

When the agent is to be used as a pharmaceutical, the agent is placed in a form suitable for therapeutic administration. The agent may, for example, be included in a pharmaceutically acceptable carrier such as excipients and additives or auxiliaries, and administered to a subject. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, nontoxic excipients, including salts, preservatives, buffers and the like, as described, for instance, in *Remington's Pharmaceutical Sciences,* 15th ed., Easton: Mack Publishing Co., 1405–1412, 1461–1487, 1975, and *The National Formulary XIV,* 14th ed., Washington: American Pharmaceutical Association, 1975). The pH and exact concentration of the various components of the pharmaceutical composition are adjusted according to routine skills in the art. *See Goodman and Gilman The Pharmacological Basis for Therapeutics,* 7th ed.

The pharmaceutical compositions are in general administered topically, intravenously, orally or parenterally or as implants. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampoule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science,* 249:1527–1533, 1990, which is incorporated herein by reference.

These and other compositions can be used to treat lentiviral infections, such as HIV disease and AIDS, by blocking replication of an immunodeficiency virus. This method involves administering to a subject a therapeutically effective dose of a pharmaceutical composition containing the compounds of the present invention and a pharmaceutically acceptable carrier. The administration of the pharmaceutical composition of the present invention may be accomplished by any means known to the skilled artisan (for example, intravenous, subcutaneous, intra-peritoneal, topical, intranasal, or oral administration). The pharmaceutical compositions may be administered locally or systemically.

For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units, and also by multiple administration of subdivided doses at specific intervals.

Initial dosage ranges can be selected to achieve an inhibitory concentration in target tissues that is similar to in vitro inhibitory tissue concentrations. The dosage should not be so large as to cause adverse side effects, such as unwanted cross-reactions, anaphylactic reactions, and the like. Generally, the dosage will vary with the age, condition, sex, and extent of the disease in the patient and can be determined by one skilled in the art. The dosage can be adjusted for each individual in the event of any contraindications and can be readily ascertained without resort to undue experimentation. In any event, the effectiveness of treatment can be determined by monitoring the viral load of a patient infected with the immunodeficiency virus. The viral load will decrease following administration of an effective agent. In one embodiment, the level of CD4+ T-cells is also monitored in the patient.

The dose administered to a patient, in the context of the present disclosure, should be sufficient to effect a beneficial response in the subject over time. The dose will be determined by the efficacy of the particular therapeutic compound employed and the condition of the subject, as well as the body weight or surface area or volume of the area to be treated. The size of the dose also will be determined by the existence, nature, and extent of any adverse side-effects that accompany the administration of a particular compound in a particular subject.

In determining the effective amounts of the therapeutic compound to be administered, a physician may evaluate circulating plasma levels of the compound, associated toxicities, and the production of antibodies to the compound or any degradation products thereof. In general, the dose equivalent of a therapeutic compound is from about 1 ng/kg to 10 mg/kg for a typical subject.

For administration, compounds identified by the methods described n can be administered at a rate determined by the $LD_{50}$ of the therapeutic compound, and the side effects of the compound at various concentrations, as applied to the mass and overall health of the subject. Administration can be accomplished via single or divided doses.

A therapeutically effective dose is the quantity of a compound according to the disclosure necessary to prevent, to cure or at least partially ameliorate the symptoms of a disease and its complications or to decrease the ability of an immunodeficiency virus to infect or replicate in a cell. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: the Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference. Effectiveness of the dosage can be monitored by any method (e.g., CD4+ count).

The pharmaceutical compositions of the disclosure, including chemical compounds, peptides, peptidomimetics, etc., are useful for treating subjects either having or at risk of having an immunodeficiency virus (e.g., HIV) related disorder, such as AIDS or ARC. For example, the compositions are useful for humans at risk for HIV infection, such as after rape or post-coitally. Application of the compounds is also useful to prevent maternal-fetal transmission of HIV. A "prophylactically effective" amount of an agent, for example, refers to that amount that is capable of measurable inhibiting HIV replication and/or infection.

The agent can also be administered in combination with one or more other drugs useful in the treatment of viral disease. For example, the compounds of this invention may be administered, whether before or after exposure to the virus, in combination with effective doses of other antivirals, immunomodulators, anti-infectives, or vaccines. The administration may be either concurrent or sequential administration of the active agents.

In one embodiment, a combination treatment uses an antiviral agent for the treatment of a retroviral disease, such as an HIV (e.g., HIV-1 or HIV-2), SIV or FIV induced disease. Examples of antiviral drugs that can be used for this purpose include: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo alto, Calif), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon labs, Inc. of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immunomodulators that can be used in combination with the composition are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, TNF (Genentech), and soluble TNF receptors (Immunex).

Examples of representative anti-infective agents used in the treatment of HIV, and that could be used in combination with the composition, include clindamycin with primaquine (from Upjohn, for the treatment of pneumocysti pneumonia), fluconazlone (from Pfizer for the treatment of cryptococcal meningitis or candidiasis), nystatin, pentamidine, trimethaprim-sulfamethoxazole, and many others.

"Highly active anti-retroviral therapy" or "HAART" refers to a combination of drugs which, when administered in combination, inhibits a retrovirus from replicating or infecting cells better than any of the drugs individually. In the treatment of HIV, an example of HAART is the administration of 3'axido-3-deoxy-thymidine (AZT) in combination with other agents. Other examples of HAART regimens include nucleoside analog reverse transcriptase inhibitor drugs (NA), non-nucleoside analog reverse transcriptase inhibitor drugs (NNRTI), and protease inhibitor drugs (PI). One specific, non-limiting example of HAART is a combination of indinavir and efavirenz, an experimental non-nucleoside reverse transcriptase inhibitor (NNRTI). The details of HAART undergo frequent evolution as new antiviral agents are found. The compositions described herein and/or identified by methods herein described, could be administered in conjunction with HAART.

Example 12

Knockout, Knock-In, and Overexpression Transgenic Animals

Mutant organisms that under-express or over-express one or more specific alleles of one or more specific APOBEC3G and/or Vif protein(s) are useful for research. Such mutants allow insight into the physiological and/or psychological role of APOBEC3G in a healthy and/or pathological organism, for instance during infection by a flavivirus. These "mutant organisms" are "genetically engineered," meaning that information in the form of nucleotides has been transferred into the mutant's genome at a location, or in a combination, in which it would not normally exist. Nucleotides transferred in this way are said to be "non-native." For example, a non-APOBEC3G promoter inserted upstream of a native APOBEC3G-encoding sequence would be non-native. An extra copy of a specific APOBEC3G gene on a plasmid, transformed into a cell, also would be non-native.

Mutants, for example, may be produced from mammals, such as mice or rats, that either express, over-express, or under-express a specific allelic variant or haplotype or diplotype of APOBEC3G (or a fusion protein comprising APOBEC3G), or that do not express APOBEC3G at all. Over-expression mutants are made by increasing the number of specified genes or encoding sequences in the organism, or by introducing a specific APOBEC3G allele or fusion protein into the organism under the control of a constitutive or inducible or viral promoter such as the mouse mammary tumor virus (MMTV) promoter or the whey acidic protein (WAP) promoter or the metallothionein promoter. Mutants that under-express APOBEC3G, or that do not express APOBEC3G, may be made by using an inducible or repressible promoter, or by deleting the APOBEC3G gene, or by destroying or limiting the function of the APOBEC3G gene, for instance by disrupting the gene by transposon insertion.

Antisense genes or molecules or related molecules (such as siRNAs) may be engineered into or provided to the organism, under a constitutive or inducible promoter, to decrease or prevent expression of APOBEC3G, as known to those of ordinary skill in the art.

A mutant mouse over-expressing a heterologous protein (such as a variant APOBEC3G protein or fusion protein comprising APOBEC3G) may be made by constructing a plasmid having a APOBEC3G (or fusion) encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

Tissue specific promoters are known. For instance, WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which the APOBEC3G gene is deleted, can be made by removing all or some of the coding regions of the gene from embryonic stem cells. Methods of creating deletion mutations by using a targeting vector have been described (see, for instance, Thomas and Capecchi, *Cell* 51:503–512, 1987).

In addition to knock-out systems, it is also beneficial to generate "knock-ins" that have lost expression of the native APOBEC3G protein but have gained expression of a different, usually mutant, fusion, or identified allelic form of the same protein. By way of example, the variant or fusion proteins provided herein can be expressed in a knockout background in order to provide model systems for studying the effects of these mutants. In particular embodiments, the resultant knock-in organisms provide systems for studying flaviviral infection and to identify and characterize compounds for the effects on such infection.

Those of ordinary skill in the relevant art know methods of producing knock-in organisms. See, for instance, Rane et al. (*Mol. Cell Biol.*, 22: 644–656, 2002); Sotillo et al. (*EMBO J.*, 20: 6637–6647, 2001); Luo et al. (*Oncogene*, 20: 320–328, 2001); Tomasson et al. (*Blood*, 93: 1707–1714, 1999); Voncken et al. (86: 4603–4611, 1995); Andrae et al. (*Mech. Dev.*, 107: 181–185, 2001); Reinertsen et al. (*Gene Expr.*, 6: 301–314, 1997); Huang et al. (*Mol. Med.*, 5: 129–137, 1999); Reichert et al. (*Blood*, 97: 1399–1403, 2001); and Huettner et al. (*Nat. Genet.*, 24: 57–60, 2000), by way of example.

Example 13

Animal Models for Lentiviral Infections

Animal models susceptible to lentiviral infection, such as HIV-1, are very useful for vaccine and drug development studies, and for understanding effects of the virus on the host immune system. Although many efforts have previously been made to construct a mouse susceptible to HIV-1 infection by incorporating human genes into the mouse, such efforts have failed. However, the discovery that APOBEC3G exerts an antiviral activity implies that a mouse susceptible to HIV-1 would have to lack APOBEC3G function. Moreover, the Vif protein of HIV-1 may not be capable of neutralizing the mouse APOBEC3G protein because of known species specificity of Vif function. Hence, knocking out the animal (e.g., mouse) homologue of APOBEC3G, would provide a transgenic animal that is susceptible to HIV infection. This could be achieved by standard gene knockout methods.

Alternatively, the same goal can be achieved by expressing in the transgenic animal another viral protein that neutralizes the mouse APOBEC3G function, or by administering to the mice (or other animal) a drug or inhibitor of APOBEC3G, to enhance replication of HIV-1. Such drugs could be administered to primates infected with SIV, for instance, to accelerate and enhance lentiviral-induced pathogenesis. Accelerated pathogenesis would be helpful to more quickly study a simian model of HIV disease. Moreover, most SIV infections of primates do not cause diseases in their natural hosts. A drug or composition that blocked APOBEC3G function would result in SIV-induced diseases in these cases, yielding new animal models for viral diseases.

Transgenic animals include all mammalian species, for example all species except human. Transgenic animals could also include animals in all stages of development, including embryonic and fetal stages. Farm animals (pigs, goats, sheep, cows, horses, rabbits and the like), rodents (such as mice), and domestic pets (for example, cats and dogs) are included. In one embodiment, the transgenic animal is a mouse that is susceptible to infection by HIV-1. The transgenic animal bears genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. In one embodiment, this molecule is integrated within at least one of the animal's chromosomes.

Transgenic animals also include a "germ cell line" transgenic animal. A germ cell line transgenic animal is a transgenic animal in which the genetic information has been taken up and incorporated into a germ line cell, therefore conferring the ability to transfer the information to offspring. Offspring that possess some or all of that information are transgenic animals. Some transgenic animals have a genome that has been altered by in vitro manipulation of the early embryo or fertilized egg, or by any transgenic technology to induce a specific gene knockout. The term "gene knockout" refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. Thus, the term "transgenic" includes any transgenic technology familiar to those in the art which can produce an organism carrying an introduced transgene or one in which an endogenous gene has been rendered non-functional or knocked out, such as a gene encoding APOBEC3G.

One example of a transgene to be used in this method is a DNA sequence that includes a modified APOBEC3G coding sequence. Thus, the endogenous APOBEC3G gene is disrupted by homologous targeting in embryonic stem cells. For example, the entire murine APOBEC3G homolog may be deleted (e.g., see Genbank Accession No. BC003314.1, which encodes AAH03314 (protein), herein incorporated by reference). Optionally, the APOBEC3G disruption or deletion may be accompanied by insertion of or replacement with other DNA sequences, such as a non-functional APOBEC3G sequence, or an APOBEC3G fusion protein that is detectable or identifiable, or otherwise has an enhanced feature provided by the addition of a fusion protein or peptide.

In one example, an animal (e.g., a mouse) has both copies of the APOBEC3G sequence knocked-out or modified so that their activity is reduced, and has increased susceptibility to infection with HIV-1.

The transgenic animals can be produced by introducing into single cell embryos polynucleotides designed to produce an antisense sequence that binds an APOBEC3G sequence, or siRNA sequence that degrades an APOBEC3G sequence, in the subsequently produced animal. The polynucleotides are introduced into the embryo and are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In one example, developing embryos are infected with a retrovirus containing the desired polynucleotide, and transgenic animals are produced from the infected embryo.

In another embodiment, the appropriate polynucleotides are coinjected into the pronucleus or cytoplasm of embryos, preferably at the single cell stage, and the embryos are allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature*, 315:680, 1985; Purcel et al., *Science*, 244:1281, 1986; Wagner et al., U.S. Pat. No. 5,175,385; Krimpenfort et al., U.S. Pat. No. 5,175,384, the respective contents of which are incorporated by reference.

The polynucleotide that produces an antisense oligonucleotide that binds APOBEC3G mRNA can be produced as a genetic construct that is then amplified, for example, by preparation in a bacterial vector, according to conventional methods. See, for example, the standard work: Sambrook et al., *Molecular Cloning: a Laboratory Manual*, Cold Spring Harbor Press, 1989, the contents of which are incorporated by reference. The amplified construct is thereafter excised from the vector and purified for use in producing transgenic animals.

Example 14

Production of Protein Specific Binding Agents

Monoclonal or polyclonal antibodies may be produced to either a wildtype or reference Vif or APOBEC3G protein or a fusion protein comprising Vif or APOBEC3G or a portion thereof. Optimally, antibodies raised against these proteins or peptides would specifically detect the protein or peptide to which the antibodies are generated. That is, an antibody generated to the specified protein, fusion, or a fragment thereof would recognize and bind that protein and would not substantially recognize or bind to other proteins found in, for instance, human cells. In some embodiments, an antibody is specific for (or measurably preferentially binds to) an epitope in a variant protein (e.g., an mutant or variant of a APOBEC3G or Vif as described herein) versus the reference protein, or vice versa.

The determination that an antibody specifically detects a target protein or form of the target protein is made by any one of a number of standard immunoassay methods; for instance, the western blotting technique (Sambrook et al., In *Molecular Cloning: A Laboratory Manual*, CSHL, New York, 1989). To determine that a given antibody preparation (such as one produced in a mouse) specifically detects the target protein by western blotting, total cellular protein is extracted from human cells (for example, lymphocytes) and electrophoresed on a sodium dodecyl sulfate-polyacrylamide gel. The proteins are then transferred to a membrane (for example, nitrocellulose) by western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target protein will, by this technique, be shown to bind to the target protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-target protein binding.

Substantially pure Vif or APOBEC3G protein, fusion, or protein fragment (peptide) suitable for use as an immunogen may be isolated from the transfected or transformed cells, for instance as described herein. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the target protein identified and isolated as described can be prepared from murine hybridomas according to the classical method of Kohler and Milstein (*Nature* 256:495–497, 1975) or derivative methods thereof.

Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419–439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988–991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against a specific Vif or APOBEC3G protein or peptide (e.g., a peptide that is specific to a variant APOBEC3G or Vif) or fusion is to use one or more synthetic peptides synthesized on a commercially available peptide synthesizer based upon the predicted amino acid sequence of the protein or peptide. Polyclonal antibodies can be generated by injecting these peptides into, for instance, rabbits or mice.

D. Antibodies Raised by Injection of Encoding Sequence

Antibodies may be raised against proteins and peptides by subcutaneous injection of a DNA vector that expresses the desired protein, fusion, or peptide, or a fragment thereof, into laboratory animals, such as mice. Delivery of the recombinant vector into the animals may be achieved using a hand-held form of the Biolistic system (Sanford et al., *Particulate Sci. Technol.* 5:27–37, 1987) as described by Tang et al. (*Nature* 356:152–154, 1992). Expression vectors suitable for this purpose may include those that express a target protein-encoding sequence under the transcriptional control of either the human β-actin promoter or the cytomegalovirus (CMV) promoter.

E. Antibodies Specific for Specific APOBEC3G Variants or Fragments

With the provision of variant APOBEC3G proteins, domains and fragments, the production of antibodies that specifically recognize these protein variants (and peptides derived therefrom) is enabled. In particular, production of antibodies (and fragments and engineered versions thereof) that recognize at least one variant protein with a higher affinity than they recognize a corresponding wild type APOBEC3G is beneficial, as the resultant antibodies can be used in analysis, diagnosis and treatment (e.g., inhibition or enhancement of viral infectivity), as well as in study and examination of APOBEC proteins themselves. In particular embodiments, it is beneficial to generate antibodies from a peptide (usually at least four consecutive amino acids) taken from a variation-specific region of the desired APOBEC3G protein or fusion protein.

Longer peptides also can be used, and in some instances will produce a stronger or more reliable immunogenic response. Thus, it is contemplated in some embodiments that more than four amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual amino acid variation identified in any variant or fusion protein. Instead, it is contemplated that variant-specific antibodies also may each recognize an epitope located anywhere throughout the specified APOBEC3G variant molecule, which epitope(s) are changed in conformation and/or availability because of the mutation. Antibodies directed to any of these variant-specific epitopes are also encompassed herein.

By way of example, the following references provide descriptions of methods for making antibodies specific to mutant proteins: Hills et al., (*Int. J. Cancer,* 63: 537–543, 1995); Reiter & Maihle (*Nucleic Acids Res.,* 24: 4050–4056, 1996); Okamoto et al. (*Br. J. Cancer,* 73: 1366–1372, 1996); Nakayashiki et al., (*Jpn. J Cancer Res.,* 91: 1035–1043, 2000); Gannon et al. (*EMBO J.,* 9: 1595–1602, 1990); Wong et al. (*Cancer Res.,* 46: 6029–6033, 1986); and Carney et al. (*J. Cell Biochem.,* 32: 207–214, 1986). Similar methods can be employed to generate antibodies specific to APOBEC3G variants.

Antibody preparations prepared according to any of these protocols are useful in quantitative immunoassays, which determine concentrations of antigen-bearing substances in biological samples; they are also used semi-quantitatively or qualitatively to identify the presence of antigen in a biological sample; or for immunolocalization of the specified protein.

Optionally, antibodies, e.g., APOBEC3G-specific monoclonal antibodies, can be humanized by methods known in the art. Antibodies with a desired binding specificity can be commercially humanized (Scotgene, Scotland, UK; Oxford Molecular, Palo Alto, Calif.).

It will be apparent that the precise details of the methods and compositions described herein may be varied or modified without departing from the spirit of the described invention. We claim all such modifications and variations that fall within the scope and spirit of the claims below.

We claim:

1. A method for identifying an agent that inhibits Vif-mediated degradation of APOBEC3G in a cell, comprising:
   contacting a cell which expresses Vif and APOBEC3G with a test agent under conditions sufficient to allow interaction between the cell and the agent; and
   determining whether the Vif-mediated degradation of APOBEC3G is inhibited.

2. The method of claim 1, wherein determining whether the Vif-mediated degradation of APOBEC3G is inhibited comprises:
   determining whether there is a statistically significant decrease in the interaction of Vif and APOBEC3G in the cell contacted with the test agent as compared to the interaction of Vif and APOBEC3G in a control cell not exposed to the test agent.

3. The method of claim 1, wherein the agent comprises a peptide or peptidomimetic.

4. The method of claim 1, wherein the agent comprises a non-peptide compound.

5. The method of claim 1, wherein the agent comprises a polypeptide fragment or derivative of Vif.

6. The method of claim 1, wherein the agent comprises a polypeptide fragment or derivative of APOBEC3G.

7. The method of claim 1, wherein inhibiting Vif-mediated degradation of APOBEC3G in a cell comprises at least one of the following:
   interfering with an interaction between Vif and APOBEC3G;
   interfering with Vif production prior to its interaction with APOBEC3G;
   interfering with targeting of Vif-associated APOBEC3G to a proteasome; or
   interfering with proteasomal degradation of Vif-associated APOBEC3G.

8. The method of claim 1, wherein Vif-mediated degradation of ABOBEC3G affects the ability of a lentivirus to replicate in a cell in the presence of a Vif protein or peptide, the method comprising:
   contacting the agent to the cell under conditions sufficient to allow interaction between the cell and the agent;
   evaluating an amount of an APOBEC3G protein or peptide in the cell; and
   comparing the amount of the APOBEC3G protein or peptide in the cell contacted with the agent to an amount of APOBEC3G protein or peptide in a control cell not treated with the agent,
wherein a statistically significant difference in the amount of the APOBEC3G protein or peptide in the cell contacted with the agent, as compared to the control cell not treated with the agent, identifies the agent as one that affects the ability of a lentivirus to replicate in a cell.

9. The method of claim 8, wherein the Vif is expressed in the cell.

10. The method of claim 8, wherein the Vif is expressed from a vector.

11. The method of claim 8, wherein the Vif is expressed from a lentiviral vector.

12. The method of claim 8, wherein the Vif is a fusion protein.

13. The method of claim 8, wherein the Vif protein or peptide and the APOBEC3G protein or peptide are species compatible.

14. The method of claim 8, wherein the cell is in a cell culture.

15. The method of claim 8, wherein the cell is a vertebrate cell, an insect cell, or a fungal cell.

16. The method of claim 8, wherein the cell is a mammalian cell.

17. The method of claim 15, wherein the fungal cell is a yeast cell.

18. The method of claim 8, wherein the cell is infected with a lentivirus.

19. The method of claim 8, wherein the lentivirus is HIV-1, HIV-2, SIV, FIV or another lentivirus that contains a Vif gene.

20. The method of claim 8, wherein the lentivirus is HIV-1 or HIV-2.

21. The method of claim 8, wherein an increase in the amount of APOBEC3G as compared to the control identifies the agent as one that inhibits lentiviral replication.

22. The method of claim 8, wherein evaluating the amount of APOBEC3G in the cell comprises using a high throughput technique.

23. The method of claim 8, wherein evaluating the amount of APOBEC3G in the cell comprises detecting labeled APOBEC3G.

24. The method of claim 23, wherein the labeled APOBEC3G is labeled with one or more of the following: a fluorophore, a chemiluminescent agent, a radioisotope, an epitope tag, an enzyme, a ligand, a metal sol, or a colloid.

25. The method of claim 8, wherein affecting lentiviral replication comprises at least one of the following:
- interfering with an interaction between Vif and APOBEC3G;
- interfering with Vif production prior to its interaction with APOBEC3G;
- interfering with targeting of Vif-associated APOBEC3G to a proteasome; or
- interfering with proteasomal degradation of Vif-associated APOBEC3G.

* * * * *